(12) United States Patent
Schaer et al.

(10) Patent No.: US 10,537,306 B2
(45) Date of Patent: Jan. 21, 2020

(54) MEDICAL TOOL POSITIONING DEVICES, SYSTEMS, AND METHODS OF USE AND MANUFACTURE

(71) Applicant: Shifamed Holdings, LLC, Campbell, CA (US)

(72) Inventors: Alan Schaer, San Jose, CA (US); Tom Saul, Moss Beach, CA (US); Amr Salahieh, Saratoga, CA (US); Colin Mixter, Santa Clara, CA (US); Joseph C. Trautman, Sunnyvale, CA (US); Marc Bitoun, Santa Cruz, CA (US); Todor Jeliaskov, Campbell, CA (US)

(73) Assignee: Shifamed Holdings, LLC, Campbell, CA (US)

(*) Notice: Subject to any disclaimer, the term of this patent is extended or adjusted under 35 U.S.C. 154(b) by 0 days.

(21) Appl. No.: 15/879,292

(22) Filed: Jan. 24, 2018

(65) Prior Publication Data

US 2018/0279994 A1 Oct. 4, 2018

Related U.S. Application Data

(60) Provisional application No. 62/523,706, filed on Jun. 22, 2017, provisional application No. 62/489,900, (Continued)

(51) Int. Cl.
*A61B 8/00* (2006.01)
*A61B 8/12* (2006.01)
*A61B 8/08* (2006.01)
*A61M 25/01* (2006.01)
*A61B 1/00* (2006.01)

(52) U.S. Cl.
CPC ............ *A61B 8/445* (2013.01); *A61B 8/0883* (2013.01); *A61B 8/0891* (2013.01); *A61B 8/12* (2013.01); *A61B 8/42* (2013.01); *A61B 8/4209* (2013.01); *A61B 8/4466* (2013.01); *A61B 8/4483* (2013.01); *A61B 1/0008* (2013.01);
(Continued)

(58) Field of Classification Search
CPC ..... A61B 8/445; A61B 8/4461; A61B 8/4466; A61M 25/0147
See application file for complete search history.

(56) References Cited

U.S. PATENT DOCUMENTS 4,802,487 A 2/1989 Martin et al.
5,817,015 A 10/1998 Adair
(Continued)

OTHER PUBLICATIONS

Wildes et al.; 4D ICE: A 2D Array transducer with integrated ASIC in a 10 Fr catheter for real-time 3D intracardiac echocardiography; IEEE Tansactions on ultrasonics, ferroelectrics, and frequency control; 63(12); pp. 2159-2173;15 pages; (Author Manuscript); Dec. 2016.
(Continued)

*Primary Examiner* — Rajeev P Siripurapu
(74) *Attorney, Agent, or Firm* — Shay Glenn LLP

(57) ABSTRACT

Medical tool positioning and control devices, systems, and methods. Handle assemblies that allow a steerable shaft to be steered, while allowing the separate movement of a medical tool. The handle assemblies can allow for rotation and axial movement of the medical tool, and optionally with an actuator disposed distal to a second actuator that controls steering of the steerable shaft.

9 Claims, 45 Drawing Sheets

Related U.S. Application Data filed on Apr. 25, 2017, provisional application No. 62/479,218, filed on Mar. 30, 2017.

(52) U.S. Cl.
CPC ............ *A61B 8/54* (2013.01); *A61M 25/0108* (2013.01); *A61M 25/0136* (2013.01); *A61M 25/0147* (2013.01)

(56) References Cited

U.S. PATENT DOCUMENTS

| | | | |
|---|---|---|---|
| 5,954,654 A | 9/1999 | Eaton et al. | |
| 6,100,626 A | 8/2000 | Frey et al. | |
| 6,537,217 B1 | 3/2003 | Bjærum et al. | |
| 6,559,389 B1 | 5/2003 | Kornrumpf et al. | |
| 6,669,690 B1 | 12/2003 | Okada et al. | |
| 7,257,051 B2 | 8/2007 | Thomenius et al. | |
| 7,297,118 B2 | 11/2007 | Kristoffersen | |
| 7,331,927 B2 | 2/2008 | Steen | |
| 7,338,450 B2 | 3/2008 | Kristoffersen et al. | |
| 7,438,712 B2 | 10/2008 | Chouinard | |
| 7,451,650 B2 | 11/2008 | Halvorsrod et al. | |
| 7,507,205 B2 | 3/2009 | Borovsky et al. | |
| 7,527,591 B2 | 5/2009 | Haugen et al. | |
| 7,527,592 B2 | 5/2009 | Haugen et al. | |
| 7,569,015 B2 | 8/2009 | Donaldson et al. | |
| 7,621,028 B2 | 11/2009 | Gelly et al. | |
| 7,691,095 B2 | 4/2010 | Bednarek et al. | |
| 7,731,516 B2 | 6/2010 | Puttinger et al. | |
| 7,740,584 B2 | 6/2010 | Donaldson et al. | |
| 7,766,833 B2 | 8/2010 | Lee et al. | |
| 7,783,339 B2 | 8/2010 | Lee et al. | |
| 7,791,252 B2 | 9/2010 | Baumgartner et al. | |
| 7,819,802 B2 | 10/2010 | Secora | |
| 7,824,335 B2 | 11/2010 | Wodnicki | |
| 7,966,058 B2 | 6/2011 | Xue et al. | |
| 8,057,397 B2 | 11/2011 | Li et al. | |
| 8,096,951 B2 | 1/2012 | Kristoffersen et al. | |
| 8,207,652 B2 | 6/2012 | Baumgartner et al. | |
| 8,213,693 B1 | 7/2012 | Li | |
| 8,364,242 B2 | 1/2013 | Li | |
| 8,428,690 B2 | 4/2013 | Li et al. | |
| 8,451,155 B2 | 5/2013 | Amemiya et al. | |
| 8,527,032 B2 | 9/2013 | Li | |
| 8,659,212 B2 | 2/2014 | Eggen et al. | |
| 8,721,553 B2 | 5/2014 | Lee et al. | |
| 8,727,993 B2 | 5/2014 | Lee et al. | |
| 8,742,646 B2 | 6/2014 | Wodnicki et al. | |
| 8,776,335 B2 | 7/2014 | Baumgartner | |
| 8,790,262 B2 | 7/2014 | Li et al. | |
| 8,840,560 B2 | 9/2014 | Hossack et al. | |
| 8,848,560 B2 | 9/2014 | Muruganathan et al. | |
| 8,933,613 B2 | 1/2015 | Amemiya et al. | |
| 8,978,216 B2 | 3/2015 | Calisti et al. | |
| 8,989,842 B2 | 3/2015 | Li et al. | |
| 9,055,883 B2 | 6/2015 | Tgavalekos et al. | |
| 9,295,511 B2 | 3/2016 | Smith et al. | |
| 9,439,625 B2 | 9/2016 | Cogan et al. | |
| 9,575,165 B2 | 2/2017 | Miller et al. | |
| 9,639,056 B2 | 5/2017 | Falter et al. | |
| 2006/0282150 A1* | 12/2006 | Olson ..................... A61F 2/966 |
| | | | 623/1.11 |
| 2008/0287783 A1 | 11/2008 | Anderson | |
| 2010/0113942 A1 | 5/2010 | Eberle | |
| 2010/0168666 A1 | 7/2010 | Tegg | |
| 2010/0249598 A1 | 9/2010 | Smith et al. | |
| 2011/0087071 A1 | 4/2011 | Danitz et al. | |
| 2014/0100445 A1 | 4/2014 | Stenzel et al. | |
| 2015/0094656 A1 | 4/2015 | Salahieh et al. | |
| 2016/0074625 A1* | 3/2016 | Furnish ............ A61M 25/0147 |
| | | | 604/95.04 |
| 2018/0008166 A1 | 1/2018 | Giles | |
| 2018/0360418 A1 | 12/2018 | Saul et al. | |

OTHER PUBLICATIONS

Saul et al.; U.S. Appl. No. 15/833,330 entitled "Medical devices and methods of use," filed Dec. 6, 2017.

\* cited by examiner

SECTION A-A

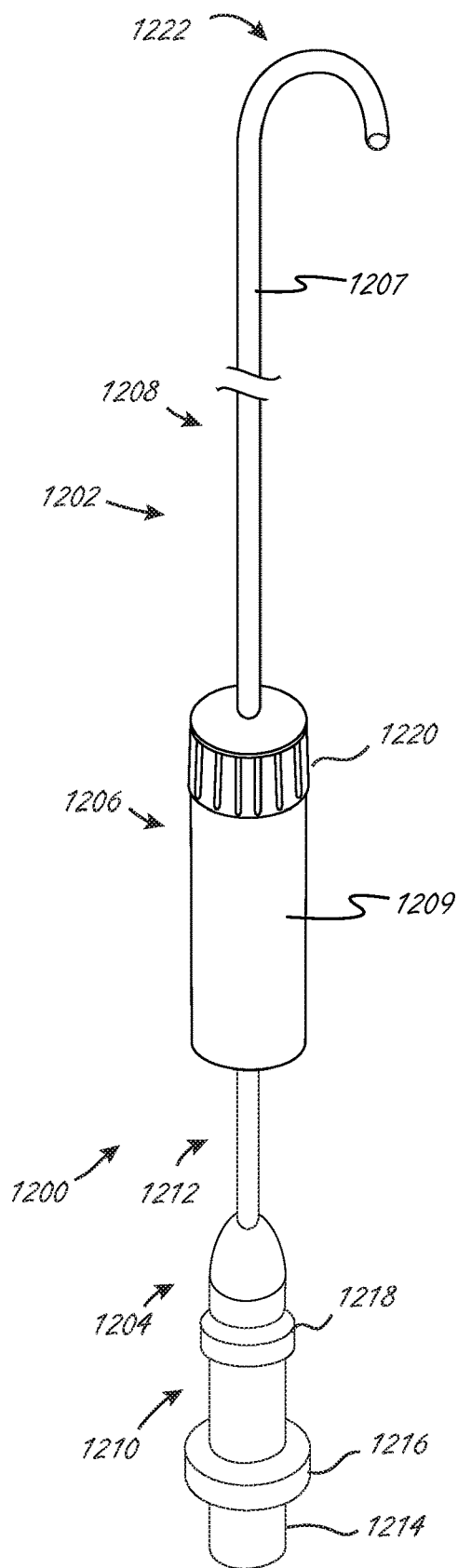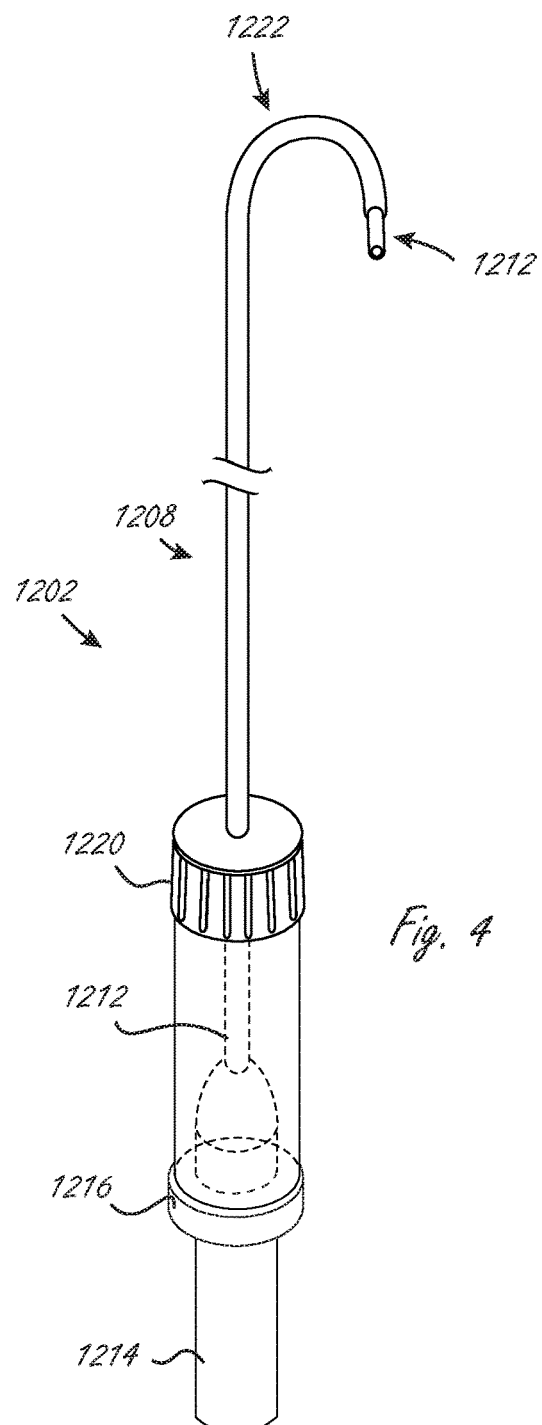
Fig. 3
Fig. 4

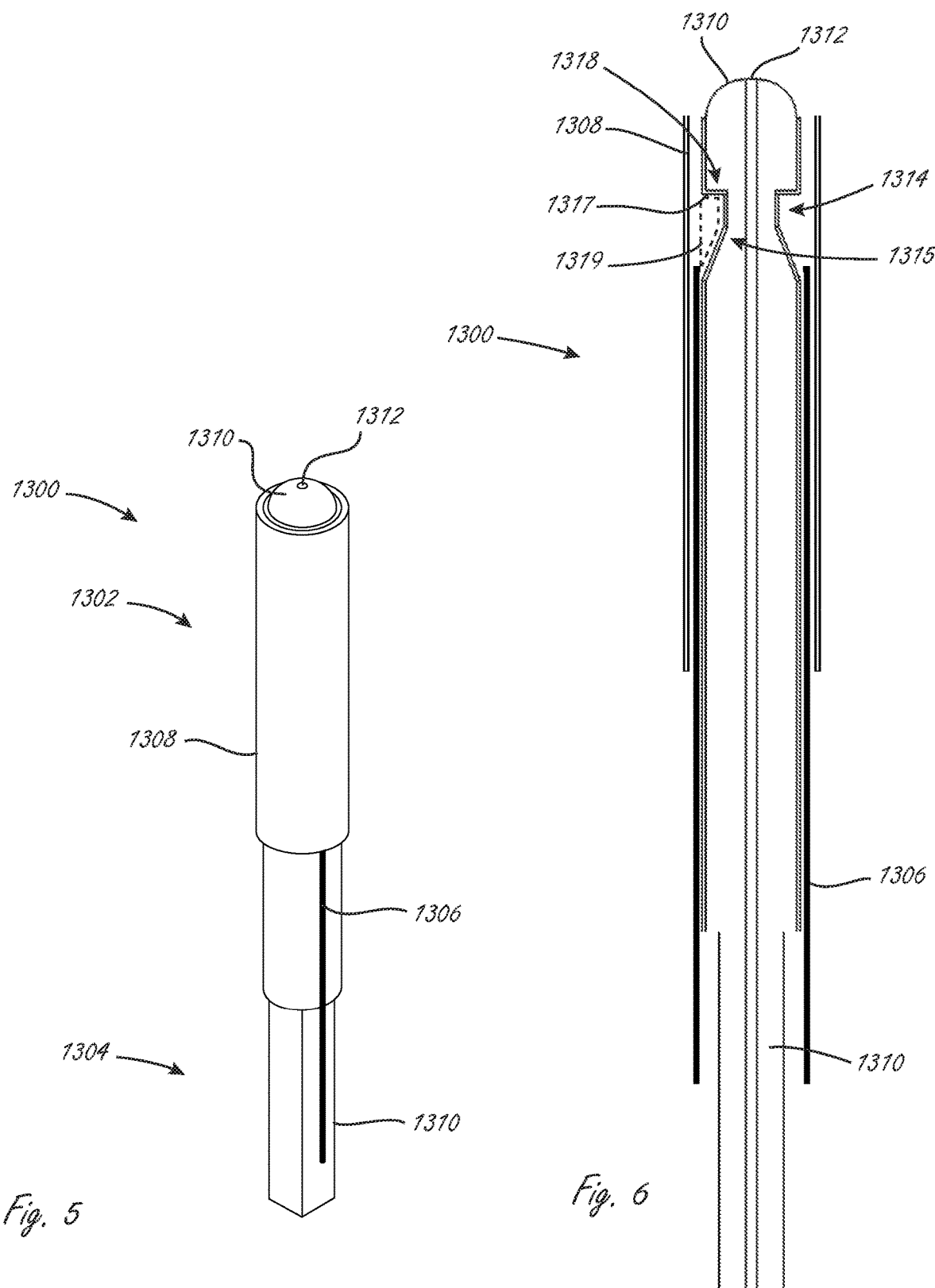

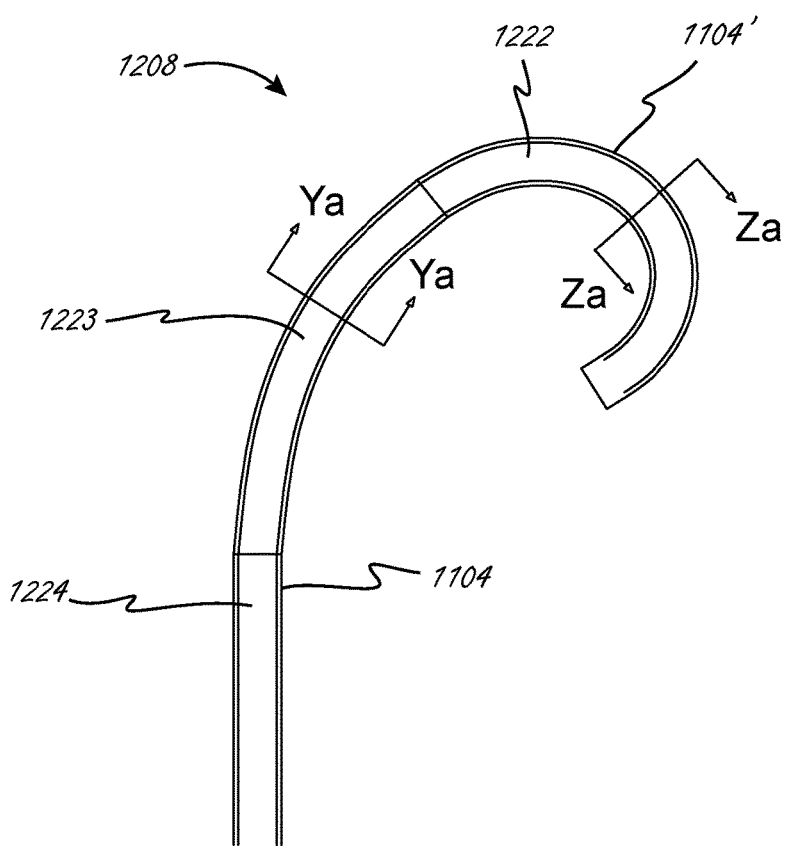
Fig. 7Ai
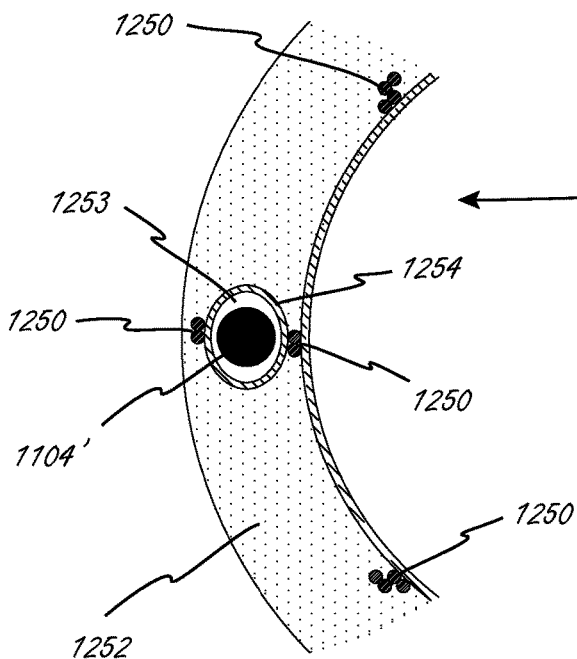
Fig. 7Aii
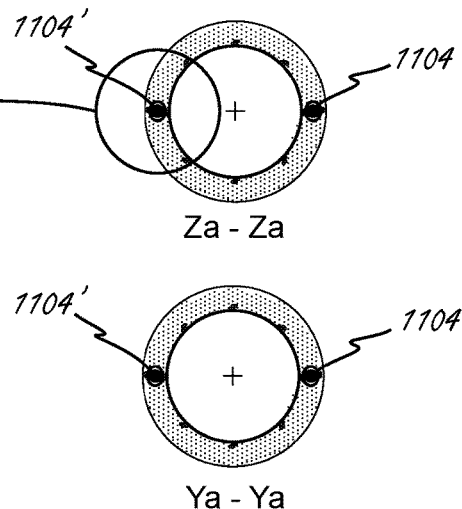
Fig. 7Aiii

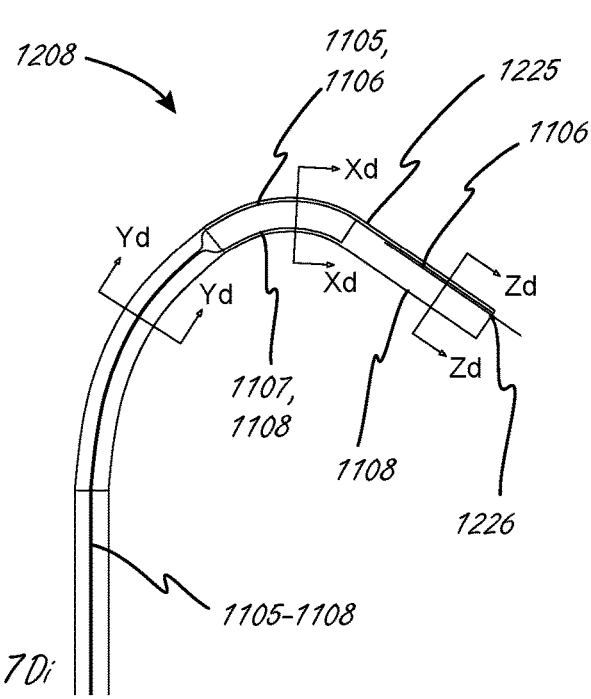
Fig. 7Di
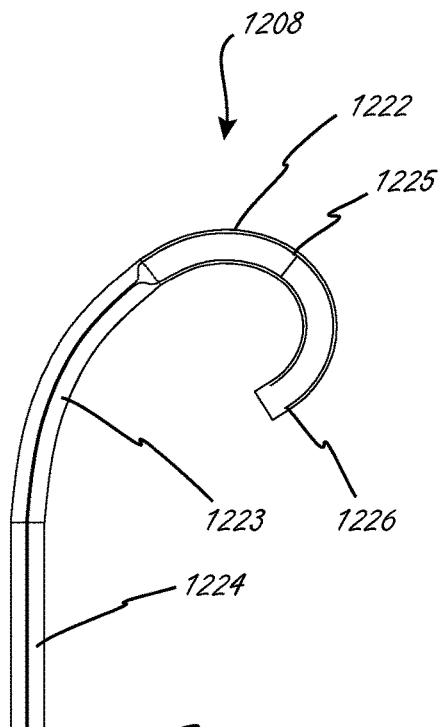
Fig. 7Dii
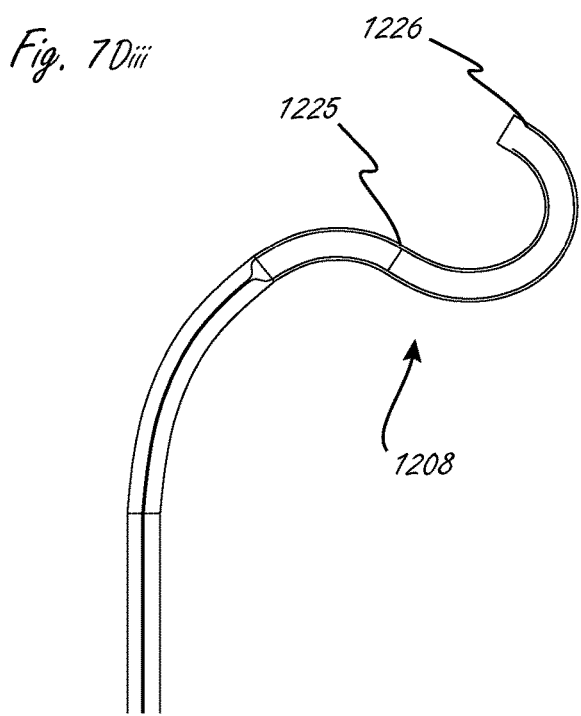
Fig. 7Diii
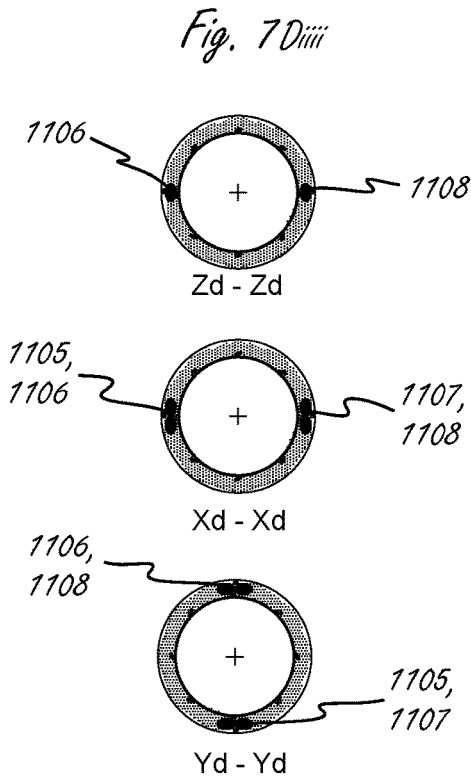
Fig. 7Diiii

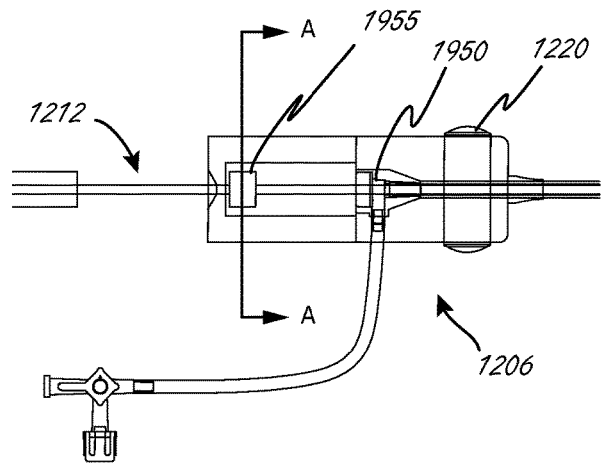
Fig. 10A
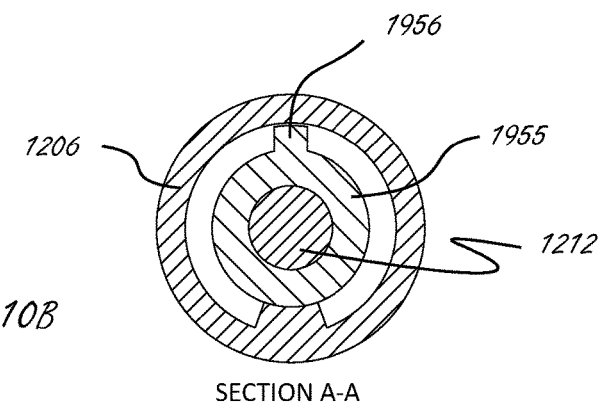
Fig. 10B
SECTION A-A
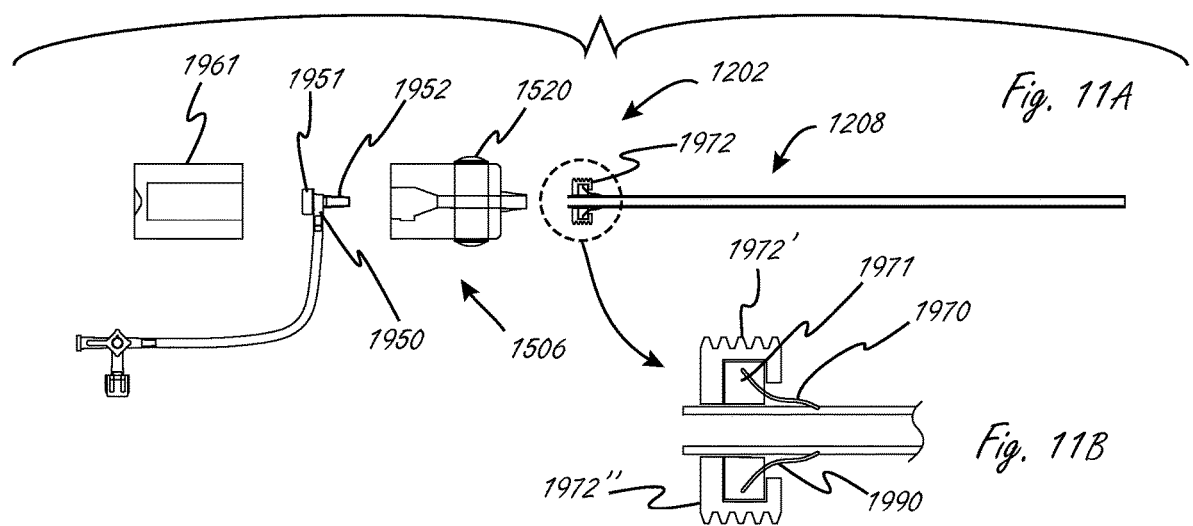
Fig. 11A
Fig. 11B

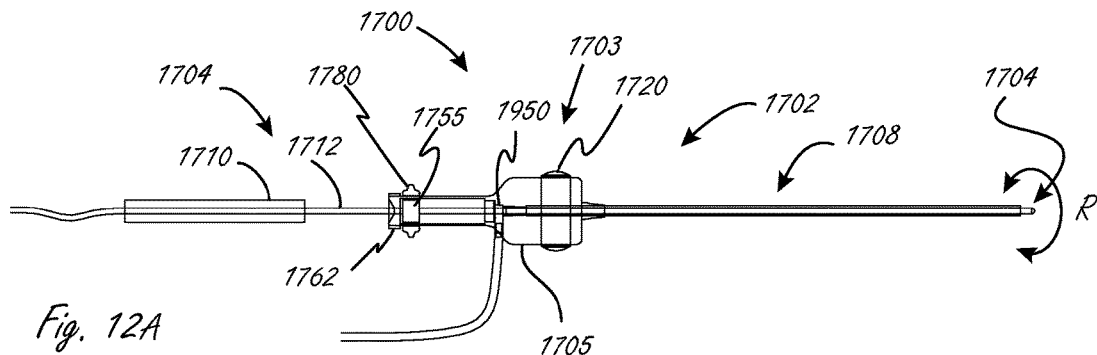
Fig. 12A
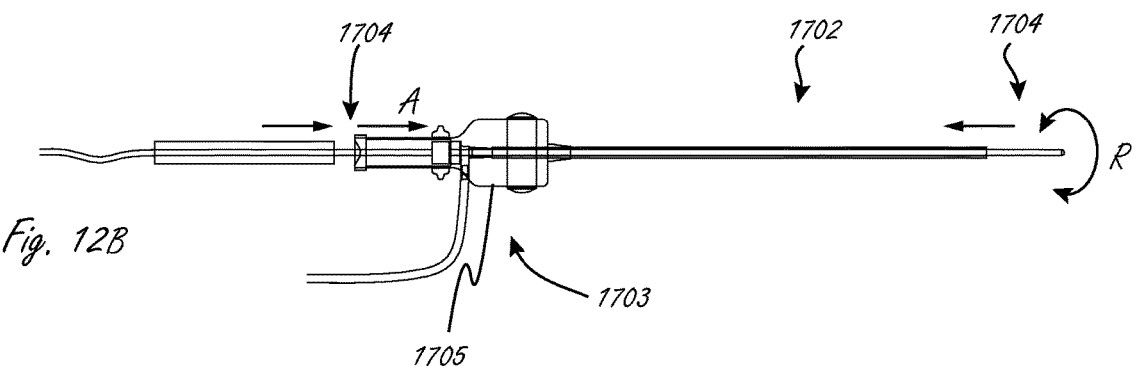
Fig. 12B
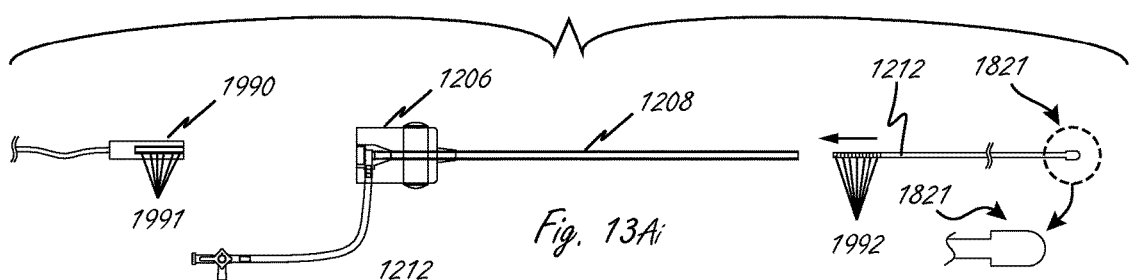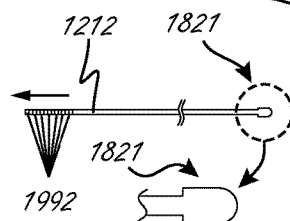
Fig. 13Ai    Fig. 13Aii
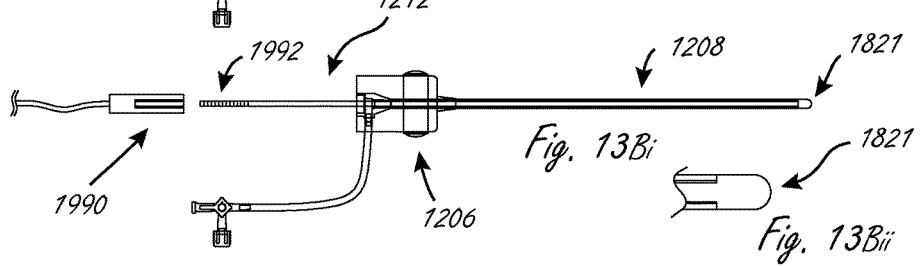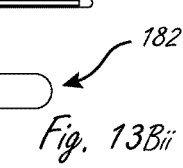
Fig. 13Bi    Fig. 13Bii
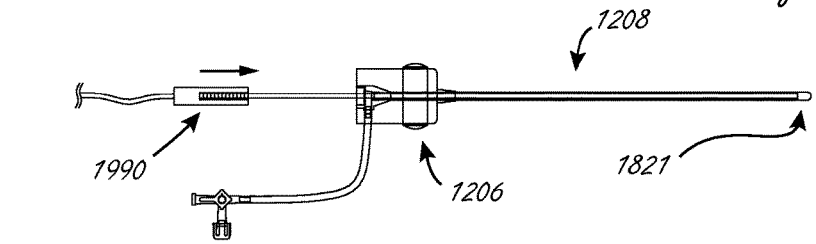
Fig. 13C

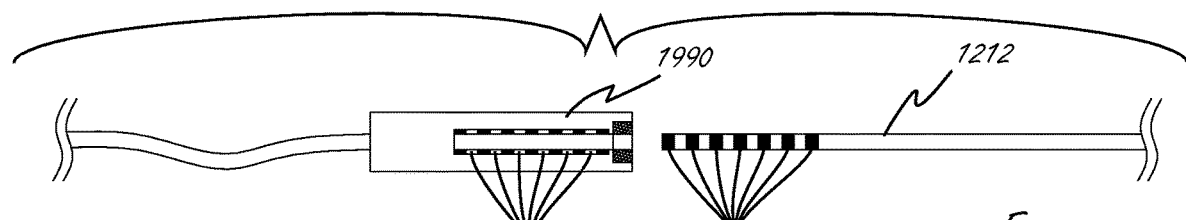
Fig. 14A
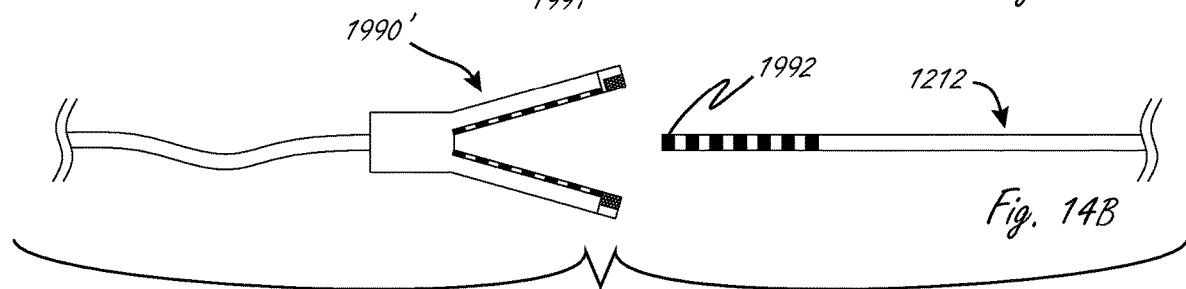
Fig. 14B
Fig. 14C
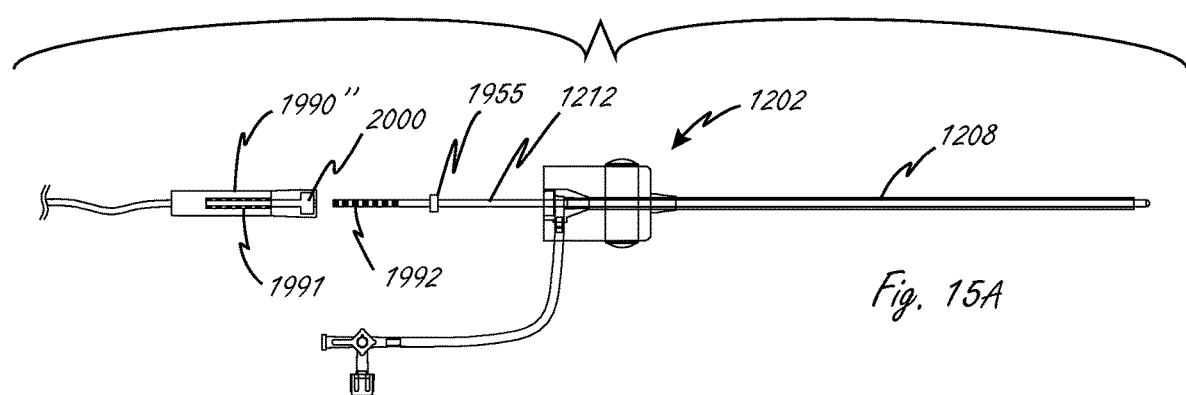
Fig. 15A
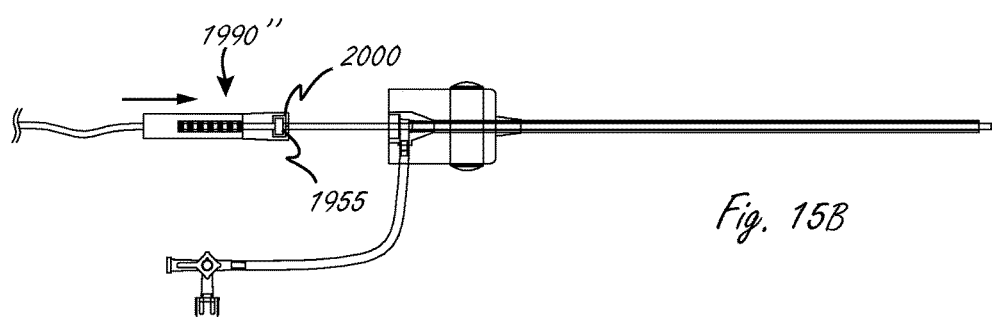
Fig. 15B

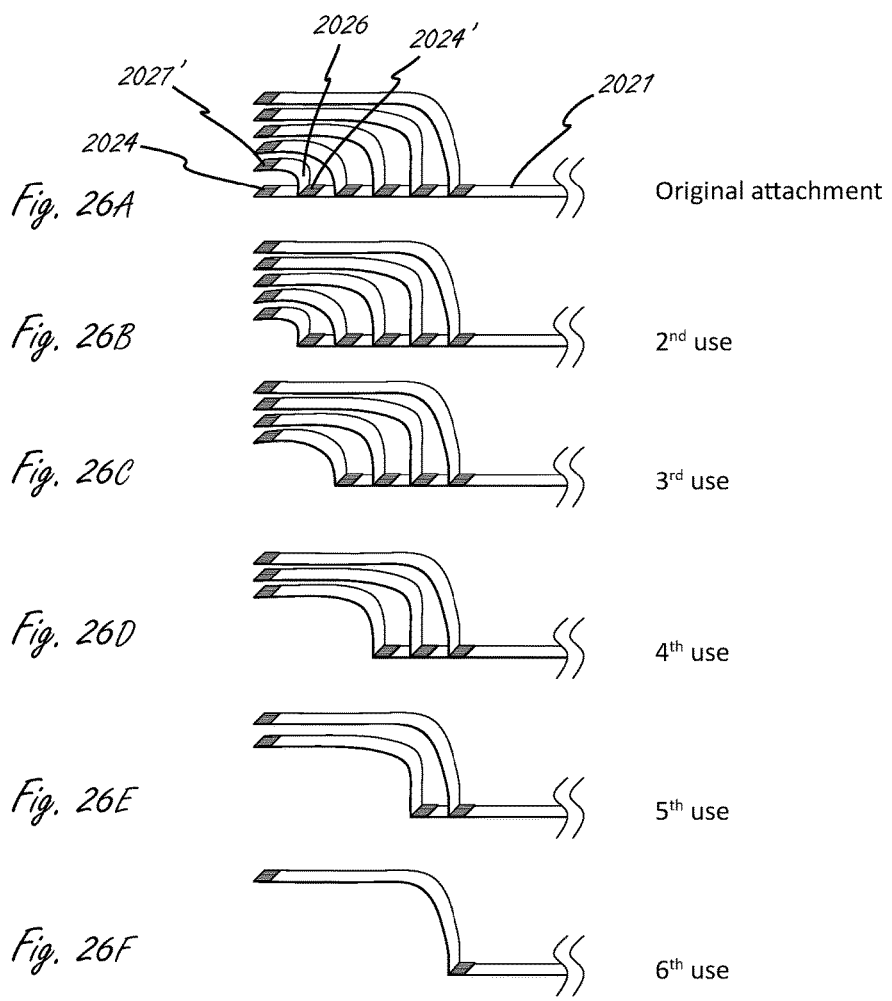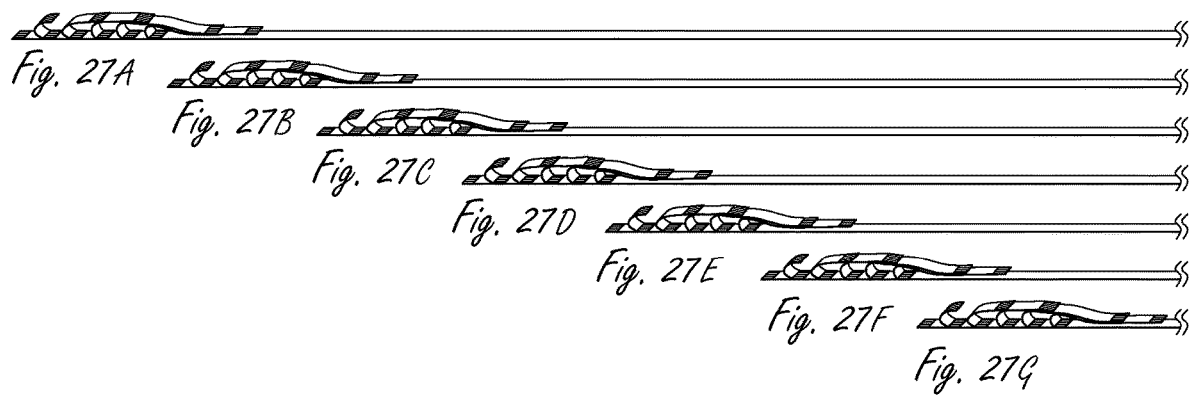

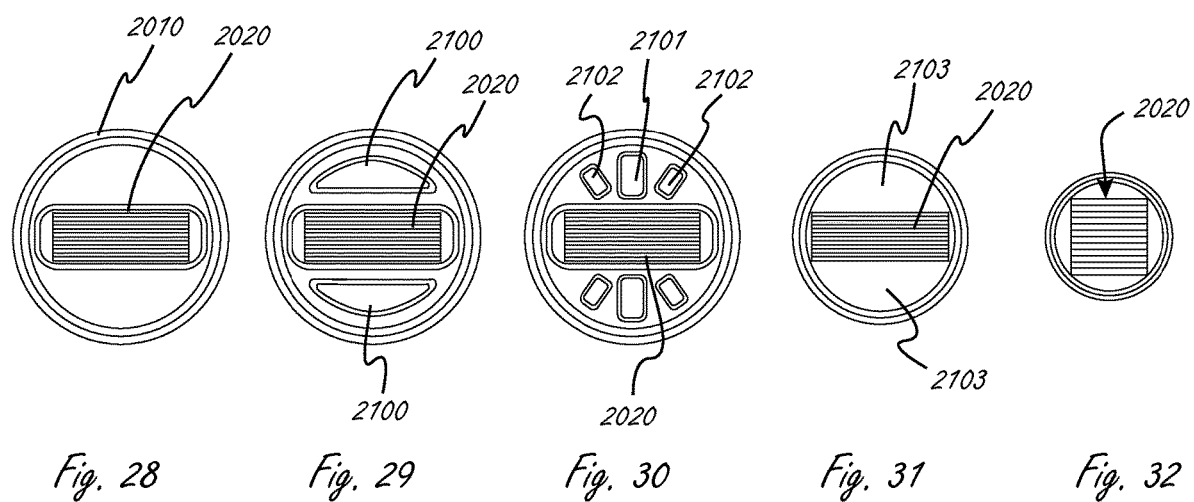

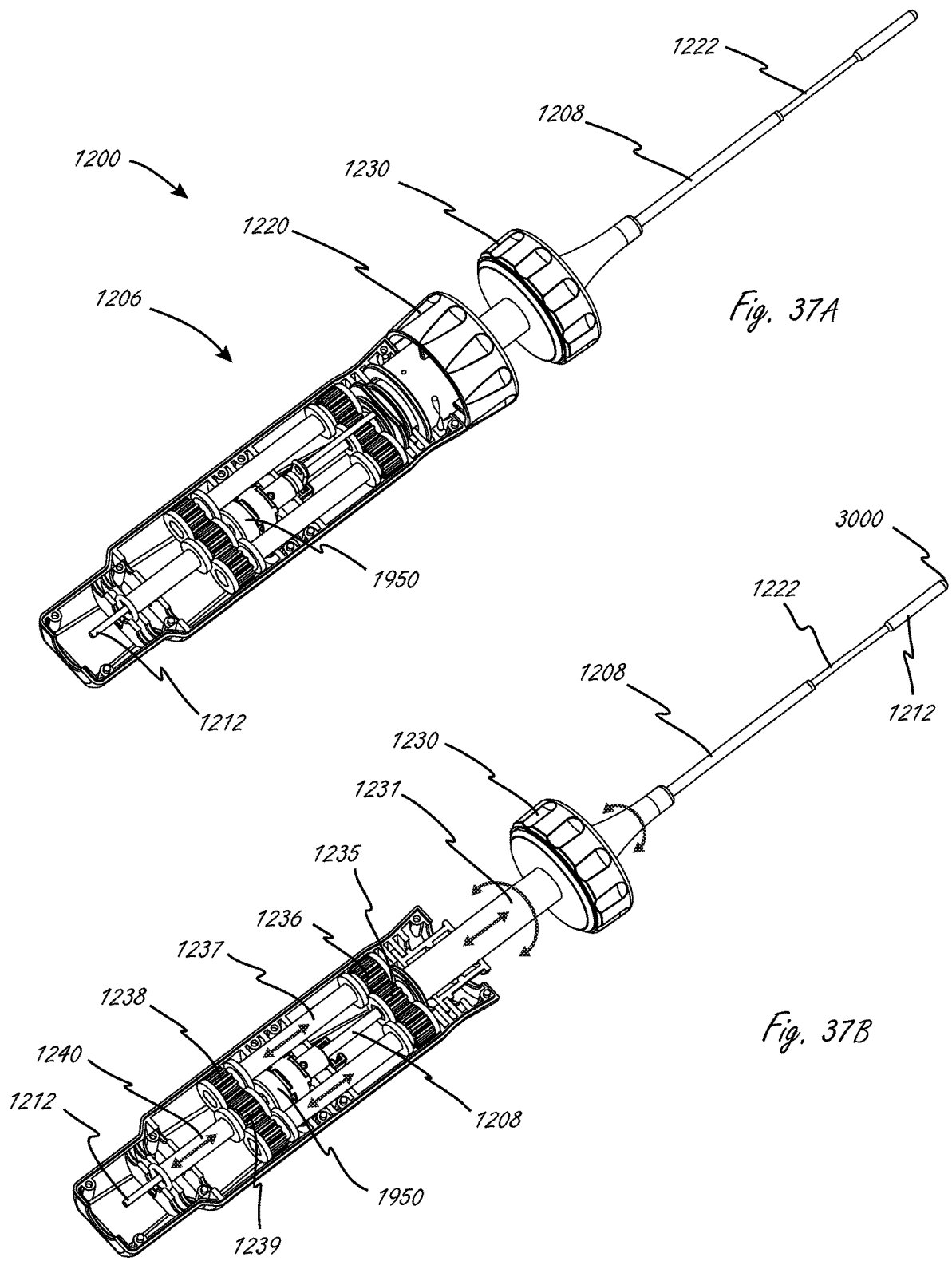

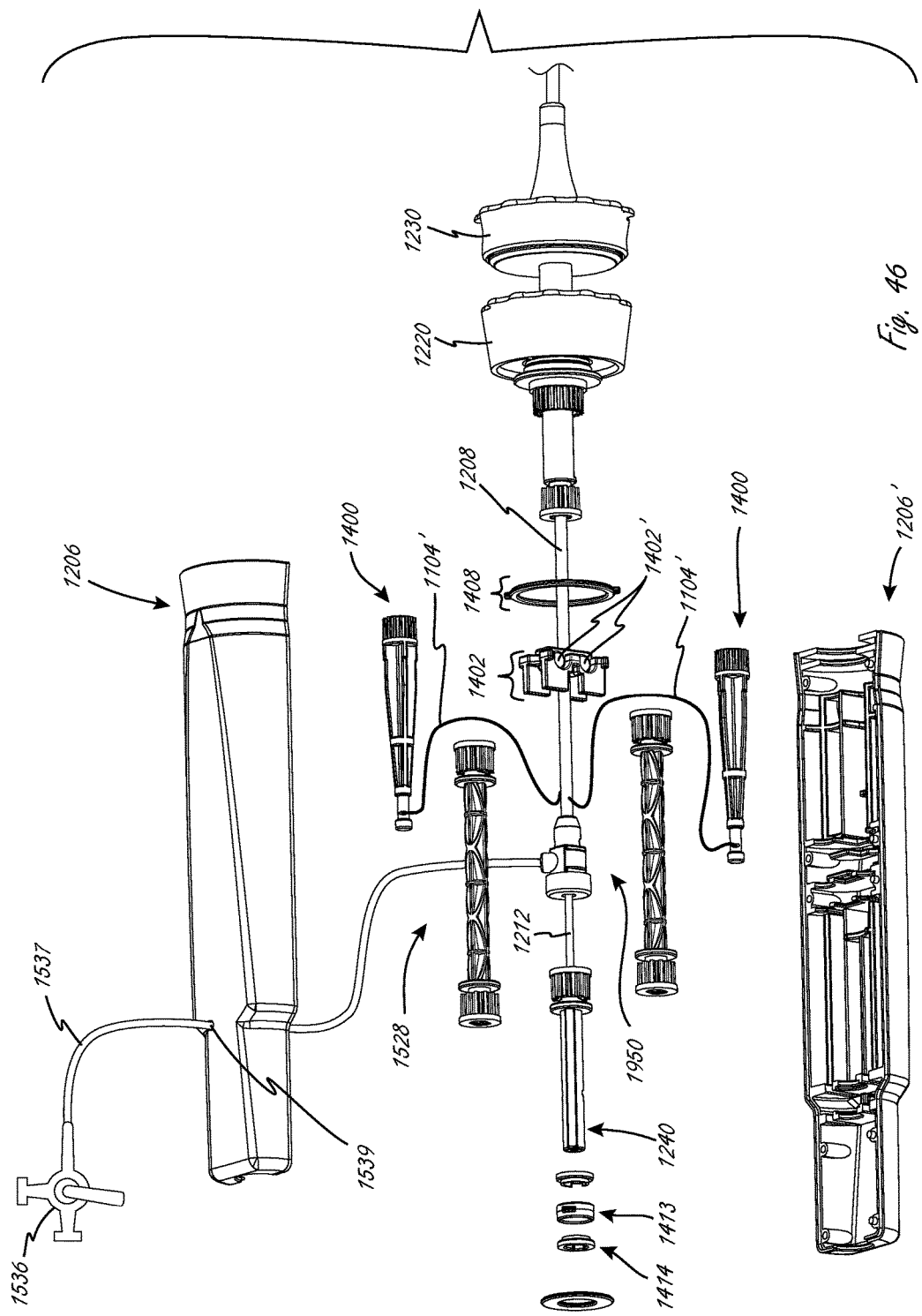

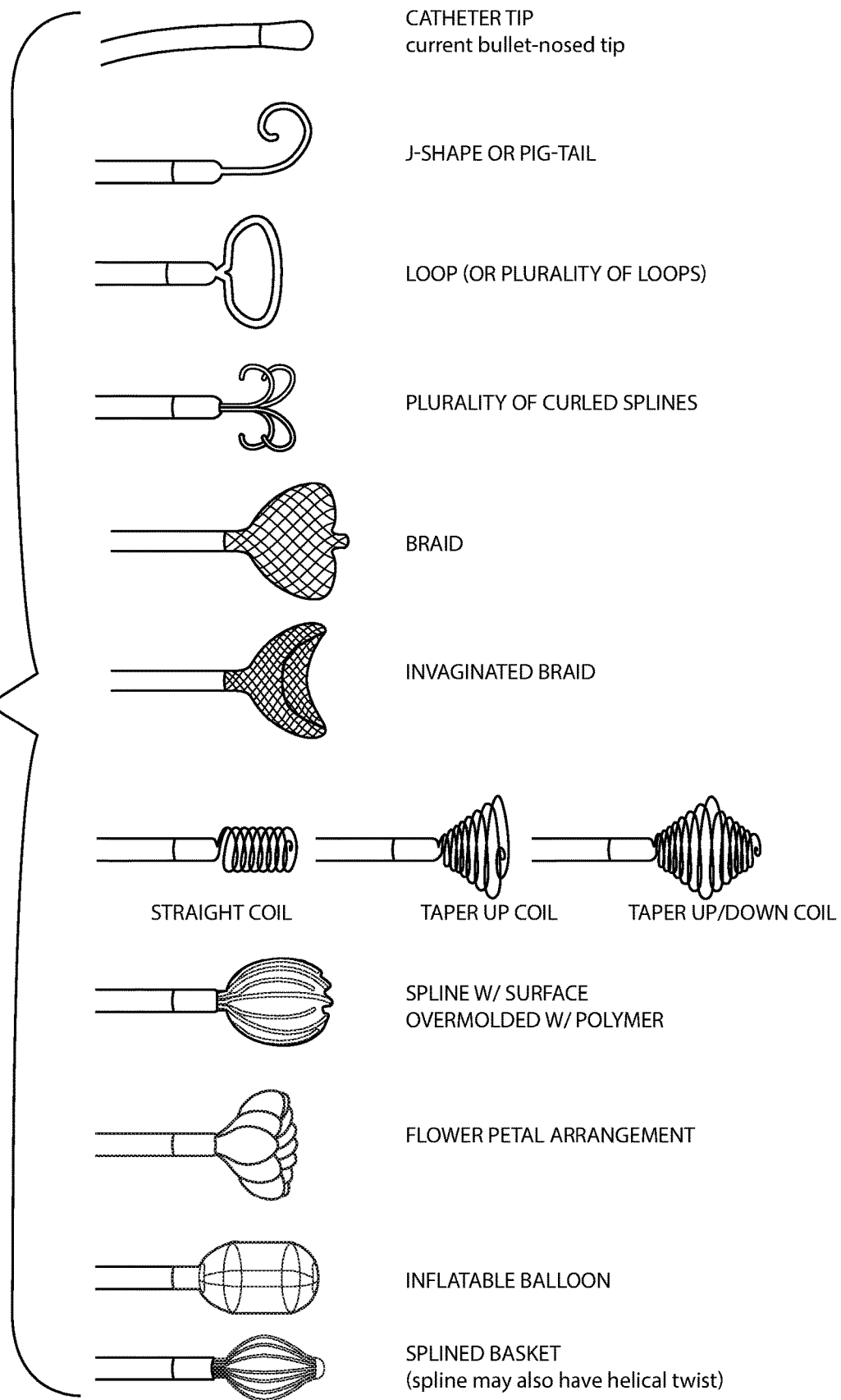

MEDICAL TOOL POSITIONING DEVICES, SYSTEMS, AND METHODS OF USE AND MANUFACTURE

CROSS-REFERENCE TO RELATED APPLICATIONS

This application claims priority to the following provisional applications, the disclosures of which are incorporated by reference herein: U.S. Application Ser. No. 62/479,218, filed Apr. 30, 2017; U.S. Application Ser. No. 62/489,900, filed Apr. 25, 2017; and U.S. Application Ser. No. 62/523,706, filed Jun. 22, 2017.

INCORPORATION BY REFERENCE

All publications and patent applications mentioned in this specification are herein incorporated by reference to the same extent as if each individual publication or patent application was specifically and individually indicated to be incorporated by reference.

BACKGROUND

A wide variety of intravascular medical devices are known. Improved systems, devices, and methods that facilitate better control, positioning, and usability of medical devices are needed.

SUMMARY OF THE DISCLOSURE

One aspect of the disclosure is a handle assembly for positioning a medical tool (e.g., an ultrasound probe), where a first displacement system for the medical tool bypasses a second displacement system for a steerable shaft.

One aspect of the disclosure is a handle assembly for positioning a medical tool (e.g., an ultrasound probe), where a first displacement system for the medical tool extends further proximally than a proximal end of a steerable shaft and optionally further proximally than a hemostatic valve within the handle assembly.

One aspect of the disclosure is a handle assembly for positioning a medical tool (e.g., an ultrasound probe), wherein the handle assembly includes a first actuator movable relative to a handle body, the first actuator adapted to cause axial movement of the medical tool and rotation of the medical tool, the handle assembly including a second actuator proximal to the first actuator and movable relative to a handle body, the second actuator adapted to steer a steerable shaft.

One aspect of the disclosure is a handle assembly for positioning a medical tool (e.g., an ultrasound probe), where a first displacement system for the medical tool is adapted to be moved axially within the handle body while a steerable shaft is not moved axially within the handle body.

One aspect of the disclosure is a handle assembly for positioning a medical tool (e.g., an ultrasound probe), wherein the handle assembly includes a medical tool rotation limiter, optionally an assembly, that prevents rotation of the tool beyond a certain amount. The rotation limiter can be a compound rotation limiter assembly. The rotation limiter can be adapted to allow for more than 360 degree rotation of the medical tool within the handle assembly, and prevent optionally less than 720 degrees of rotation, or optionally less than 675, and optionally less than 630, optionally less than 585, optionally less than 540, and optionally less than 495, and optionally less than 450, optionally less than 405.

One aspect of the disclosure is a handle assembly for positioning a medical tool (e.g., an ultrasound probe), wherein the handle assembly includes a medical tool rotation limiter, wherein at least a portion of the ultrasound probe rotation limiter assembly is disposed proximal to the proximal end of the steerable shaft and proximal to a hemostatic valve disposed in the handle body. The rotation limiter may include a stationary handle element and a first rotating element, the stationary handle element and the first rotating element positioned and configured to interface with one another to prevent further rotational movement of the first rotating element beyond a certain amount of rotation. The rotation limiter may also include a second rotating element secured to or part of a medical tool shaft, the second rotating element rotatable relative to the first rotating element, the second rotating element and the first rotating element disposed relative to one another and each configured to interface one another to cause combined rotation of the first and second rotating elements upon further rotation of the second rotating element.

One aspect of the disclosure is an ultrasound probe that has a distal portion that includes an ultrasound transducer, the distal portion extending further distally than a distal end of a steerable sheath and having a radially outer dimension greater than a radial dimension of a lumen of the steerable sheath in which the probe is disposed, the ultrasound probe further including a flexible circuit strip, the flexible circuit strip comprising an insulating substrate, a plurality of conductive traces disposed on and extending along the insulating substrate, a portion of each of the plurality of conductive traces covered by an insulation member, and a portion of the plurality of conductive traces not covered by the insulation member, the portion of the plurality of conductive traces that are not covered by the second insulation layer defining a probe contact.

One aspect of the disclosure is one or more elements that secure, while allowing movement therein, an ultrasound probe shaft within a handle assembly.

One aspect of the disclosure is a hard stop feature integrated into a handle body, the hard stop feature limiting rotation of a medical tool.

One aspect of the disclosure is an integrated handle body, the handle body including a plurality of guides, some of which may have walls extending along the body's length, while some may be transverse thereto.

One aspect of the disclosure is an ultrasound probe positioning system, comprising: a handle assembly, a steerable sheath; and an ultrasound probe, the handle assembly in operable communication with the steerable sheath and the ultrasound probe, the handle assembly including a handle body with an outer surface that can be gripped by a user, a distal ultrasound probe actuator adapted to be moved relative to the handle body, and a proximal steerable sheath actuator proximal to the distal actuator adapted to be moved relative to the handle body, the steerable sheath having a distal deflectable region that is in operable communication with at least one axially actuatable member, wherein the proximal steerable sheath actuator is in operable communication with the axially actuatable member such that actuation of the proximal steerable sheath actuator relative to the handle body causes deflection of the distal deflectable region, and wherein the distal actuator is adapted to be rotated relative to the handle body and also adapted to be moved axially relative to the handle body, and wherein the distal actuator is in operable communication with the ultrasound probe such that axial movement of the distal actuator relative to the handle body causes axial movement of the ultrasound probe relative to the distal end of the steerable sheath, and such that rotation of the distal actuator relative to the handle body causes rotation of the ultrasound probe relative to the distal end of the steerable sheath, wherein the handle assembly comprises an ultrasound probe displacement system that is attached to the distal ultrasound probe actuator and to an ultrasound probe shaft and that creates operable communication between the distal ultrasound probe actuator and the ultrasound probe shaft, and wherein at least part of the ultrasound probe displacement system is disposed within the handle body and extends further proximally in the handle body than a proximal end of the steerable sheath and is attached to the ultrasound probe shaft at a location proximal to a proximal end of the steerable sheath, and wherein the ultrasound probe displacement system bypasses the steerable sheath within the handle body such that it is not in operable communication with the steerable sheath within the handle body so that the ultrasound probe shaft can be rotated and axially moved without causing movement of the steerable sheath within the handle body. Any of the other relevant features herein may be included in this system.

In some embodiments the part of the ultrasound probe displacement system that is attached to the ultrasound probe shaft is attached to the ultrasound probe shaft proximal to a hemostatic valve disposed within the handle body.

In some embodiments at least a portion of the ultrasound probe displacement system, within the handle body, extends around and outside of the steerable sheath, and is adapted to be moved axially relative to the steerable sheath when the distal actuator is moved axially. The ultrasound probe displacement system can include, within the handle body, a first portion that extends around and outside of the steerable sheath, and a second portion in operable communication with the first portion, the second portion positioned radially away from the steerable sheath and extends in a direction parallel to a longitudinal axis of the sheath. The first portion can include a first rotatable member with a lumen through which the steerable sheath and the ultrasound probe shaft extend, and wherein the second portion can include a second rotatable member spaced radially away from the first rotating member and in operable communication with the first rotating member. The ultrasound probe displacement system can further comprise a third rotatable member with a proximal end that is proximal to the proximal end of the steerable sheath, the third rotatable member positioned radially inward relative to the second rotatable member, the third rotating member having a lumen through which the ultrasound probe shaft extends and which is secured directly or indirectly to the ultrasound probe shaft.

In some embodiments the system further comprises a compound ultrasound probe rotation limiter assembly disposed within the handle body that prevents the ultrasound probe within the handle body from being rotated beyond a certain amount, optionally wherein at least a portion of the ultrasound probe rotation limiter assembly is disposed proximal to the proximal end of the steerable shaft and proximal to a hemostatic valve disposed in the handle body. The rotation limiter assembly can comprise a stationary handle element and a first rotating element, the stationary handle element and the first rotating element positioned and configured to interface with one another to prevent further rotational movement of the first rotating element beyond a certain amount of rotation. The system can further comprise a second rotating element secured to or part of the ultrasound probe shaft, the second rotating element rotatable relative to the first rotating element, the second rotating element and the first rotating element disposed relative to one another and each configured to interface one another to cause combined rotation of the first and second rotating elements upon further rotation of the second rotating element. The compound ultrasound probe rotation limiter assembly can allow for the proximal portion of the ultrasound probe within the handle body to be rotated greater than 360 degrees, and prevents rotation of, optionally, more than 720 degrees, and optionally, more than 450 degrees.

In some embodiments the ultrasound probe has a distal portion that includes an ultrasound transducer, the distal portion extending further distally than a distal end of the steerable sheath and optionally having a radially outer dimension greater than a radial dimension of a lumen of the steerable sheath in which the probe is disposed, the ultrasound probe further including a flexible circuit strip, the flexible circuit strip comprising an insulating substrate, a plurality of conductive traces disposed on and extending along the insulating substrate, a portion of each of the plurality of conductive traces covered by an insulation member, and a portion of the plurality of conductive traces not covered by the insulation member, the portion of the plurality of conductive traces that are not covered by the second insulation layer defining a probe contact.

One aspect of the disclosure is an intravascular ultrasound probe system, comprising: a handle comprising a handle body and an actuator, the actuator movable relative to the handle body, the handle body comprising a stationary rotation stop element; an ultrasound probe comprising a probe shaft at least a part of which is secured within the handle body and is in operable communication with the actuator; and first and second rotatable members that are rotatable relative to the handle body and to the stationary rotation stop element, the first and second rotatable members disposed relative to one another and configured to allow the first rotatable member to rotate without moving the second rotatable member in a first position and then interface with each other in a second position and rotate together when they are interfaced, the second rotatable member and the stationary rotation stop element positioned and configured so that further rotation of the second rotatable member is prevented when second rotatable member and the stop element interface one another, thus preventing the ultrasound probe shaft from being rotated beyond a certain amount.

In some embodiments the compound rotation limiter assembly is configured to allow the proximal end of the ultrasound probe shaft to be rotated more than 360 degrees within the handle body before preventing it from being rotated further, and optionally preventing rotation more than 720 degrees, and optionally preventing rotation more than 450 degrees.

One aspect of the disclosure is a rotation limiter for an intravascular ultrasound probe positioning system, comprising: an annular element with an inner surface defining a lumen therein, the annular element including a radially inner extension that extends further radially inward than a remainder of the inner surface, the radially inner extension, in a sectional end view, having a height from 0.005 inches to 0.042 inches and subtending an angle from 1 degree to 120 degrees, the annular element further including a radially outer extension that extends further radially outward than a remainder of an outer surface of the annular element, the radially outer extension subtending an angle 1 degree to 60 degrees, wherein the remainder of the inner surface has a diameter from 0.319 inches to 0.361 inches, and wherein the length of the annular element from a proximal end to a distal end is from 0.095 inches to 0.188 inches.

In some embodiments the annular element further comprises a second radially outer extension, the second radially outer extension at least 45 degrees away from the radially outer extension around the annular element, and optionally 180 degrees away from the radially outer extension.

In some embodiments the radially inner extension and the radially outer extension are rotationally aligned.

One aspect of the disclosure is a handle body for positioning an intravascular ultrasound probe and preventing rotation of the probe beyond a certain amount, comprising: a handle body comprising an integral rotation stop (1418) that extends radially inward relative to an outer wall of the handle body, the rotation stop having a length from 0.0156 inches to 0.250 inches, and the rotation stop having a height greater than 0.143 inches but not greater than 0.203 inches.

In some embodiments the rotation stop includes a stop surface disposed substantially in an axis that includes a midpoint of the handle body, the midpoint measured along a width of the handle body.

In some embodiments the integral rotation stop has a first width in a proximal portion and a second width smaller than the first width in a distal portion, the distal portion comprising a free end of the integral rotation stop.

In some embodiments the integral rotation stop is from 45.14 inches to 55.38 inches from a distal end of the handle body.

One aspect of the disclosure is an integrated handle body for positioning an intravascular ultrasound probe, comprising: an integrated elongate handle body with a length and width measured perpendicular to one another, the handle body having a proximal region that includes first, second and third proximal guides with lengths longer than their widths, each of the proximal guides including first and second walls extending along the length of the handle body, the first proximal guide being disposed in a central region of the handle body, the second and third proximal guides on either side of the first guide, a central region that includes a plurality central walls extending transverse to the walls in the proximal region, the plurality of central walls each including a plurality of recessed regions formed therein, and a distal region that includes first, second and third distal guides with lengths longer than their widths, each of the distal guides including first and second walls extending along the length of the handle body and transverse to the central walls, the first distal guide being disposed in a central region of the handle body, the second and third distal guides on either side of the first distal guide.

In some embodiments at least one of the first, second, and third proximal guides shares a wall with an adjacent proximal guide.

In some embodiments at least one of the first, second, and third distal guides shares a wall with an adjacent distal guide.

In some embodiments the proximal region further comprises a region proximal to the proximal guides that includes a plurality of rotation walls transverse to the guide walls, each of the rotation walls including a recessed region formed therein.

In some embodiments the second proximal guide is radially aligned with the second distal guide, and the third proximal guide is radially aligned with the third distal guide.

One aspect of the disclosure is an ultrasound probe shaft member that provides at least one of stabilization and driving, comprising: an elongate tubular element with a radially outwardly extending spine extending along at least a the length thereof, the elongate tubular element having an inner lumen with an inner diameter from 0.05 inches to 0.250 inches, such as from 0.080 inches to 0.125 inches, the spine having a height from 0.01 inches to 0.2 inches, such as 0.0157 inches to 0.125 inches, the spine, in a sectional end view, subtending an angle from 1 degree to 180 degrees (optionally to 135 degrees, and optionally to 90 degrees), wherein the elongate tubular element (1240) has a length from 0.5 inches to 3.5 inches, such as from 0.75 inches to 2.5 inches. The shaft member can be coupled to an ultrasound probe shaft, which fixedly secures an outer surface of the probe shaft to the inner lumen of the shaft member.

One aspect of the disclosure is an ultrasound probe positioning system, comprising: a steerable shaft with a first stabilizing feature formed in a distal end region, the stabilizing feature including at least one surface; an ultrasound probe, at least a portion of which is disposed within the steerable shaft and axially and rotationally moveable relative to the shaft, the ultrasound probe including a working end that includes an ultrasound transducer and a second stabilizing feature including at least one surface that is configured and positioned to interface with the first stabilizing feature on the steerable shaft to prevent relative movement between the steerable shaft and ultrasound probe in at least one direction, wherein when the ultrasound probe is moved distally relative to the interfaced position, the relative movement between the steerable shaft and ultrasound probe in at least one direction can occur.

The disclosure herein also includes methods of assembling or reassembling any of the subassemblies or assemblies herein, including any of the subassemblies within any of the handle assemblies herein. For example without limitation, the disclosure here includes methods of spooling one or more pull wires over a bearing surface in a spindle support and then around the spindle surface, examples of which are provided herein.

The methods herein also include manufacturing or constructing any of the individual components of any of the subassemblies or assemblies herein. For example, the disclosure includes methods of manufacturing handle shell components that have particular configurations (e.g., guides, walls, etc.) that can accommodate internal parts that cause the assemblies or subassemblies herein to function as intended.

BRIEF DESCRIPTION OF THE DRAWINGS

FIGS. 3 and 4 illustrate an exemplary embodiment of a system in which the steerable portion can have a cross section equal to that shown in FIG. 2.

FIGS. 5 and 6 illustrate exemplary distal regions of a system in which the steerable portion can include a cross section as illustrated in FIG. 1B.

FIGS. 7Ai, 7Aii and 7Aiii, illustrate an exemplary steerable shaft with pull wires.

FIGS. 7Di, 7Dii, 7Diii and 7Diiii illustrate an exemplary steerable shaft with pull wires.

FIGS. 10A and 10B illustrate a portion of an exemplary system in which a tool lock and handle are configured to limit the range of medical device rotation.

FIGS. 11A and 11B illustrate an embodiment of a system that includes a steerable sheath that has exemplary modular features to aid in reposing the device.

FIGS. 12A and 12B illustrate an alternative embodiment of a system wherein a tool lock is contained within a sheath handle but coupled to an outer control.

FIGS. 13Ai, 13Aii, 13Bi, 13Bii, and 13C illustrate an exemplary system where a medical tool contains a proximal electrical connector containing a plurality of electrical contacts.

FIGS. 14A, 14B and 14C illustrate an exemplary proximal coupling between a medical tool and a connector.

FIGS. 15A and 15B illustrate an exemplary system with a connector that contains an inner feature designed to enclose a tool lock attached to a tool portion.

FIGS. 26A-F illustrates how a flex strip can change as portions are trimmed away at each reposing cycle.

FIGS. 27A-G illustrate an exemplary embodiment in which each stack of redundant extensions is staggered.

FIGS. 28, 29, 30, 31, and 32 illustrate alternate exemplary embodiments of cross-sections of a bundled stack in a lumen, which can be incorporated into any the systems herein.

FIGS. 37A and 37B illustrate an exemplary embodiment of a handle assembly.

FIG. 46 illustrates an exemplary handle assembly.

FIG. 52 illustrates a variety of expandable atraumatic tip features.

DETAILED DESCRIPTION

Figure 1A:
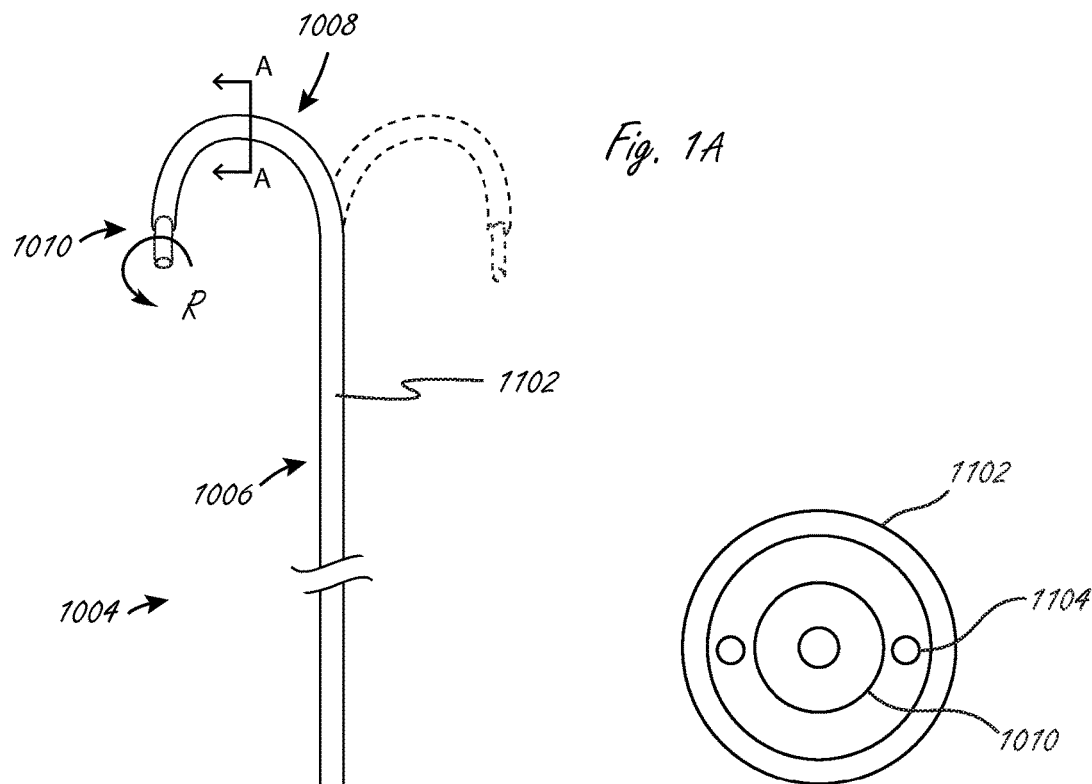
FIG. 1A illustrates an exemplary embodiment of a system that includes steering and a medical device.

FIG. 1A illustrates an exemplary embodiment of a system that integrates steering and a medical device. System 1000 includes handle assembly 1002 and steering and medical device portion 1004. Steering and medical device portion 1004 includes a proximal portion 1006 and steerable portion 1008. The system is adapted so that handle assembly 1002 can be actuated to cause steering of the steerable portion 1008, and optionally can be further actuated to cause movement of medical device 1010 relative to steering and medical device portion 1004. In this exemplary embodiment, handle assembly 1002 includes first actuator 1001, second actuator 1003, and third actuator 1005. First actuator 1001 is adapted to be actuated (in this example rotated) relative to handle body 1007 to cause the steering of steerable portion 1008, and specifically steering outer sheath 1102. Steerable portion 1008 in this embodiment can be steered, or bent, into the configuration shown in FIG. 1A in solid lines, and can also be steered into the configuration shown in dashed lines, or anywhere in between, and in some embodiments the opposite steering function is limited to simply straightening the shaft from an initial bent configuration, such as the solid line bent configuration in FIG. 1A. The term "steer" in this disclosure means to deflect or bend, optionally via actuation of at least one pull wire, but in some instances the term can include shaft rotation (torqueing) and axial movement. The term "pull wire" herein refers to any element that may transmit a tensile force from the proximal end of the device to the distal end region. Pull wires may be comprised of metal wire such as stainless steel or nickel titanium, either solid or stranded/braided, or it may be comprised of a polymer such as aramid fiber (Kevlar®), polyethylene, ptfe, eptfe, etc., preferably stranded/braided, but also in monofilament form. In a preferred embodiment, the pull wire is constructed from an aramid fiber bundle having four 50 denier multifilament (approximately 25 filaments) threads braided together at a high picks per inch. The wire cross-sectional diameter is typically in the 0.005"-0.012" range, more preferably 0.008"-0.010", although braided or stranded wire may flatten or ovalize in the device lumen. The preferred construction embodiments are believed to provide optimized strength and wear resistance for the size necessary to keep the shaft diameters to a minimum. Optional second actuator 1003 is adapted to be actuated relative to handle body 1007 (in this example rotated) to cause rotation of medical tool 1010 relative to shaft 1102 (labeled as rotation movement "R"), and optional actuator 1005 is adapted to be actuated relative to handle body 1007 (in this example axially) to cause axial (distal-proximal) movement of medical device 1010 relative the outer sheath 1102. Proximal portion 1006 is not configured to bend significantly when steerable portion 1008 is steered (bent/deflected), although the proximal portion may flex and bend to conform to the anatomy within which it is used. In many embodiments, this is accomplished by constructing the steerable portion 1008 from a softer or less rigid material and/or composite construction than the proximal portion 1006.

The embodiment shown in FIG. 1A is an example of an apparatus that includes an integrated handle assembly that is in operable communication with both a steerable outer shaft and an inner medical tool. The handle assembly is integrated in that it is assembled and constructed to be in operable communication with the outer shaft and the inner medical tool prior to packaging and use. "Integrated" as that term is used in the context of an integrated handle assembly refers to a handle assembly in which at least one part of the handle assembly has to be broken or taken apart before the medical tool can be removed from within the outer shaft.

Figure 1B:
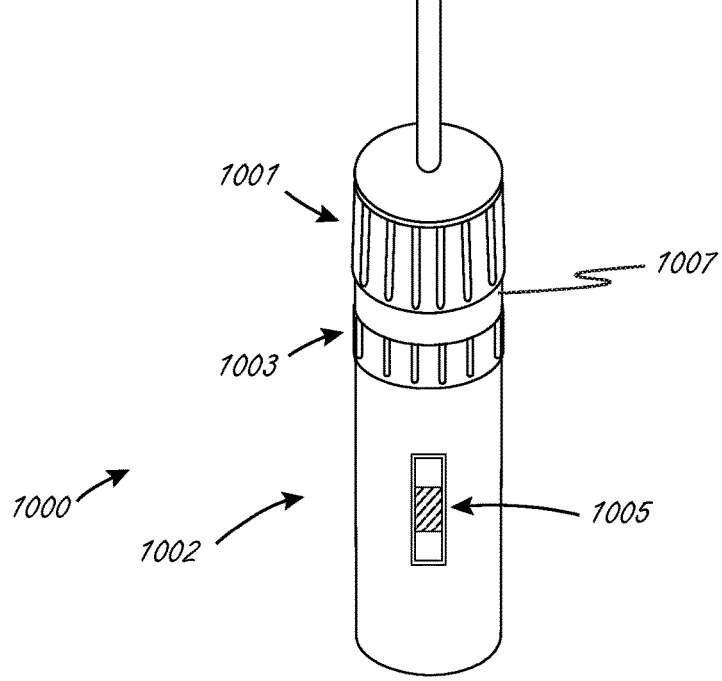
FIG. 1B illustrates a cross section A-A of the steering and device portion of the medical device of FIG. 1A.

FIG. 1B illustrates an exemplary cross section A-A (shown in FIG. 1A) of the steering and device portion 1004, and specifically in the steerable portion 1008. In this embodiment medical device 1010 is sized and configured to be disposed within a steerable sheath. The steerable sheath includes an outer shaft 1102 and a set of pull wires 1104, which are axially fixed in a distal region of steerable portion 1008.

The medical tool in FIGS. 1A and 1B can be, for example, any medical tool herein, such as an ultrasound tool. When "ultrasound probe" is used herein, it generally refers to an elongate tool that includes at least one ultrasound transducer and one or more conductive elements that electrically connect the at least one ultrasound transducer to a proximal region of the elongate tool. A proximal region of the ultrasound probe includes, or is modified to include, at least one proximal contact, which is in electrical communication with the at least one ultrasound transducer, and which can be put into electrical communication with, optionally via attachment to, an electrical contact on another device, cable, or connector.

Figure 2:
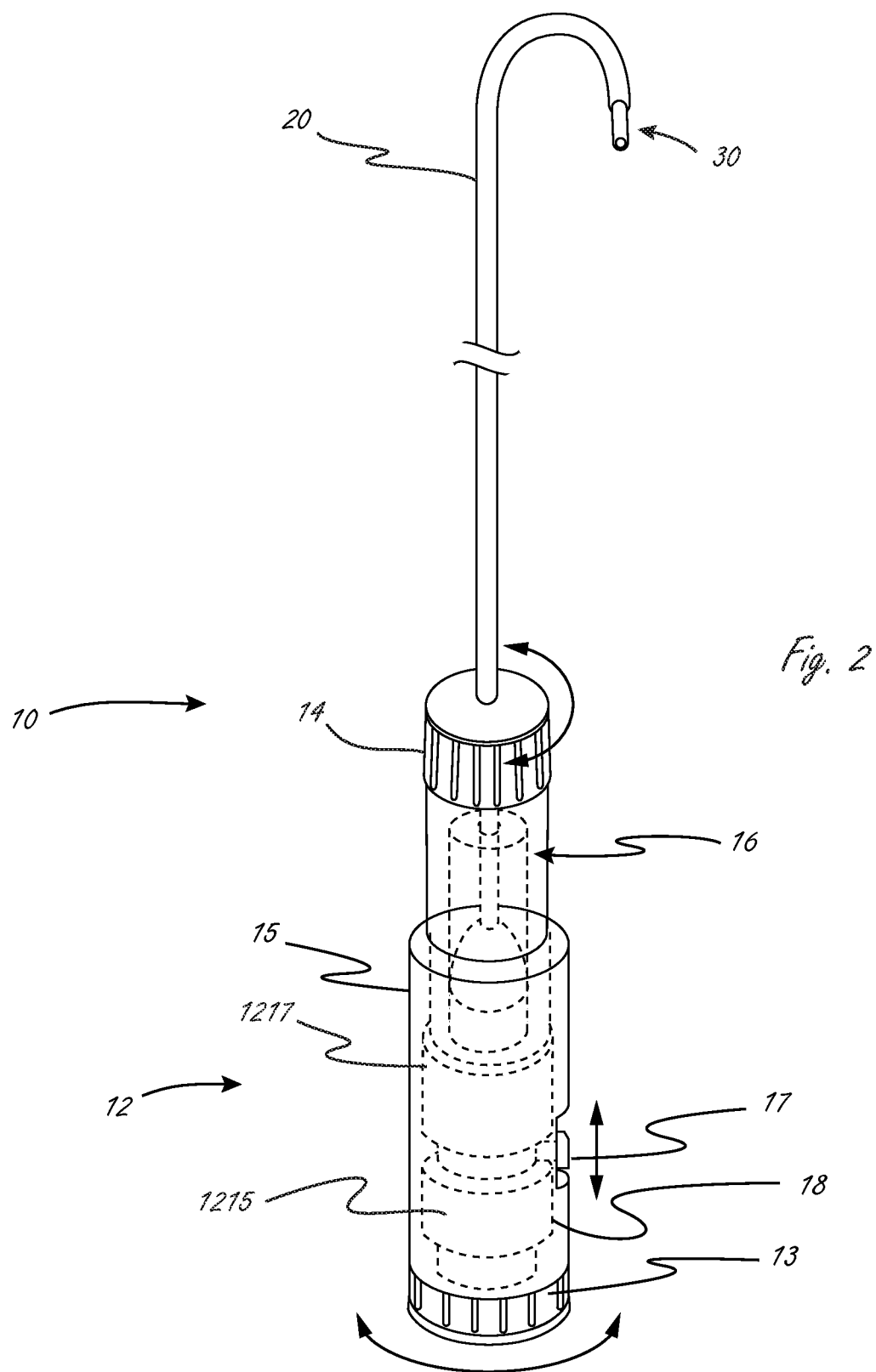
FIG. 2 illustrates an exemplary system that includes a handle assembly with a plurality of actuators, a steerable sheath and medical tool.

FIG. 2 illustrates an exemplary system 10 that is adapted to function similarly to the system in FIGS. 1A and 1B, and also illustrates exemplary internal components of handle assembly 12 (internal components shown as dashed lines). Handle assembly 12 is integrated and in operable communication with outer steerable shaft 20 and medical tool 30. Handle assembly 12 includes actuator 14 that is adapted to, when actuated relative to handle body 15, cause steering of steerable shaft 20. Actuator 14 is in operable communication with steerable shaft 20 via steering control 16 disposed in handle assembly 12. Medical tool 30 includes a proximal portion 18 disposed within and incorporated into handle assembly 12. Actuator 13 is in operable communication with medical tool 30, and actuation of actuator 13 (in this example rotation) relative to handle body 15, causes rotation of medical tool 30 relative to outer shaft 20 via rotation control 1215. Optional third actuator 17 is also in operable communication with medical tool 30, and is adapted to be actuated, in this embodiment, axially (relative to handle body 15), to cause axial movement of medical tool 30 relative to outer steerable shaft 20 via axial control 1217.

The medical tool in FIG. 2 can be, for example, any medical tool herein, such as an ultrasound tool.

FIGS. 3 and 4 illustrate an exemplary embodiment of a system 1200 in which the steerable portion can have a cross section as shown in FIG. 1B. System 1200 includes steerable portion 1202 and medical tool 1204, both of which are configured to interface with each other. Steerable portion 1202 includes handle portion 1206 and a sheath portion 1208, which includes steerable portion 1222. Sheath portion 1208 includes an outer tubular member 1207. Medical tool 1204 includes handle portion 1210 and tool portion 1212, which includes at least one shaft and a working distal region at its distal end. Handle portion 1206 includes steering actuator 1220, which in this embodiment is adapted to be rotated relative to handle body 1209 to cause the steering of steerable portion 1222.

Medical tool 1204 is configured to be advanced through steerable portion 1202, both of which are configured to interface with each other. When advanced, tool portion 1212 of medical tool 1204 is advanced through sheath portion 1208 until its distal end is near the distal end of sheath portion 1208, and a portion of handle portion 1210 is advanced distally within handle portion 1206. Handle portion 1210 of medical tool 1204 includes handle 1214 and stabilizer 1218. Stabilizer 1218 is configured, along with an internal portion of handle portion 1206, to interface one another in a secure relationship to prevent relative movement therebetween in at least one direction. Handle portion 1210 also includes nut 1216, which is configured to interface with a proximal end of handle portion 1206. Stabilizer 1218 acts as an axial constraint for medical tool 1204, relative to steerable sheath 1202.

As shown in FIG. 4, a distal working region of tool portion 1212 is extending distally out of sheath portion 1208 when the medical tool 1204 and steerable sheath 1202 are stably interfacing with one another. In this embodiment the distal end of tool portion 1212 is not axially fixed relative to the distal end of sheath portion 1208.

The medical tool in FIGS. 3 and 4 can be, for example, any medical tool herein, such as an ultrasound tool.

Handle 1214 can optionally include at least one actuator that can cause the axial and/or rotational motion of the medical device relative to the steerable sheath. Thus, once the tool and sheath are stably interfaced, one or more tool handle actuators can control motion of the medical tool (e.g., rotational or axial). The tool and sheath can be interfaced after packaging and just prior to use, or they can be integrated before packaging. Handle 1214 can also include other controls that control the functionality of the medical tool.

FIGS. 5 and 6 illustrate an exemplary distal region of a steerable system that includes an inner medical tool. System 1300 includes steerable sheath 1302 and medical tool portion 1304. Steerable sheath 1302 includes outer member 1308 and one or more pull wires 1306, which are fixed distal to the steerable portion and configured such that, when a handle actuator is actuated, they are moved axially proximal to the steerable portion, which causes their relative axial movement in the steerable portion, which causes the steerable portion to be steered (as is described above). Pull wire 1306 can be parallel to the central axis in the steerable portion of the sheath.

In this merely exemplary embodiment, tool portion 1304 includes an elongate medical tool 1310 that includes an RF tip electrode at its distal end, and a guidewire lumen 1312, but the medical tool can be any other medical tool herein. In this embodiment tool 1310 and steerable sheath 1302 are configured so that the tool distal end (including the region very near the distal end) is axially immovable but rotationally movable relative to the steerable sheath 1302 distal end (including the region very near the distal end). To make the parts axially immovable and rotationally movable, outer member 1308 includes an extension 1314 that extends radially inward relative to the inner surface of outer member 1308 proximal to extension 1314. Tool 1310 includes a region with an outer configuration 1315 (radially inwardly shaped) that corresponds to the extension 1314. The two components similarly have shaped elements 1317 and 1318 distal to elements 1314 and 1315. The configuration of the tool and outer member therefore prevents distal and proximal movement of the tool relative to the outer member and therefore the steerable sheath when the tool and sheath are interfaced as shown. In this embodiment tool 1310 is rotationally free, or moveable, relative to steerable sheath. That is, while tool 1310 cannot move axially at the fixation location (which is distal to the steerable portion) it can be rotated. Being rotationally free can be beneficial if the medical tool, including one or more instruments thereon, should be oriented in or facing a particular direction.

Because the tool and the sheath are axially fixed distal to the steerable portion, the proximal end of the tool is configured to be able to move slightly axially during steering. For example, a spring built into the handle can allow the tool shaft to move slightly relative to the steerable sheath. Other ways of allowing for proximal axial movement can be incorporated as well.

The proximal end of system 1300 can include the two handle components such as those shown in the embodiment in FIGS. 3 and 4, and can be similarly interfacing, with the exception of the moderate axial movement of the tool at the proximal end.

In other embodiments the distal region shown in FIGS. 5 and 6 can be incorporated with a handle assembly shown in FIG. 1A or 2.

One aspect of the disclosure is a method of rendering two co-axial components that were previously axially movable axially immovable (axially fixing them). This aspect also includes methods of removing the axial fixation such that the components can again be axially moved. This can be considered releasable axial fixation. The axial fixation is created, in general, prior to advancing the system into a patient, and in some embodiments the axial fixation is created during manufacturing. The release of the axial fixation can occur during a refurbishing process, and the axial fixation can again be created during a refurbishing process.

In some embodiments the system can be modified to include a component whose volume can be modified (increased or decreased) to cause the axial fixation of the medical tool. In some embodiments the component has a configuration that changes to cause the axial fixation of the medical tool.

In some embodiments system 1300 is adapted so that extension 1314 is configured such that its volume can be modified to cause or release the axial fixation. In this particular modification, fillable annular volume 1319 (shown and labeled only once in the cross-section but it is understood that it exists on the other side due to its annular configuration) is adapted to be filled with a filling material, and such that the filling material can be removed as well. In these alternative embodiments the outer member includes an annular filling volume 1319 defined by the radially outer dotted line surface and by the radially inner portions of the previously described extension 1314. That is, extension 1314 is modified to include a fillable annular chamber or volume 1319, but outer surfaces of extension 1314 remain and define the annular fillable volume 1319.

When it is desired to allow tool 1310 and sheath 1302 to be relatively axially movable, such as during manufacture of the system, fillable volume 1319 remains at least partially un-filled, so that tool 1310 can be easily advanced or retracted axially within sheath 1302. When it is desirable to render tool 1310 and 1302 axially immovable, or fixed, (after they are in desired relative axial positions—such as during manufacturing or refurbishment), fillable volume 1319 is filled with a filling material so that the extension extends radially inward and becomes more rigid, preventing the axial movement of tool 1310 relative to sheath 1302. The extension in this embodiment is thus a reconfigurable axial restraint.

If it is desirable to axially move the tool 1310 and sheath 1302 at a later time (such as during refurbishment—e.g., at least one of cleaning and sterilizing), the fillable material can then be removed from volume (or chamber) 1319, making extension less rigid, so that tool 1310 can be axially moved relative to sheath 1302.

In these alternative embodiments extension 1314 can be considered expandable and unexpandable; fillable and unfillable; reconfigurable; configured and adapted to have a stiffness that can be modified; configured so that its rigidity can be modified; and having a volume that can be modified.

In some embodiments the fillable material can be inserted and removed from annular fill volume 1319 with a fill device such as a needle.

In one exemplary use, tool 1310 is axially advanced to the position in FIG. 6, and fill volume 1319 is thereafter filled with a filing material to axially fix tool 1310 and sheath 1302 (e.g., during manufacture or refurbishment). The method can also include removing the filling material and axially moving at least one of the tool 1301 and sheath 1302 (e.g., during refurbishment).

In an exemplary embodiment the filling material can be modified from a solid to liquid, and visa-versa, by changing its temperature. In some embodiments the fillable (also referred to herein as "filling") material is solid at operating temperature to increase the volume or rigidity of extension 1314, but can be melted (or made less viscous) to allow it to be removed from annular volume 1319.

In some embodiments the filling material is a wax. The wax can, in some embodiments, have a melting point less than a polymeric material of an adjacent component, such as an inner or an outer member.

This concept of creating axial fixation (and allowing removal of the axial fixation) by, for example, adding and removing a filling material, can be used to axially fix any two components herein, including an outer sheath of a steerable sheath and the medical tool within it.

Figure 7B:
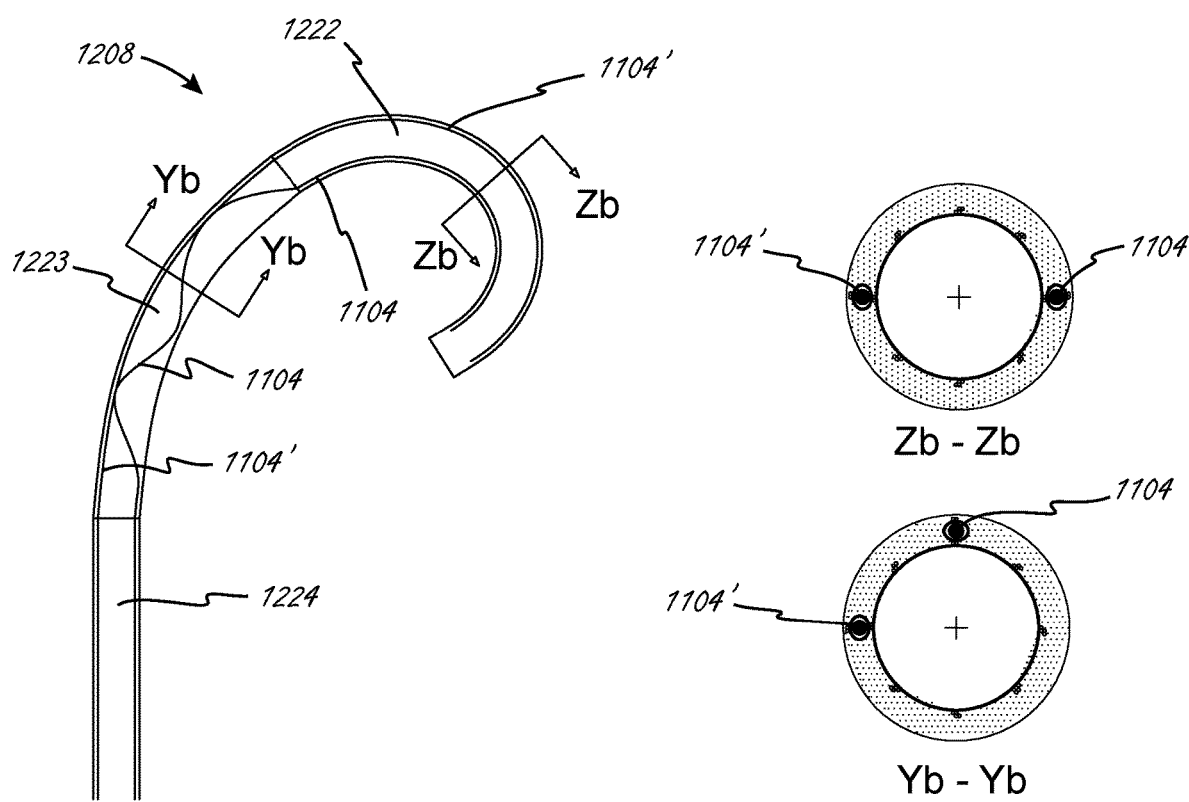
FIGS. 7Bi and 7Bii illustrate an exemplary steerable shaft with pull wires.

FIGS. 7A-7E represent exemplary embodiments of a distal region of the sheath portion 1208 of steerable sheath 1202 in system 1200. For simplicity, the illustrated cross-sections show only the outer sheath 1208 and not the inner tool 1212. The outer sheath 1208 preferably has a composite construction to improve torque transmission applied to the outside of the shaft from the proximal end, or to resist torque forces applied to it from within the shaft, such as from tool 1212. As illustrated in FIG. 7Ai-iii, in order to form the composite, multiple braid elements 1250, preferably formed from metal wire (round, pairs of round, or ribbon shaped) and/or multiple fibers (e.g., aramid or nylon), may be braided directly over a thin wall (e.g., 0.0010"±0.0005") lubricious liner tube 1251, such as a PTFE or FEP material. A thermoplastic polymer 1252 (such as Pebax in a range of durometers from 25 D-72 D, or nylon, or other common catheter materials) may be laminated with heat using heat shrink tubing (such as FEP) to reflow the polymer over the braid elements 1250 and liner tube 1251 to form a uniform member. The thermoplastic polymer 1252 may also have radiopaque compounds that include materials such as bismuth, barium sulfate, or tungsten in order that the tip of the sheath be visible to the user under fluoroscopy. In the embodiment of FIG. 7Ai-iii, the pull wire 1104 is preferably parallel to the central access in the steerable (deflectable) portion 1222 of the sheath and also preferably provided in a lumen 1253 created within the wall of the steerable sheath 1208. This lumen may be created during the thermoplastic polymer tubing extrusion process or during a shaft heat lamination fusing process with the aid of a removable mandrel. The pull wire lumen 1253 may further be created by incorporating a pull wire tube 1254, preferably temporarily supported by a removable mandrel, within the wall. The removable mandrel may also be placed alongside the pull line 1104 or 1104' during the fusing process, resulting in a somewhat ovalized lumen 1253 within which a fiber pull wire may be allowed to flatten into, allowing space for free movement of the pull wire. The tube 1254 may include PTFE, FEP, polyimide, or another material which maintains its wall integrity during a heat lamination process up to approximately 500° F. The tube is preferably surrounded and supported by the thermoplastic polymer 1252 which is preferably heat laminated against the tube. In another embodiment, the pull wire lumen, preferably comprising the pull wire tube, is incorporated within the weave of the braid elements 1250. For example, braid elements 1250 running in one direction would pass under the pull wire lumen, while those running in the opposite direction would pass over the pull wire lumen. The braid reinforcement provides a more dimensionally stable lumen during catheter manipulations and also helps assure the straightness of the lumen as needed. Proximal to the steerable portion, the pull wire may continue proximally parallel to the central axis on the same side of the outer sheath 1208, such as is illustrated in FIG. 7Ai-iii. In this embodiment and others that follow, an additional pull wire 1104' within an additional pull wire lumen routed within the wall of sheath 1208, up through the steerable portion 1222, may be required to straighten the steerable portion of the device. This straightening pull wire 1104' is preferably routed within steerable portion 1222 on the side opposite from the pull wire(s) 1104 used for steering (deflection) in the steerable portion 1222. In another embodiment, not shown, two lumens and two straightening pull wires 1104' could be used, essentially mirroring the paired 1104 pull wire configuration. These straightening wires could also be constructed to allow deflection in the opposite direction by tensioning a greater distance (beyond just straightening) within the handle.

Figure 7C:
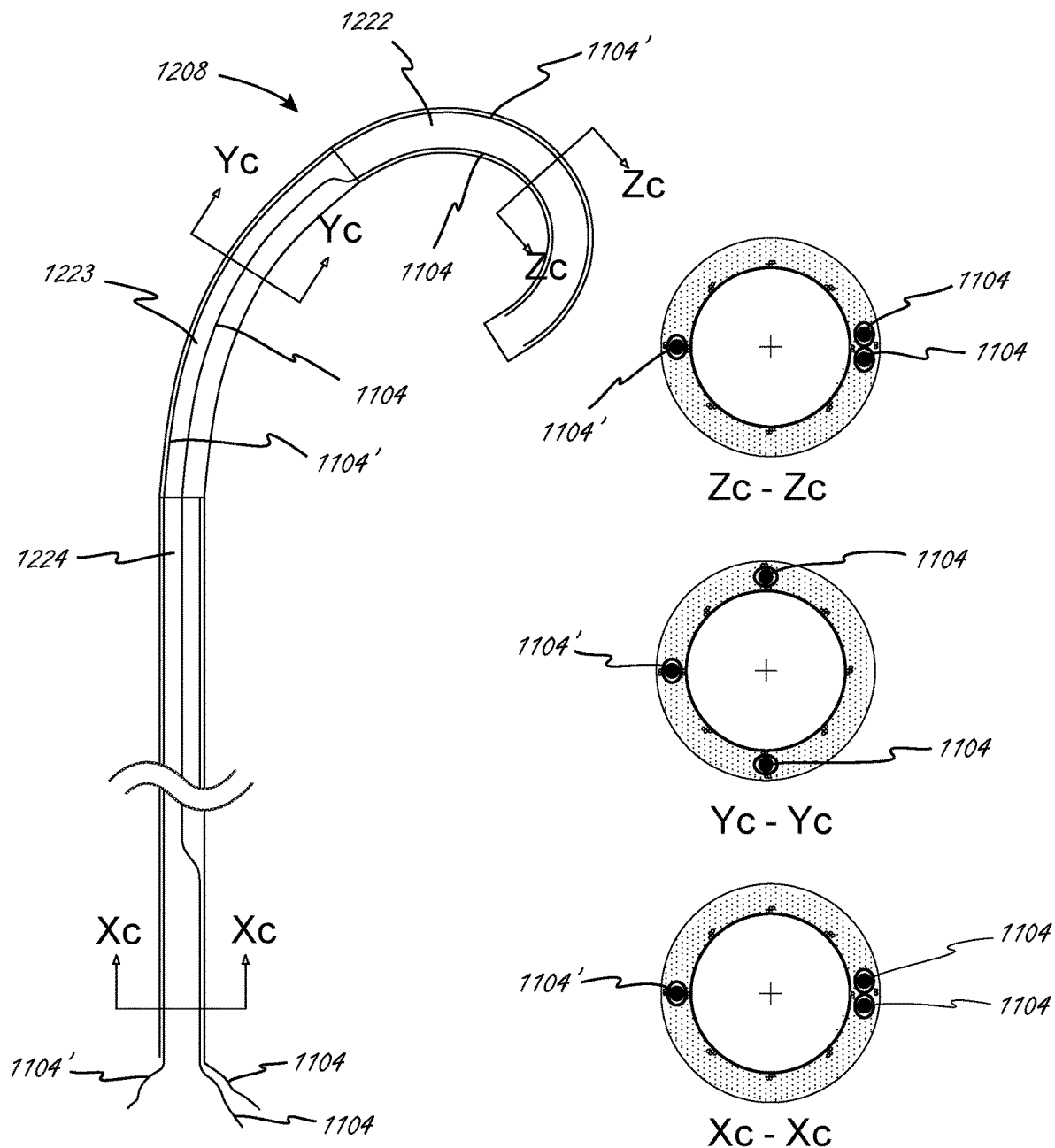
FIGS. 7Ci and 7Cii illustrate an exemplary steerable shaft with pull wires.
Figure 7E:
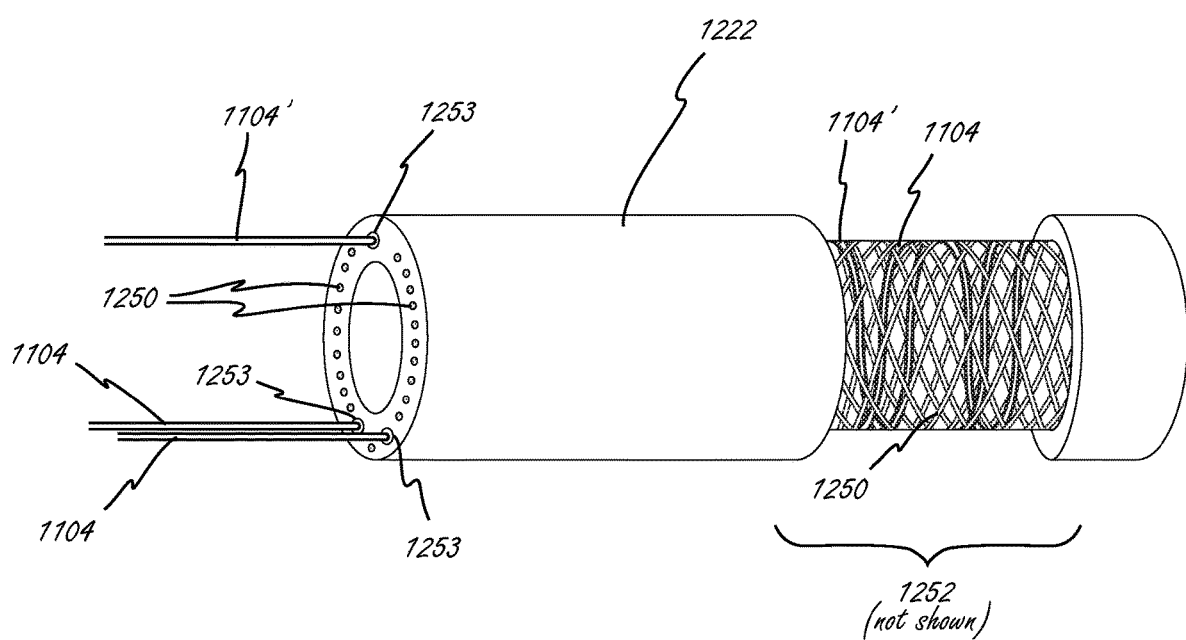
FIG. 7E illustrates an exemplary steerable shaft with one or more pull wires circumferentially interwoven into braid wires of the shaft.

During use, a portion 1223 of the distal catheter just proximal to the steerable (deflectable) portion 1222 may be forced to conform to a curve based on the constraints of the anatomy in which it is used. For a specific embodiment where the device is advanced into the heart chambers from a groin access, the portion 1223 forced into a curve is expected to range from 5 to 25 cm in length. During rotation of the sheath shaft 1208 from the proximal end, torque is transmitted through this distal curved region 1223 to the catheter tip. A non-uniform cross section and/or tension of the device in this region 1223 may induce a tendency for the shaft to build up and suddenly release torque, causing a "whip" or sudden jerk in rotation as it is torqued. To minimize the potential for whip, it is optional to distribute the pull wire tension and construction material around the surface of the curved region 1223. In one embodiment, such as is illustrated in FIG. 7Bi-iii, the pull wire 1104 may spiral around the central axis of the sheath in at least the curved region 1223 proximal to portion 1222. The pull wire of this embodiment may make a full circumferential wrap over approximately 10 cm of length, with this value ranging 5-15 cm. The spiral may only need to be present in the curved region 1223, continuing straight proximally thereafter through proximal portion 1224 (similar to 1006), which may minimize the friction in the pull wire lumen and the associated pull wire force required to steer (deflect) the steerable portion 1222. The spiral may also make a minimum of one turn before continuing straight, or spiral the full length of the shaft. In another embodiment to minimize whip, it may only be necessary to distribute the pull wire tension to opposite sides of the shaft. As illustrated in FIG. 7Ci-ii, deflection of the steerable section 1222 is accomplished with two parallel pull wires 1104 positioned adjacent one another on the same side of the sheath 1208. In the curved region 1223 and proximal portion 1224 (similar to 1006) proximal to the steerable section 1222, the pull wires are routed to opposite sides of the shaft, each 90° from the position in the steerable section 1222, to distribute the tension more evenly. While it is preferable to actuate the two parallel pull wires at the same time with equal force with the handle actuator, in other embodiments, a differential in force could be applied to steer the tip to one side or the other of the plane formed when the two are actuated with equal force. In other embodiments, any plurality of pull wires could be routed in the same configuration as illustrated in FIGS. 7B or FIG. 7C, with the multiple proximal pull wires distributed uniformly around the shaft circumference. Also, as illustrated in FIG. 7Ci-ii, the pull wires 1104 may be routed proximally along the opposite sides of the shaft for most of the shaft proximal portion 1124 length, but preferably brought back together adjacent one another near the proximal end portion of the shaft to allow the wires to exit the same side of the proximal shaft together to facilitate them being secured together to a handle component for simultaneous actuation tension.

FIGS. 7Di-iv illustrate another embodiment of the distal region of catheter with construction similar to that previously described, but instead configured to provide a distal steerable portion 1222 which can be deflected into two different directions. As illustrated, a two pairs of pull wires 1105/1107 and 1106/1108 are along the proximal shaft region 1224 and curved region 1223. This is similar to FIG. 7Ai-iii, except that the wires are paired on each side of the shaft. The routing could also be spiraled as in FIG. 7Bi-ii, or other configurations discussed. Within distal steerable portion 1222, the wires are routed 90° from the proximal portions, although other angles are contemplated. At a junction 1225 within 1222 one or more of the pull wires (e.g., 1105 and 1107) may be terminated and anchored to the shaft, with the remaining pull wires (e.g., 1106 and 1108) continuing to a more distal tip location 1226 where they are anchored. This configuration allows independent actuation of pull wires terminated at 1225 and 1226 such that different shapes may be created during actuation. FIG. 7Dii shows both lines 1107 and 1108 tensioned to create a variable curve in the same direction. FIG. 7Diii shows lines 1107 and 1106 tensioned to create an "S" curve. Other configurations are also possible.

The pull wires (such as 1104 and 1104') must be terminated at their distal end in a manner that reliably affixes them to the wall of the distal steerable shaft portion 1222, such that they do not break or pull free under repeated applications of tension. In a preferred embodiment, shown in FIG. 7E, the pull wires 1104 and 1104', upon exiting the distal pull wire lumen 1253, are circumferentially interwoven into the braid wires 1250 of the distal shaft 1222 (shown without the thermoplastic polymer 1252). One or more of the pull wires 1104 or 1104' may also be additionally or instead wrapped and/or tied around the outside of the braid wires 1250 for additional securing. The braid wires 1250 may be then trimmed distal to the securing point, with the interwoven and/or wrapped pull wires preventing the braid wires from expanding and/or unraveling. Additional adhesives such as UV cured or cyanoacrylates may also be used to secure the pull wires to the braid wires. The weave and/or wrap of the pull wires and braid wires is then laminated with a thermoplastic polymer which melts within the space around the wires and cools to secure them in place. The thermoplastic polymer may also have radiopaque compounds that include materials such as bismuth, barium sulfate, or tungsten in order that the tip of the sheath be visible to the user under fluoroscopy.

In additional embodiments, the tool 1212 may also or alternatively be constructed with one or more pull wires to deflect the tip in a manner similar to any of the previous embodiments described for the outer sheath 1208. In addition to routing the pull wires within the wall of the tubular member of the tool 1212, the pull wires could be routed next to the conductors inside the lumen of the tubular element 1212. Actuation of the pull wires could be from an actuator located in the proximal handle 1206. The distal shaft of tool 1212 may also be formed into a particular shape (e.g., an arc) such that it bends into the shape as it exits the tip of the steerable portion 1222 of outer sheath 1208. The stiffness of the distal shaft of tool 1212 is such that it does not substantially deform outer sheath 1208 while inside, but upon exiting is allowed to bend. The shape may be set by any one or combination of the following means: heat setting the polymeric material, using a moveable or fixed shaped stylet within the inner lumen of shaft 1212 or within a lumen within the wall of shaft 1212. Such a stylet could be round, oval, or rectangular in cross section, and be formed of stainless steel, nitinol, or a rigid polymer such as PEEK, Vestamid, or similar. The outer steerable sheath could alternatively be made to bend with a similar method as above, with or without additional pull wire deflection, and with or without additional shape or deflection of the distal portion of tool shaft 1212.

Figure 8:
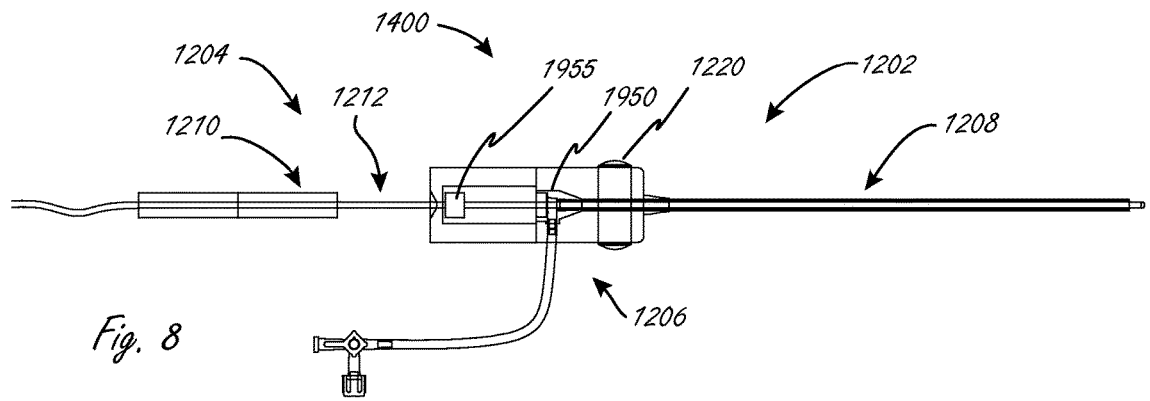
FIG. 8 illustrates an exemplary system comprising a medical tool inside a steerable sheath or shaft, designed to have modular components that are provided to the user in an integrated manner.

FIG. 8 illustrates a system 1400 comprising a medical tool 1204 disposed partially inside a steerable sheath 1202. Medical tool 1204 and sheath 1202 can be any of the medical tools and sheaths described herein, even though they are labeled 1204 and 1202. While the steerable sheath 1202 is preferably "steerable", for example through the use of a pull wire or other functional deflection mechanisms (any of those set forth herein), it is understood that this "steerable" sheath (or any steerable sheath herein) could also be non-steerable in that it is just a straight tubular element, or has a fixed, non-deflectable distal curve shape. Steering may be also accomplished via torqueing the sheath, with or without use of a deflection mechanism.

The system 1400 illustrated in FIG. 8 is designed to have modular components that are provided to the user in an integrated manner, but which can be disassembled after a procedure using a specialized process to clean, repair, and/or replace any of the modular components of the system. The system 1400 may then also be reassembled, sterilized and repackaged. This process, or in some cases a portion of this process, can be referred to herein as "reposing," or "refurbishment," and any system herein can be reposed or refurbished using any of the methods herein. The performance of system 1400 is optimized for the medical tool 1204 and sheath 1202 to work only with one another and not substitute other devices on the market that may have a similar function. Also, the reposing of the devices takes special care to ensure the continued safety and performance quality of the system.

In the disclosures that follow, many references are made to ways of separating various modular components of a system, either by breaking or using a controlled process. Depending on the embodiment, handle portion 1960 (see FIGS. 9A and 9B), rear handle 1961 (see FIG. 11), and handle lip 1962 (see FIG. 12A) can be separated from the handle assembly. Tool lock 1955 (e.g., shaft 1240 shown in FIGS. 42 and 43), for example, can be separated from tool portion 1212 of medical tool 1204 or from handle assembly 1206. Tool connector 1210 (see FIG. 8) or 1990 (see FIG. 13A), for example, could be separated from tool portion 1212. Hemostasis valve 1950 assembly (see FIG. 8) could be separated from the handle assembly 1206. Sheath portion 1208 could be separated from handle assembly 1206. Outer member 2010 (see FIG. 17B) of tool portion 1212 could be separated from inner lead assembly 2011 and its internal electrical connections. Many similar controlled processes and materials could be used to enable the initial assembly and subsequent disassembly and reassembly of the components of any of the embodiments herein.

Any given process or combination of processes could be used at any one or all the aforementioned modular separation points. The processes include but are not limited to the following examples. Components could be bonded using a material that acts like an adhesive or mechanical lock, but which can be deformed with heat to remove the components. This includes materials such as wax and thermoplastic elastomers (polyurethane, polyethylene, polyamide, to name just a few). Materials such as hydrogels (such as those described previously herein) may be swollen with aqueous solutions to change their properties such that they soften or become lubricious enough to separate components. Sugar, salt, starch, or other similar materials in crystal or powder form could be used to create a mechanical interference fit between components, but then readily dissolved in an aqueous solution to separate the components. These materials could also be used as a matrix in a non-degradable material that then compresses like a foam once the crystalline structure is dissolved. Other polymers known to break down over time after contact with fluid (such as that introduced during use), including those also known in the art to be biodegradable, could be used in the system such that replacement due to their weakened properties would be mandated. Other materials could be used that lose their holding strength in the presence of a chemical solvent. Strong acids or bases could be used to dissolve certain metals and plastics. For example, silicone may swell and tear easily in the presence of heptane, hexane, or isopropyl alcohol. Where a liquid material is to be dispensed to alter the seal, the seal could be protected during use inside a protective space which can only be accessed with a special tool (such as a needle puncture diaphragm or luer activated valve).

Certain components may be joined using a solder or solder-like process, where reheating the solder will separate the components. In some embodiments the metallic joint could be separated using electrolysis. Mechanical interference could also be used to hold components together (e.g., screws, pins, thread, wedge, and the like). Ratcheting mechanisms (e.g., Zip-ties, belt-loop styles, roller-wedge, cam-actuated grips) could also be used to hold components together but require a manufacturer access to the parts to break and replace or use a tool to temporarily separate the components. Components could be held in place through magnetic attraction (magnet to magnet or magnet to iron). In particular embodiments, the magnetic hold could not be released without demagnetizing the magnets. This could be accomplished by physical breaking or mechanically fatiguing the magnet, raising the temperature of the magnet above its Curie Point (e.g., 80° C. for neodymium magnets), or applying an alternating current across the magnet to disrupt the dipoles. In another embodiment, parts could be engaged and held in place with a lock such as a bar fit into a hole or other capture feature (similar to a door lock). The bar could be heat set in a curve, or a hinge structure, that is normally engaged in the hole, but upon exposure to heat beyond a transition temperature, changes shape to back out of the hole (allowing parts to be disassembled). In a similar manner, the bar could be magnetized and when exposed to a magnetic field, forced out of the hole. Other similar mechanisms could use coils or other springs, or spring-actuated devices, which change shape in the presence of heat or a magnetic field to unlock. In another embodiment, components could be held together under hydraulic pressure (e.g., water or oil such as mineral oil or silicone oil), such as a sealed cylinder with a piston, a bellows, diaphragm, balloon, etc. To separate the components, the pressure may be vented by puncturing into or otherwise breaking the seal to the pressurized chamber. Opening or relaxing a valve to relieve the pressure could also be employed. In many cases, the process used to separate the parts will also contaminate or damage them enough to require replacement, further repair, and/or additional cleaning before reassembly and other subsequent processing steps. Any combination of the exemplary processes above could also be used.

In any of the embodiments herein, a medical tool can be an ultrasound device, with one or more ultrasound transducers disposed at its distal region. For example, the ultrasound device may be an ultrasound imaging device, such as a 4D-ICE (intracardiac echocardiography) imaging tool.

FIG. 8 illustrates that tool portion 1212 of the medical tool 1204 may be rotatable within and relative to steerable sheath 1202 and may also be optionally capable of axial translation within the sheath. Tool lock 1955, which in FIG. 8 is disposed within the body of handle 1206, is secured to tool portion 1212 and may have one or more functions to constrain movement within sheath 1202 and/or control the functionality of medical tool 1204 (e.g., shaft 1240 in FIGS. 42 and 43). In some embodiments of constraining the axial motion of tool 1212 in the proximal direction, the tip of the tool 1212 may be prevented from entering inside the sheath where it may be rendered non-functional (e.g., if the purpose is to deliver electrical energy to the tissue or send/receive ultrasound pulses). In other embodiments, a luminal seal may be provided on tool 1212 just proximal to the functional portion of the distal working end, which when retracted into a particular location within the distal luminal space of sheath 1208, defined by the proximal retraction limit, a seal within the lumen is formed. In other embodiments where the distal end region of tool 1212 is larger than the ID of the sheath, as is illustrated with tip 1821 in FIG. 13A, the proximal limit may prevent damage to the sheath, other devices, or tissue if the tool tip is retracted against the distal tip of the sheath portion 1208. The proximal travel limit of tool 1212 provides a slight offset (e.g., 0.5-3.0 mm) between the proximal end of tip 1821 and the distal end of sheath portion 1208, which may be beneficial to allow space for flushed fluids to the exit the sheath lumen and/or avoid pinching tissue structures or interventional devices between the tip 1821 and sheath 1208 when the tip is pulled back close to the distal end of the sheath 1208.

Constraint of axial motion of the tool 1212 in the distal direction may be necessary to ensure adequate control of the tool 1212. For example, too far of an extension without distal steering may cause inadvertent damage to tissue structures by the user, or the tool 1212 could become too floppy to torque and steer with adequate precision using the system 1200, limiting its performance. The use of a tool lock 1955, constrained within the handle 1206, to limit axial motion will also have practical limits for the length of handle 1206. With the above considerations in mind, an optional practical distal extension limit of the tool 1212 created by the interaction of tool lock 1955 in handle 1206 would be approximately 3 cm. Other embodiments could be considered up to 5 cm tool extension. Other configurations with an extension of up to 20 cm to leverage advantages of a floppy tool shaft, or pre-shaped steerable tool shaft, or a deflectable tool shaft, to track into various anatomic structures are also contemplated. The elimination of a travel limiter such as tool lock 1955 would limit travel by the length of the tool shaft that has sufficient clearance to pass within the lumen of sheath portion 1208. FIG. 8 also illustrates a hemostasis valve assembly 1950 within the handle portion 1206 which is useful to keep blood or other fluids from leaking out from the proximal end of steerable sheath 1202, and to allow flushing of the luminal space between tool 1204 and the inner lumen of sheath 1202.

Figure 9A:
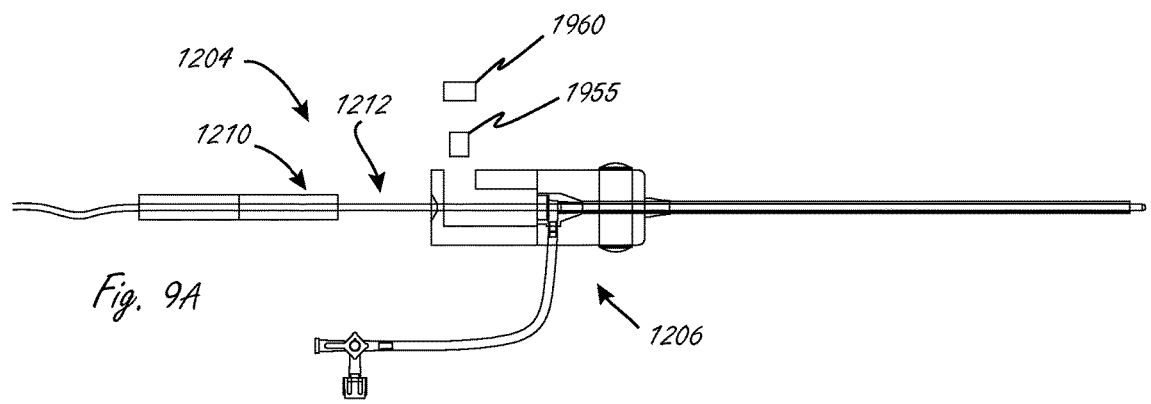
FIGS. 9A and 9B illustrate an embodiment where a sheath handle includes a removable or breakable handle portion.
Figure 9B:
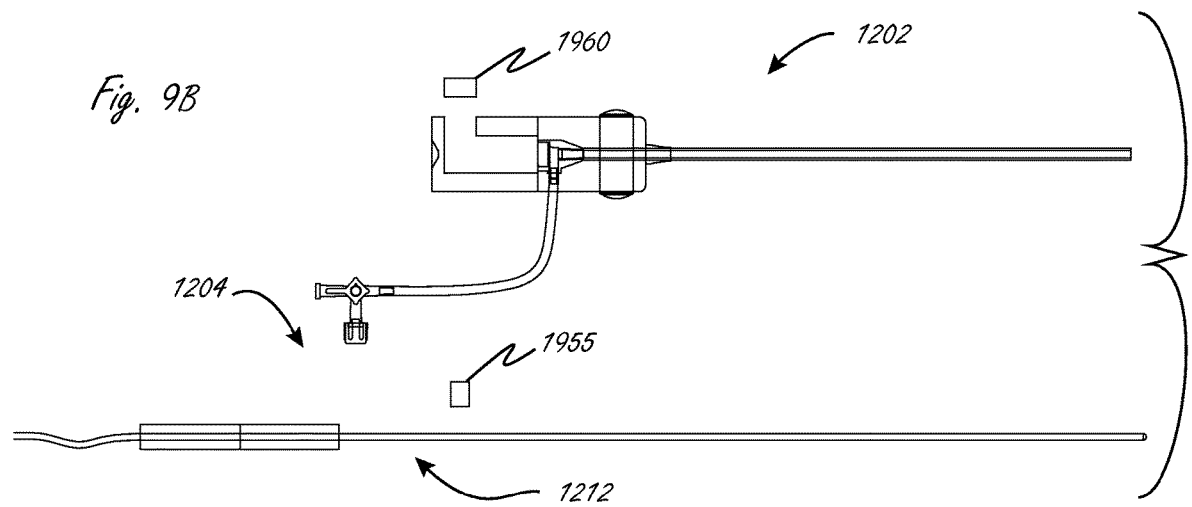

FIGS. 9A and 9B illustrate another embodiment of a system where handle assembly 1206 includes a removable or breakable handle portion 1960 that can be removed from handle assembly 1206 or broken from assembly 1206 to allow access to an interior space of handle assembly 1206. Once removed or broken, as shown in FIG. 9A, access is available to tool lock 1955 disposed with handle assembly 1206. Tool lock 1955 can then be disassociated from tool portion 1212, as shown in FIG. 8A. Once tool lock 1955 is removed, tool 1204 is can then be removed from sheath 1202, as shown in FIG. 9B.

In some embodiments, handle portion 1960 (and any other handle portion herein that can be removed or broken from a handle assembly) can be configured to interface with a corresponding component of handle assembly 1206 so that it can be stabilized relative to 1206 when in use, but can be removed from handle 1206 in a controlled manner without breaking an interface between handle 1206 and portion 1960. For example without limitation, the two parts could have a threaded interface. Alternatively, for example, portion 1960 can be configured so that the interface between it and handle assembly 1206 must be broken, but wherein the interface is such that breaking it can be done in a relatively easy and predictable manner.

One function of tool lock 1955 is to prevent removal of the medical tool 1204 from sheath 1202 to ensure system integrity as previously stated. A tool lock also limits the axial translation of the medical tool within the handle assembly by being physically constrained within the handle assembly. This may be desirable to ensure the medical tool is either not moved axially, or the movement is constrained to a safe and functional range for the medical tool beyond the tip of the sheath.

In another embodiment, illustrated in FIGS. 10A and 10B, tool lock 1955 and handle assembly 1206 may both be configured to limit the range of medical tool rotation. This may be desirable to prevent a build-up of torque in one direction that could twist and damage portions of the outer member 2010 or an inner lead assembly 2011 (see FIGS. 17A-C).

As illustrated in FIGS. 10A and 10B, tool lock 1955 has a feature 1956, in this embodiment a radial protrusion on one side, that allows it to be rotated through an angle less than 360° in either direction. Handle assembly 1206 has a protrusion (disposed at the bottom of the figure) extending radially inward that is positioned and configured to engage with and stop movement of feature 1956, and thus tool lock 1955 and medical tool 1212. Other torque limiters known in the art, including those that limit torque to a finite number of full rotations in a given direction, could also be employed. Axial travel and torque could also be limited by opposing magnets. Resistance would be encountered as a magnet in a tool lock approached (via axial or rotational travel), an opposing magnet positioned in the handle portion. Rotational limitation, an illustration of which is shown FIGS. 10A and 10B, can be incorporated into any of the systems herein.

FIGS. 42 and 43 illustrate an alternate exemplary medical tool rotation limiting mechanism in the handle. In that embodiment, the rotation limiter is a compound rotation limiter, is also disposed proximal to a hemostatic valve, and allows for greater than 360 degree rotation of the medical tool shaft at the location of the rotation limiter within the handle.

In embodiments that include a tool lock, the tool lock rotational and/or axial movement may also have a friction fit with features within the handle such that it is moveable but does not rotate or slide back to the original position except by action of the user. For example, either or both the outer surface of the tool lock and an inner surface of the handle portion (such as handle portion 1960) may comprise a lubricious material such as PTFE, FEP, Delrin (Acetal). Unless formed from the same material, the mating material could be a smooth polished polymer or metal. The two parts could have a precise clearance or interference of, for example, up to 0.0002". The friction could also be controlled by a slight interference from just a portion of the surface of the tool lock with a portion of the handle portion (such as portion 1960). The interference could be a small integrated feature, and/or or a separate component which is mounted on an elastic material such as a compressible polymer (silicone, polyurethane, etc.), either solid or in foam form, or a metal or rigid polymer spring formed from a coil or flat ribbon. A slidable wedge could also be used to adjust the compression. The amount of compression interference could also be adjusted at the time of manufacture with a lead screw or a pressurized chamber driving the interference features together. During a reposing process this compression friction interference would need to be disassembled, and then reassembled and returned to manufacturer settings. In another embodiment, the compressive features could be assembled into the handle portion (such as portion 1960) to act directly on the tool portion 1212 without the need for the tool lock feature. While the tool lock is illustrated as integrated into tool portion 1212, it could also be integrated directly in to the tool handle portion 1210, which would be engaged into the sheath handle portion 1960. This is particularly applicable where axial translation of the medical tool 1204 relative to the sheath 1202 is not required.

Tool lock 1955 may also have an electronic or electromagnetic feature which senses the presence of handle portion 1960 (or other handle portion). Once a handle portion (e.g., portion 1960) is removed, the tool lock may disable the functionality of medical tool 1204. For example, the handle portion may include a magnet mounted in proximity to the tool lock. The magnet can hold a reed switch closed in the tool lock that completes a functional circuit in the medical tool. When the magnet is removed with the handle portion (e.g., portion 1960), the reed switch opens and disables the medical tool. Other proximity switches to accomplish the same function can also be used. The tool lock may also or alternatively disable the medical tool function once the tool lock is removed from the medical tool (e.g., as would be required to remove the medical tool from the sheath). For example, the tool lock could have a direct wired connection to the medical tool (for example, within the tool portion 1212) which disconnects from the medical tool upon tool removal. The medical tool could also include a proximity sensor in the tool portion 1212 which is disabled once the medical tool is removed from the sheath. For example, similar to that described above, a reed switch completing a functional circuit in the medical tool could be held closed by a magnet in the tool lock. Removal of the tool lock would then open the reed switch and disable the medical tool. Other proximity sensors known in the art could also be utilized. Replacement of the tool lock could re-enable the function; however, an additional reprogramming of the controlling tool software may also be made necessary to reset function of the medical tool once the software detects an interruption in the circuit. In a related scenario, the removal or breakage of handle portion (such as portion 1960) could interrupt a circuit in the tool lock which is sensed by the medical tool and/or more specifically, the controlling tool software. Function could then be restored to the tool by repairing, replacing, or reprogramming the tool lock, and the replacement and/or repair of the handle portion (such as portion 1960).

FIGS. 11A and 11B illustrate another embodiment of a system that has modular features to aid in reposing the device. In this embodiment, handle assembly 1506 may be disassembled through removal or breakage of handle rear component 1961 from the remainder of handle assembly 1506. This allows access to a tool lock (not shown but it could any tool lock described herein) as well as hemostasis valve assembly 1950. Depending on the configuration of the tool handle, the handle rear 1961 may be removed from the tool in the proximal direction (without removal of the tool lock), or the tool lock may be accessed more easily to remove the tool lock than the prior embodiment where only the handle portion 1955 was removed. In the present configuration hemostasis valve assembly 1950 may be accessed to remove and replace the valve assembly. Alternatively the valve assembly, including any of its individual components, could be removed, disassembled, cleaned, repaired, and replaced. Repair may only involve replacement of hemostasis seal 1951 in the assembly 1950. The seal could be of a slitted silicone or other soft polymeric compound known in the art, or any of the seals in this disclosure. The hemostasis valve assembly preferably includes a luer fitting 1952 on its distal end such that it could simply be pressed into and out of a mating luer fitting in the handle. Alternative fittings can also be used.

The steerable sheath 1202 may also be adapted to allow the sheath portion 1208 to be separated from the handle assembly 1506. Similar to other modular components, this could allow removal for cleaning, repair, or replacement. Sheath 1202 may be fitted with tensile elements to deflect the catheter tip. Tensile elements similar to these are illustrated in FIG. 11B as elements 1970. The one or more tensile elements 1970 are preferably secured permanently to a fastener 1971, such as by a welding, soldering, crimping, swaging, or adhesive/epoxy bonding process. If potting the ends in an adhesive/epoxy, the end of the tensile element is preferably formed into an enlarged ball, coil, loop, or other similar feature larger than the cross-section of the tensile element itself. Alternatively, the tensile element may be releasably secured with a set screw or other mechanical fastener. An enlarged welded ball end or a separate tube crimped to the proximal end of the tensile element may aid in mechanical capture of the tensile element 1970 in the fastener 1971. The fastener 1971 is configured to be acted on by an engagement feature 1972 and linked to the steerable actuator 1520. The engagement feature 1972 comprises a portion 1972' and 1972" each comprising a thread, one the reverse of the other. The actuator 1520 comprises a dual thread, one the reverse of the other, such that when actuator 1520 is rotated, portions 1972' and 1972" of the engagement feature are driven in opposite directions thereby causing the steerable section to deflect in one or another direction. The fastener may be designed to be readily disconnected and reconnected to the actuator for rapid and cost-effective processing during reposing. Alternatively, the tensile elements may be removably connected directly to the engagement feature without use of the fastener.

FIGS. 12A and 12B illustrate an alternative embodiment of an integrated medical device (e.g., ultrasound) or system 1700 that includes an integrated handle assembly, a steerable sheath, and a medical tool, and can be repurposed using any of the methods herein. In system 1700, the handle assembly 1703 is in operable communication with steerable sheath 1702 and medical tool 1704, the handle assembly 1703 including a handle body 1705 with an outer surface positioned to be gripped by a user, a first actuator 1720 adapted to be moved relative to handle body 1705, and a second actuator 1780 adapted to be moved relative to handle body 1705. Steerable sheath 1702 has a distal deflectable region (not labeled) that is in operable communication with at least one pull wire. In some embodiments, medical tool 1704 is an elongate ultrasound device with a distal portion that comprises an ultrasound transducer, at least a portion of the elongate ultrasound device is disposed within steerable sheath 1702, the elongate ultrasound device is in operable communication with second actuator 1780. First actuator 1720 is in operable communication with at least one pull wire such that actuation of first actuator 1720 relative to handle body 1705 causes deflection of the distal deflectable region of steerable sheath 1702.

Second actuator 1780 is adapted to be rotated relative to handle body 1705 and is also adapted to be moved axially relative to handle body 1705. Second actuator 1780 is in operable communication with the elongate medical device 1704 such that axial movement of the second actuator 1780 relative to handle body 1705 causes axial movement of elongate medical device 1704 (distal and proximal) relative to the distal end of the steerable sheath, and such that rotation of second actuator 1780 relative to the handle body 1705 causes rotation of elongate medical device 1704 relative to the distal end of the steerable sheath, as is shown as rotational movement "R" in FIGS. 12A and 12B.

Axial movement of the tool relative to the sheath, if the tool is an ultrasound imaging tool, is generally desirable in that it improves the probe's ability to image larger regions of the body after the probe has been steered to a particular location and allows the operator to more easily refine the field of view once the probe has been steered to a generally viable location.

System 1700 also includes optional tool lock 1755. Tool lock 1755 is contained within handle assembly 1703 but coupled to second actuator 1780. Tool lock 1755 and second actuator 1780 may be fitted with magnets, for example, to engage one another. Alternatively, one of the components could contain iron and the other a magnet. Tool lock 1755 is firmly and releasably coupled to tool portion 1712 of medical tool 1704. Advancing distally or retracting proximally second actuator 1780 moves tool lock 1755 distally or proximally, respectively. The resulting axially movement of actuator tool 1755 causes axially movement of medical tool 1704. Similarly, rotation of second actuator 1780 relative to handle body 1705 causes rotation of tool lock 1755, which causes the rotation of medical tool 1704 (shown as rotation "R" in FIGS. 12A and 12B). In this embodiment, the tool's axial movement (relative to the sheath) as well as its rotational movement (relative to the sheath) are limited within a fixed range of motion. In one embodiment, in order to remove medical tool 1704 from the steerable sheath 1702 (such as during refurbishment), handle rear lip 1762 could be removed or broken to remove tool lock 1755 (and remainder of the tool portion 1712) from handle 1706. In addition, second actuator 1780 could be decoupled from tool lock 1755. This may require custom fixtures to pry the coupled units apart, or the use of a special tool to demagnetize or otherwise alter the polarity (temporarily at least) of either the outer coupler or tool lock. As described previously, the tool lock may contain a feature to disable the tool function when the magnet or other proximity controller is removed. Rear lip 1762 is an illustrative and optional component, and the handle assembly can have different parts.

FIGS. 13Ai-ii-13C illustrate an embodiment of a system in which the medical tool 1204 (which can also be any other medical tool herein) includes a plurality of electrical contacts 1992. FIGS. 13Ai and 13Aii illustrate the disassembled components. FIGS. 13Bi and 13Bii illustrate tool portion 1212 back loaded into the sheath portion 1208. FIG. 13C illustrates proximal tool connector 1990 (which can be attached, directly or indirectly with an energy console) connected to tool portion 1212 so the tool portion 1212 is in electrical communication with connector 1990. Tool portion 1212 is fitted on the proximal end with a plurality of mating electrical contacts 1992. Tool 1204 contains a distal working end 1821 (e.g., ultrasound imaging tool) which is larger in diameter than the lumen of the tool portion 1212, an illustration of which is shown in FIG. 13Bii. In this embodiment the outer dimension of tool portion 1212 and electrical contacts 1992 are sized to pass through a lumen of the sheath portion 1208, but the distal working end 1821 is too large to pass through the lumen. As a result, assembly of the tool through the sheath portion 1208 requires the proximal end of the tool portion 1212 be advanced through the distal tip of the sheath and advanced proximally until the electrodes exit the proximal end of the sheath handle 1206. This construction helps minimize the outer dimension of the sheath portion 1208 such that it is not necessarily larger than the distal working end 1821. In certain uses the distal working end may need to be at a maximum allowed dimension to accommodate electronic components and their connections, or, in certain applications, minimize the density of electrical current or acoustic energy to minimize overheating or cavitation of the tissue. The proximal electrical contacts 1992 may be discrete electrically conductive surfaces (e.g., discs, bars, strips, spheres, etc.), or circumferential or partially circumferential rings. In a preferred embodiment, the contacts are formed from the exposed conductive material of an otherwise insulated flex circuit (e.g. insulation is not disposed over the exposed conductive material). The mating contacts 1991 in the connector may be similarly designed to make contact. The contact surface may be annular or flat and preferably is spring loaded or otherwise mechanically compressed to make secure contact. The handle assembly in FIGS. 13A-3C can be any of the handle assemblies herein; the steerable sheath can be any of the steerable sheaths herein; and the medical tool can be any of the medical tools herein. The front loading assembly can be used during the assembly of any system herein.

FIGS. 14A-14C illustrate an exemplary proximal portion of a system, and which can be the proximal portion of any of the systems herein. As illustrated in FIG. 14A, proximal contacts 1992 of the medical tool may be press fit into connector 1990 against the contacts 1991. Alternatively, as illustrated in FIG. 14B, connector 1990' can be adapted to open up to receive contacts 1991 before it is clamped down over contacts 1991, as shown in the closed configuration of FIG. 14C. The connector 1990' can be sealed with seal 1995 during manufacture. Seal 1995 may comprise, but is not limited to, a hydrogel, a wax, a silicone ring or gasket, or other means and combinations described previously in this disclosure. To repose the device, the connector 1990' contact must be broken or carefully disassembled to remove the shaft of tool 1212 in the distal direction through the sheath (such as a steerable sheath). Disassembly of seal 1995 may be accomplished by heating and melting the wax or other meltable substance, dissolving a dried material in an aqueous solution, and/or swelling a silicone with heptane or similar chemical compound.

FIGS. 15A-15B illustrate an exemplary system similar to that of FIGS. 14A-14C with the exception that the connector 1990" contains an inner feature 2000 designed to stably interface with and enclose tool lock 1955 attached to tool portion 1212. FIG. 15A illustrates the system just before connection of the connector 1990" to the tool portion 1212, and FIG. 15B shows a completed connection. While tool lock 1955 is illustrated just distal to the proximal tool contacts 1992, it could also be configured on the proximal side of the contacts, with a corresponding inner feature 2000 location proximal to the connector contacts 1991. As described previously, the tool lock may contain a feature to disable the tool function when the magnet or other proximity controller is removed. In this embodiment, the disabling feature may alternatively be built into the connector 1990", particularly within the inner feature 2000, where the circuit connection in the cable leading back to a control console is dependent on the state of the disabling feature. Assembly and disassembly of the portion of the connector containing feature 2000 could be accomplished by the means described previously for the connector 1990 in FIG. 15, the handle portion of FIG. 9, or the rear handle of FIG. 11. The handle assembly in FIGS. 15A-B can be any of the handle assemblies herein; the steerable sheath can be any of the steerable sheaths herein; and the medical tool can be any of the medical tools herein.

In a variation of the embodiment in FIGS. 15A and 15B, the assembly of tool 1212 may require the "back loading" of tool 1212 through the distal end of the steerable sheath portion 1208, as described in the embodiment of FIGS. 13A-13C wherein the outer dimension of the tool and the electrical contacts are sized to pass through the lumen of the sheath portion, but the distal working end may not pass. In this embodiment of FIGS. 15A and 15B, the tool lock must be assembled after back loading the tool. During reposing, the tool lock would need to be removed to remove the tool 1212 from the sheath portion 1208, and repaired and/or replaced after cleaning and re-back loading the tool 1212 through the sheath portion 1208. In an alternate version of the embodiment, the tool 1212 may be assembled by "front loading" an insertion of the distal tip through the proximal handle end of sheath 1202. In this alternate embodiment of FIGS. 15A and 15B, tool lock 1955 does not necessarily need to be removable from the tool 1212.

As illustrated in FIGS. 15A-B, the clamping action of inner feature 2000 over tool lock 1955 results in a mechanical engagement of the two features such that axial translation and torque may be transferred from the connector 1990" to the tool 1212. This may provide the user with a more convenient means of gripping the tool 1212 to manipulate its position relative to the sheath 1202.

Figure 16:
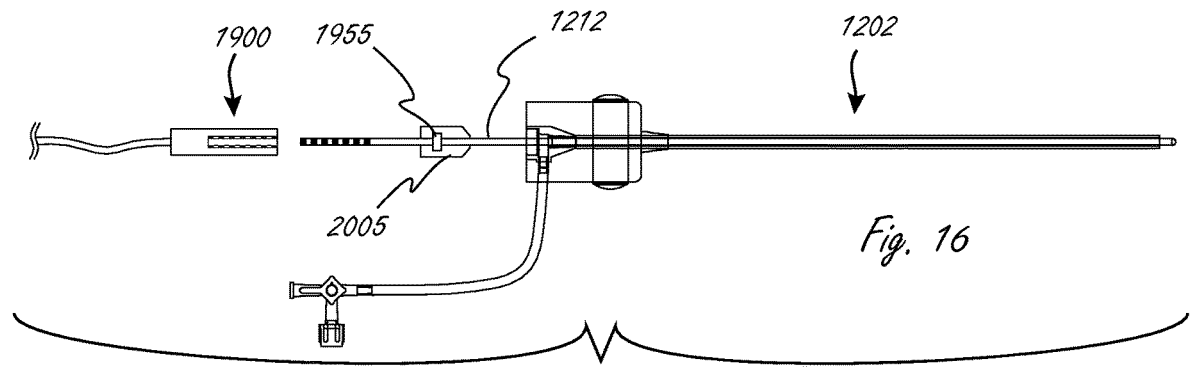
FIG. 16 illustrates an exemplary system that includes a separate medical tool torque device that could be attached to a medical tool to provide an ability to translate and torque the tool relative to a steerable sheath.

As illustrated in the exemplary system of FIG. 16, a separate torque device 2005 can be attached to the tool 1212 to provide a similar ability as above to translate and torque the tool 1212 relative to sheath 1202, but without the need to make a connection to connector 1990, as previously described in FIGS. 15A and 15B. The torque device 2005 may also be engaged over tool lock 1955 to provide enhanced mechanical engagement. Torque device 2005 could also serve a purpose similar to the inner feature 2000 in that tool function is dependent on the presence of the torque device 2005. As previously described in the embodiment of FIGS. 13A-13C, the torque device could be assembled onto the tool 1212 such that removal of the tool 1212 from the sheath 1202 is not possible without breaking the torque device and/or tool 1212, or without the use of a custom reposing process to remove the torque device. The handle assembly in FIG. 16 can be any of the handle assemblies herein; the steerable sheath can be any of the steerable sheaths herein; and the medical tool can be any of the medical tools herein.

Figure 17A:
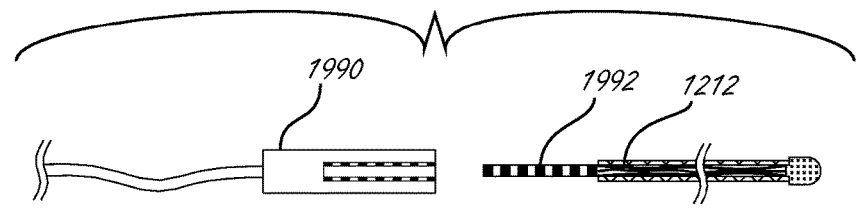
FIGS. 17A, 17B and 17C illustrate an exemplary tool that comprises an outer member and an inner lead assembly.
Figure 17B:
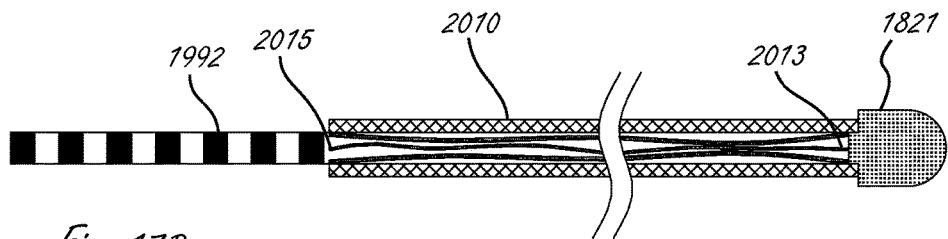
Figure 17C:
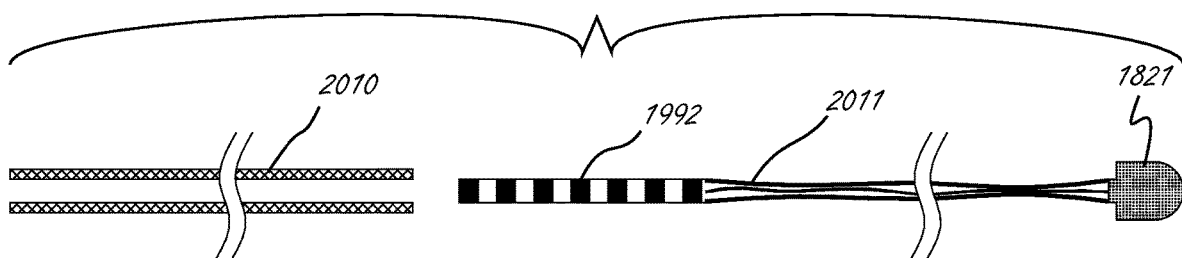

The embodiment of FIGS. 17A-C illustrates an exemplary medical tool where tool portion 1212 comprises an outer member 2010 and an inner lead assembly 2011. The inner lead assembly further includes a distal working end 1821 and proximal electrical contacts 1992. The outer member 2010 may be assembled and disassembled from the inner lead assembly as part of the reposing process. The outer member 2010 can be a tubular structure capable of transmitting torque via, for example, a braided composite construction. Outer member 2010 is reversibly sealed and secured to the inner lead assembly at locations 2015 and 2013 using processes previously described in this disclosure. FIG. 17B shows a larger view of the encircled region in FIG. 17A. FIG. 17C shows inner lead assembly 2011, distal working end, and proximal end removed from outer member 2010. The handle assembly in FIGS. 17A-C can be any of the handle assemblies herein; the steerable sheath can be any of the steerable sheaths herein; and the medical tool can be any of the medical tools herein.

The disclosure below relates generally to electrical connections and contacts in a medical device, optionally an ultrasound probe if not otherwise specified. The disclosure that follows can apply to any of the systems, or aspect of the systems, herein. The electrical connections, contacts, device, and methods can be integrated into any of the systems above, such as, without limitation, the handle assembly in FIG. 12.

One aspect of the disclosure includes methods of disassociating at least a portion of the system from other components, optionally as part of a reposing process. In some embodiments the medical tool includes one or more electrical contacts that are coupled to other electrical contacts, which are in electrical communication with an energy console, and examples of consoles are known in the ultrasound art.

Figure 18:
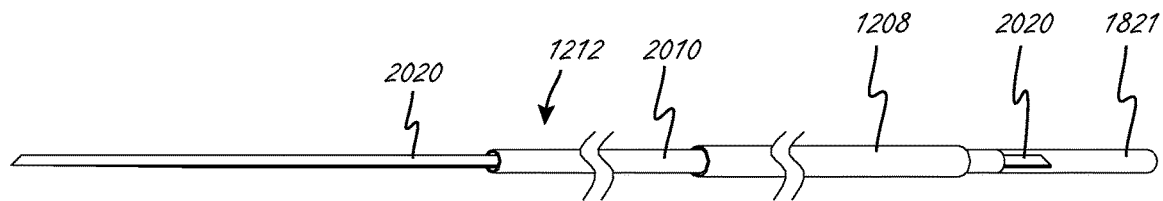
FIG. 18 illustrates an exemplary portion of an exemplary system that includes a bundle.

FIG. 18 illustrates merely a portion of an exemplary medical tool, such as an ultrasound probe, that can be electrically coupled directly or indirectly to an energy console, such as an ultrasound console.

The embodiment shown in FIG. 18 can be used in a manner similar in concept to the embodiment illustrated in FIGS. 13A-C, in that reposing the device involves disconnection of one or more proximal electrical contacts and moving the tool portion distally out of the distal end of the sheath portion. In this embodiment tool portion 1212 comprises at least a tool outer sheath or member 2010, distal working end 1821 (which can include at least one ultrasound transducer), and conductor bundle 2020. The conductor bundle 2020 extends from the distal working end 1821, through the tool outer member 2010 to a proximal connector (the connector and handle mechanism are not shown in FIG. 18 for clarity). In some embodiments the medical tool is used for ultrasound imaging, optionally where the distal working end 1821 comprises a two-dimensional (2D) array of piezo electric components mounted on an ASIC (application specific integrated circuit).

Figure 19:
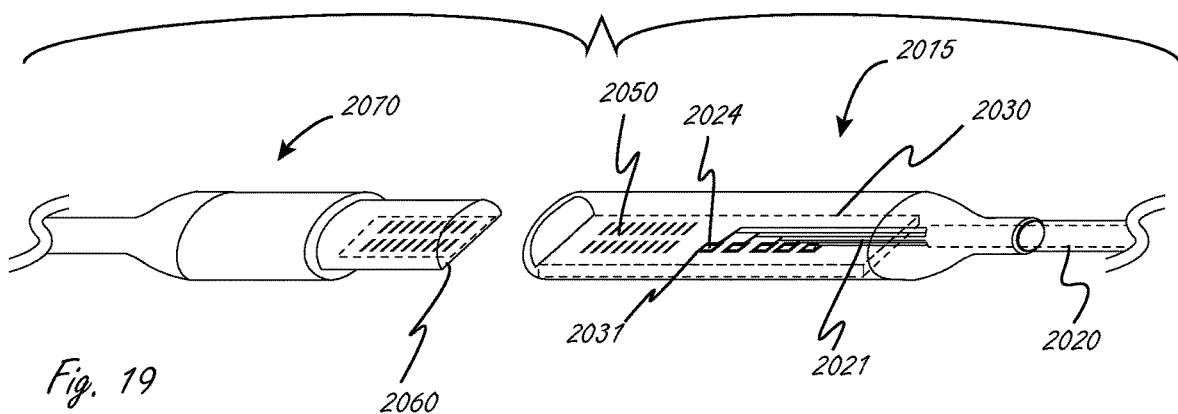
FIG. 19 illustrates an exemplary proximal end of a medical tool, the tool including a conductor bundle that extends into a proximal connector within which is housed a printed circuit board (PCB).

FIG. 19 illustrates a merely exemplary proximal end of a medical device (the medical device is shown on the right), and in this embodiment the medical device is an ultrasound probe. The proximal end 2015 of the medical device is adapted to be electrically coupled to connector cable 270, which is directly or adapted to be indirectly electrically coupled to an energy console, such as an ultrasound energy console. As illustrated in FIG. 19, conductor bundle 2020 extends from a distal region of the medical tool (distal region not shown) into a proximal connector 2015 within which is housed a rigid or flexible printed circuit board ("PCB") 2030. The connector bundle 2020 includes a plurality of contacts 2024 (examples of which are described below) that are attached to PCB board contacts 2031. Each individual trace from each contact 2031 is linked to individual exposed contacts 2050 on another portion, optionally more proximal, of the PCB. The individual PCB traces may also pass through other useful circuitry on the PCB. The exposed contacts 2050 are configured for a mechanical mating for electrical conduction to similar contacts 2060 on mating connector cable 2070, similar in concept to the proximal tool connector 1990 described previously, which links the tool 1204 to a user-interface console. Proximal connector 2015 can be incorporated into any of the systems, handles, steerable sheaths, medical tools, etc., herein, such as that shown in FIGS. 12A and 12B.

Figure 20A:
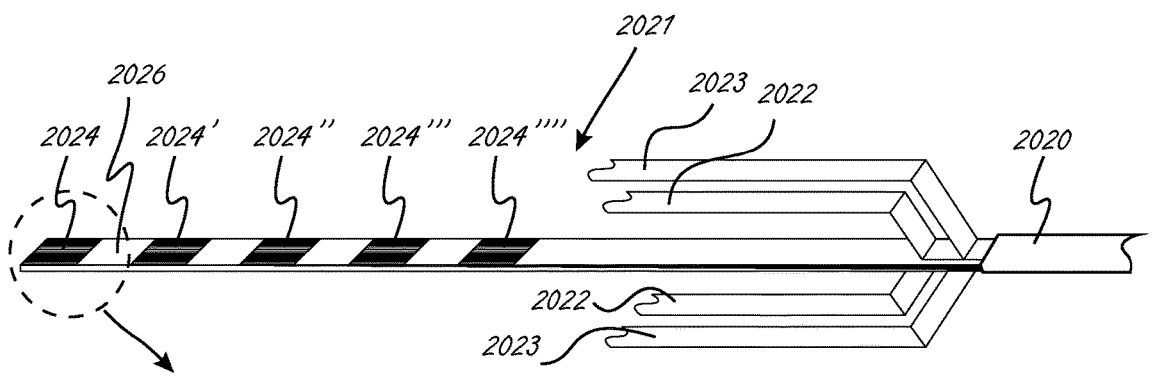
FIG. 20A illustrates a portion of an exemplary medical tool that includes a flexible circuit strip.
Figure 20B:
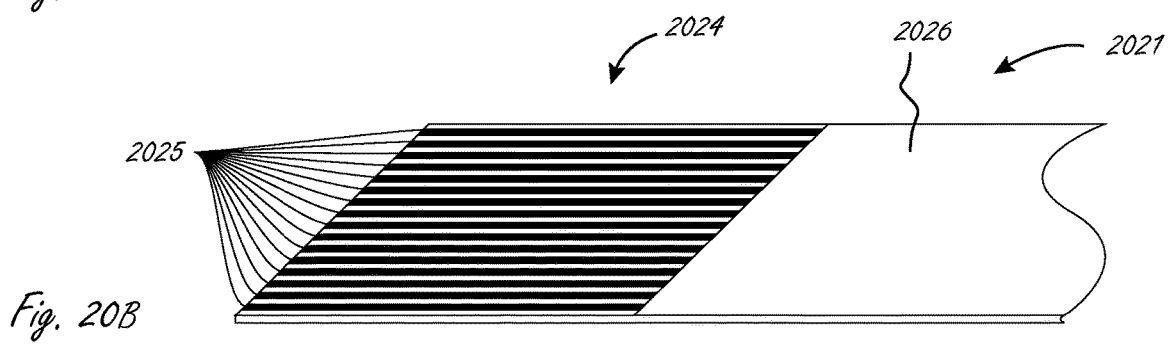
FIG. 20B illustrates an exemplary proximal portion of a strip.

FIGS. 20A and 20B illustrate an exemplary conductor strip (also referred to herein as a flexible circuit strip) 2021 that can be included in any of the conductor bundles herein. The embodiment in FIGS. 20A and 20B is an example of a conductor strip that can be included in bundle 2020 from FIGS. 18 and 19. The embodiment in FIGS. 20A and 20B can be incorporated into any other system herein.

Figure 20C:
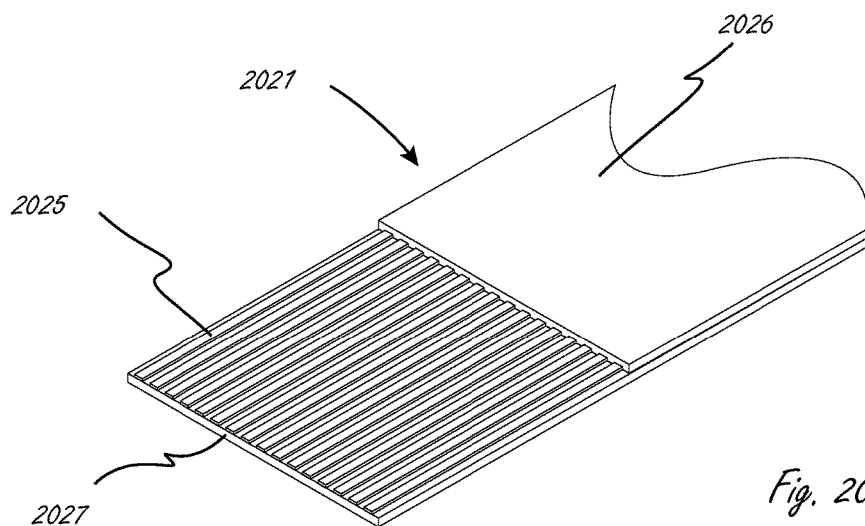
FIG. 20C illustrates a detailed view of an exemplary proximal portion of a strip.
Figures 20D, 20E, 20F, 20G:
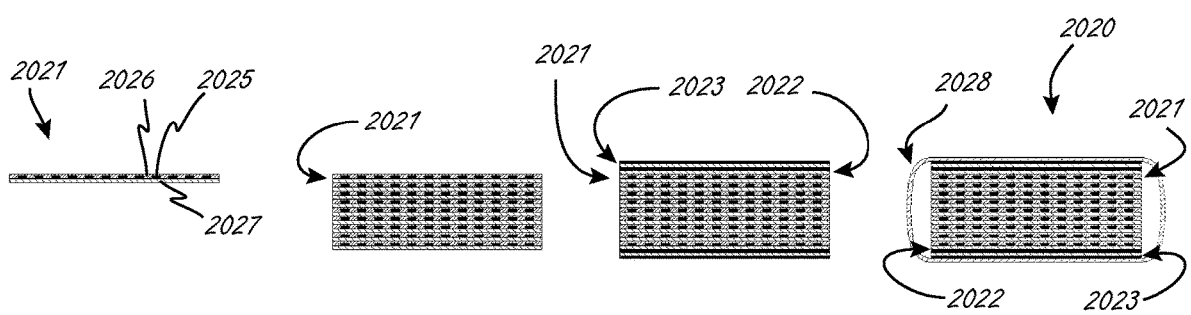
FIG. 20D illustrates an end view of an exemplary flex strip.
FIG. 20E illustrates an exemplary stack of flex strips.
FIG. 20F illustrates an exemplary stack of flex strips and ground and shield strips.
FIG. 20G illustrates an exemplary bundle including a tubing material around a stack of strips and shield and ground strips.

As shown in FIGS. 20A, 20B and 20G, conductor bundle 2020 comprises a plurality of flex circuit strips, including multi-trace strips 2021, as well as conductive strips for grounding 2022 and shielding 2023 (only a portion of which are shown). Each multi-trace strip comprises a plurality of conductive traces 2025, which can be seen clearly in FIGS. 20B, 20C and 20D. The number traces 2025 in FIGS. 20D-G is twelve, and the number of traces in FIGS. 20A-20C is sixteen, and they are both exemplary as to the number of traces 2025 that can be used. Each strip 2021 can be approximately 0.072" wide and 0.0022" thick, and can optionally comprise sixteen 0.0022" widexabout 0.0007" thick conductive (e.g., copper) traces, each spaced approximately 0.0022" apart. The traces are disposed on an insulating substrate layer 2027, such as a polyimide substrate, and the traces can be at least partly covered by a cover layer 2026, such as a photoimageable film cover ("PIC") layer or other dry film solder mask (DFSM) or other similar material. The cover layer generally extends along most of the bundle, except at discrete locations in proximal and distal regions for electrical coupling. In other embodiments, the strip 2021 is approximately 0.055" wide and comprises twelve conductive traces (see FIGS. 20D-G). In other embodiments, the strip 2021 is approximately 0.037" wide and comprises eight copper conductive traces. The outer strips 2022 and 2023 used for grounding and shielding may have a similar construction and dimension except they can comprise a single full width strip of copper. As optimized for a 2D piezo array, a stack of approximately seven 16-trace strips 2021 would be required (or nine 12-trace, or fourteen 8-trace), along with one each of strips 2022 and 2023 on each side of the stack of multi-trace strips. FIG. 20E illustrates a portion of an exemplary bundle 2020 with nine strips 2021 stacked together. FIG. 20F illustrates a portion of the bundle that includes nine strips 2021 stacked, as well as ground strip 2022 and shield strip 2023 (only those on top are labeled). The complete bundle may optionally be held together with a, for example without limitation, about 0.001" wall thickness shrink tube, such as the tubing 2028 in FIG. 20G. The flex circuit dimensions and number of traces discussed above are for a particular configuration of a piezo-electric array (and/or an ASIC controller thereof) and may be varied depending on how the number and size of array elements are optimized for the particular application.

The proximal end of each flex circuit strip has the conductive material (e.g., gold-plated copper) exposed over a length of approximately, for example, 3 mm through removal of the cover layer 2026 at location 2024. Location 2024, and other exposed locations described herein, is generally referred to as a "contact." It is understood that when used in this context, the contact actually includes a plurality of separated conductive traces (such as shown in region location), each of which is adapted to be in electrical communication with its own corresponding conductive element. "Contact" is therefore not limited to mean only a single electrical connection between two conductive elements. While FIG. 20A shows a plurality of exposed regions 2024, the embodiment in FIG. 20A will first be described herein as if there is only one exposed region (i.e., region 2024 at the proximal end). The strip 2021 can be made to create an electrical connection to matching exposed contacts 2031, shown in FIGS. 20A-C, for conductive traces on the PCB 2030. In some embodiments, sixteen individual traces, sized and spaced to match sixteen traces in the multi-trace strip 2021, would be provided within a given contact 2031. An ACF (anisotropic conductive film), soldering, conductive adhesive, mechanical connection, or any combination of these may be used to achieve a suitable electrical connection (electrical coupling) between the strip traces and the PCB contacts.

Figure 21A:
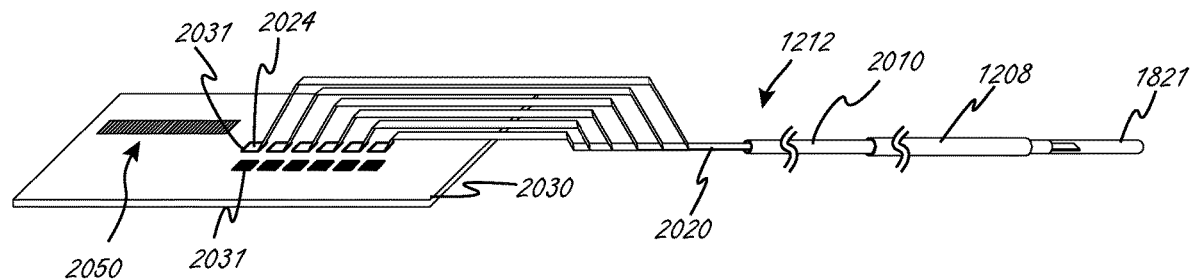
FIGS. 21A and 21B illustrate an embodiment in which a plurality of flex circuit strips have a staggered length and exposed locations are attached to a PCB at contacts provided in a similarly staggered length.
Figure 21B:
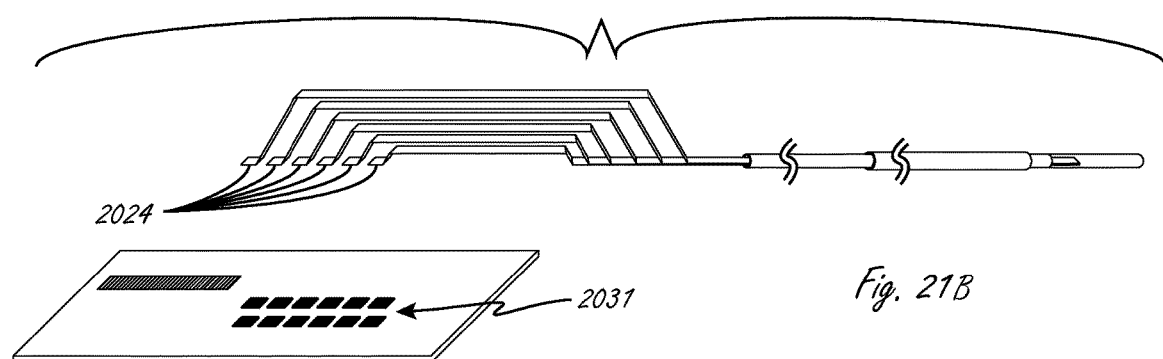

As illustrated in FIG. 21A and FIG. 21B, the plurality of flex circuit strips (not all are illustrated) preferably have a staggered length such that the exposed locations 2024 (each strip has an exposed location 2024 at its proximal end) are attached to the PCB 2030 at contacts 2031 provided in a similarly staggered length. One or more of an array (preferably a linear array) of contacts 2031 could all be on one side of the PCB, or a second array (or array plurality) 2031' (see FIG. 21B) could be provided on the underside of the PCB. Those on the other side of the PCB could allow exposed regions 2024 of other strips to be attached to the other side of the PCB, creating more room and connection options.

Figure 21C:
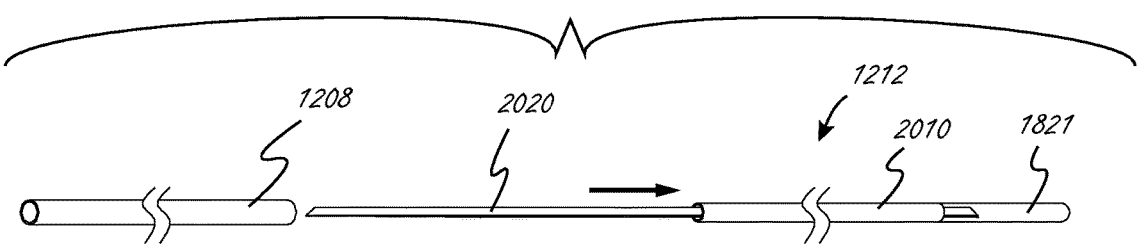
FIG. 21C illustrates an exemplary method of moving a tool distally and out of a sheath, optionally a steerable sheath.

As part of any of the reposing processes described herein, the strip-to-PCB connection may be disconnected to allow the entire tool portion 1212, which includes the now disconnected conductor bundle 2020 (disconnected from the PCB), to be slideably removed out of the distal end of the sheath portion 1208, as illustrated in the direction of the arrow shown in FIG. 21C. Once removed, the outside of the tool portion 1212 and at least the inner and outer surfaces of the sheath portion 1208 may be cleaned and decontaminated. The tool portion 1212 may then be back-loaded proximally through the sheath portion 1208 until the distal working end 1821 is properly seated in relation to the distal end of sheath portion 1208, as is described in more detail herein. The proximal ends of strips 2021, 2022, and 2023 are then reattached to the exposed contacts 2031 and 2031', which can be the same contacts or different contacts. In the case of ACF bonding, the same ACF material may be used and/or it may be cleaned and new ACF material applied prior to bonding. The connection integrity and ultrasound performance may then be tested to verify acceptable performance. This reposing process can be used on any of the systems herein.

One aspect of the disclosure herein is a method of disassembling a system that has already been exposed to a bodily fluid of a subject (e.g., exposed to a blood environment, an esophagus, etc.), the system including a medical tool such as an ultrasound probe, a steerable shaft, and a handle assembly. The method can include providing a handle assembly, a steerable sheath that has been exposed to a bodily fluid environment of a subject, and an ultrasound probe that has been exposed to the bodily fluid environment of the subject, the handle assembly in operable communication with the steerable sheath and the ultrasound probe, the handle assembly including a handle body with an outer surface that can be gripped by a user, a first actuator adapted to be moved relative to the handle body, and a second actuator adapted to be moved relative to the handle body, the steerable sheath having a distal deflectable region that is in operable communication with at least one pull wire, wherein the first actuator is in operable communication with the pull wire such that actuation of the first actuator relative to the handle body causes deflection of the distal deflectable region, and wherein the second actuator is adapted to be rotated relative to the handle body and is also adapted to be moved axially relative to the handle body, and wherein the second actuator is in operable communication with the ultrasound probe such that axial movement of the second actuator relative to the handle body causes axial movement of the ultrasound probe relative to the distal end of the steerable sheath, and such that rotation of the second actuator relative to the handle body causes rotation of the ultrasound probe relative to the distal end of the steerable sheath, the ultrasound probe having a distal portion that includes an ultrasound transducer, the distal portion extending further distally than a distal end of the steerable sheath and having an outer dimension greater than a dimension of a lumen of the steerable sheath in which the probe is disposed, the ultrasound probe further including a flexible circuit strip, the flexible circuit strip comprising an insulating substrate, a plurality of conductive traces disposed on and extending along the insulating substrate, a portion of each of the plurality of conductive traces covered by an insulation member, and a portion of the plurality of conductive traces not covered by the insulation member, the portion of the plurality of conductive traces that are not covered by the second insulation layer defining a probe contact, the probe contact electrically coupled to an electrical contact on a printed circuit board, where the printed circuit board or any of the printed circuit boards herein can be a flexible circuit board. An exemplary system that could be used in this method is shown in FIGS. 12A and 12B. The "providing" step above (or in any other method herein) simply requires that the system be available for the following method steps, and does not require an act of providing or giving the system to another person or entity. Thus, a system simply sitting on a tabletop has been "provided" in this context.

The method of disassembly further includes electrically disconnecting the probe contact from the electrical contact on the printed circuit board, which is described herein.

The method of disassembly further optionally includes moving the ultrasound probe distally relative to the steerable sheath and out of the distal end of the steerable sheath, such as is illustrated in FIG. 21C.

The method of disassembly can optionally further include, but does not necessarily need to include, cleaning at least a portion of the ultrasound probe, the portion comprising a region of the ultrasound probe that was, before the moving step, not extending out of the sheath, and optionally disposed within the handle assembly. For example, in FIGS. 12A and 12B, a portion of the medical device is disposed within the handle assembly.

The method of disassembly can optionally further include, but does not necessarily need to include, at some time after the optional cleaning step, electrically coupling the probe contact to either the printed circuit board or a different printed circuit board.

The method of disassembly can further comprise (and may in fact require), at some time before the moving step, releasing the ultrasound probe from a releasably secured engagement with a handle assembly component. In some embodiments the ultrasound probe will not be able to be removed from the handle assembly without first doing this. Releasing the ultrasound probe from a releasably secured engagement with a handle assembly component can comprise releasing the probe from a releasably secured engagement with a handle assembly component that is in direct or indirect operable communication with the second actuator. For example, FIG. 12A illustrates a medical device releasably secured to handle assembly component 1755, which in that embodiment is described as a tool lock. A method of disassembly can include, prior to the moving step, releasing the ultrasound probe from a releasably secured engagement with tool lock 1755, which is in this embodiment is also an example of a handle assembly component that is in direct or indirect operable communication with second actuator 1780.

In some embodiments herein, an ultrasound probe and handle assembly are adapted so that the probe can be moved axially (distally and proximally) relative to the sheath. Bodily fluids such as blood can enter into the space between the probe and sheath, thus necessitating cleaning before reuse of the usually relatively expensive probe. In some embodiments, the distal tip of the ultrasound probe has a larger outermost dimension than the distal end of the steerable sheath. This can be desirable as a way of minimizing the footprint of the sheath within a patient. After the probe has been used and exposed to a bodily fluid, the probe thus cannot be retracted proximally within and relative to the sheath to disassemble the probe from the sheath. The probe must then be removed distally relative to and from the sheath in order to repurpose the probe. Because the probe is attached at its proximal end to some type of connector (e.g., directly or indirectly to an ultrasound console), the probe must therefore first be taken out of electrical communication with the connector prior to moving the probe distally relative to the sheath.

In an alternate embodiment, during a reposing process it may be more efficient and/or reliable to not re-attach the original exposed locations 2024 of the conductive strips 2021 (and, if necessary, 2022 and 2023). In this case, as illustrated in FIGS. 20A and 20B, each strip 2021 may be provided with a plurality of exposed locations 2024, 2024', 2024", etc. (each optionally about 3 mm in length) staggered in a distal direction along the strip length. Thus, the original location 2024, as well as a section of layer 2026, may be trimmed off or removed using other techniques, and the next most proximal location 2024' can be used for the new connection attachment. This process can also be repeated for future reposing processes until all of the exposed locations are used. This would also serve to limit the number of reuses of the device. The exposed but not-in-use locations on the strips can also be protected until ready for use with a, for example, peel-away insulating low tack adhesive strip. In other embodiments, this protective layer could be a paste, an adhesive, or a cured polymer having sufficient dielectric properties and conformability to insulate adjacent exposed conductors within a given strip. The material is preferably reversibly adhered such that it can be easily peeled or dissolved away from the exposed conductors without damaging the conductors. In some embodiments a covering layer that is disposed over the traces can be ablated away (e.g., using a laser, sandblasted, or sanded) to reveal an exposed region of traces, which can then be used as a contact location.

In some embodiments alternative to that shown in FIGS. 20A and 20B, the strip can first be attached with the only exposed region being proximal-most region 2024, and wherein the cover layer 2026 extends distally without any discontinuities in layer 2026. After a first use, region 2024 can be removed. To expose another conductive region, a portion of the now-proximal end of layer 2026 can be removed, such as by ablation, or if the layer 2026 is a peel-away section, peeling it away. This process can be repeated as needed after each use to create new exposed conductive regions.

In other embodiments, an intermediate strip-strip ACF bond location could be made between the PCB and where the strips exit the proximal shaft. This location could be detached/re-bonded instead of the strip-PCB location. The strip-strip ACF bond locations within the catheter shaft just proximal to the ultrasound transducer could also be locations where detachment/re-bonding occurs during the reposing process. As described above, a plurality of discreet regions on the flex strip on each side to the original bond location may have exposed conductor regions for re-bonding after the original ACF bond joint is detached and trimmed away during the reposing process. Also as described above, the exposed regions could be protected until needed for use.

Figure 22:
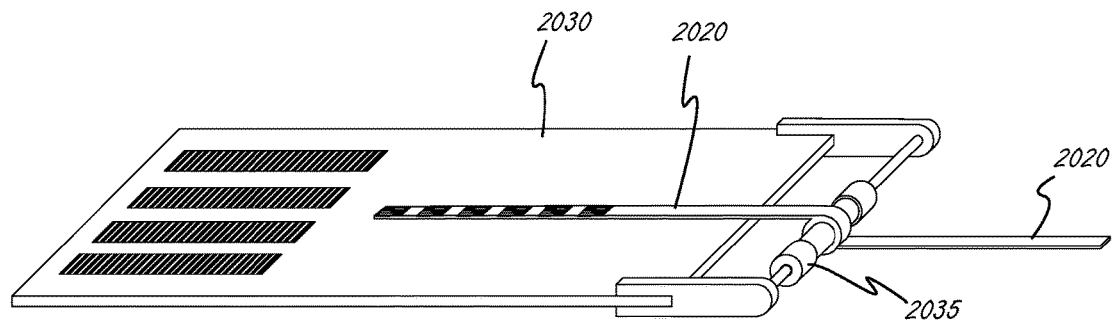
FIG. 22 illustrates an exemplary embodiment in which a conductor bundle can be reversibly spooled or wrapped around a spool comprising a rod, tube, spindle or similar rotatable structure.

In embodiments in which the flex circuit strips are trimmed or removed using any suitable technique to attach the next exposed element of the flex circuit strips to the PCB, it may be necessary to advance the strips forward to establish the electrical connection. This may be difficult or impossible if the strips are confined and immovable within a tube, or otherwise securely housed, up to the PCB. As illustrated in the exemplary embodiment in FIG. 22, to allow extra length to be advanced relative to the tube, a conductor bundle 2020 (which can be the same as bundles 2020 herein or different bundles) could be reversibly spooled or wrapped around a spool 2035 comprising a rod, tube, spindle or similar rotatable structure, for a length suitable to advance out all exposed elements. Before winding, the conductor bundle could be first passed through a slot passing transversely through the central axis, or the bundle could be wound from one end of the outer surface of the spool to the other. Thus after trimming off one contact set, the conductors are unwound off the spool to make the next set of connections on the PCB 2030. The spool preferably has a central axis which could be mounted on the distal end of the PCB or within a mechanism just distal to the board, and secured within the proximal connector 2015. The spool may also serve to protect the connections to the PCB from being strained due to tensile or twisting forces applied to the flex conductor bundle. To prevent premature unwinding, the spool could be fitted with a keyed feature reversibly connected to the PCB or other location within the proximal connector or connector housing itself.

To allow access to the PCB 2030, and spool 2035 if applicable, the proximal connector (e.g., proximal connector 2015) can be fitted with a removable housing that has a custom design for it to mate with other portions of the connector and/or the PCB 2030 and/or the spool 2035. Optionally, to remove this housing completely will require breaking the housing thereby rendering it non-functional, requiring replacement prior to continued use.

Distal to the spool, the conductor bundle 2020 is optionally irreversibly secured within the tool outer member 2010. The tool outer member 2010 preferably also extends proximal to the handle 1206. After disconnection of the flex circuit from the PCB, to allow the assembly of the tool outer member 2010 and conductor bundle to be removed from the handle 1206 and sheath portion 1208, the assembly is preferably slidable within any tubular connection line between the handle 1206 and proximal connector 2015. Reversible seals, similar to those previously described herein, could also be used between the tool outer member 2010 and tubular connection line.

If removing the original connection to the PCB at connectors 2031 compromises the integrity of these connections, the PCB could include a plurality of arrays of redundant connectors 2031', 2031" etc. to which connections can be made with each reposing cycle of the device.

In another embodiment, the PCB could simply be replaced with a new identical PCB to which the exposed ends 2024 (or 2024', etc.) of the flex circuit strips could be attached.

Figure 23:
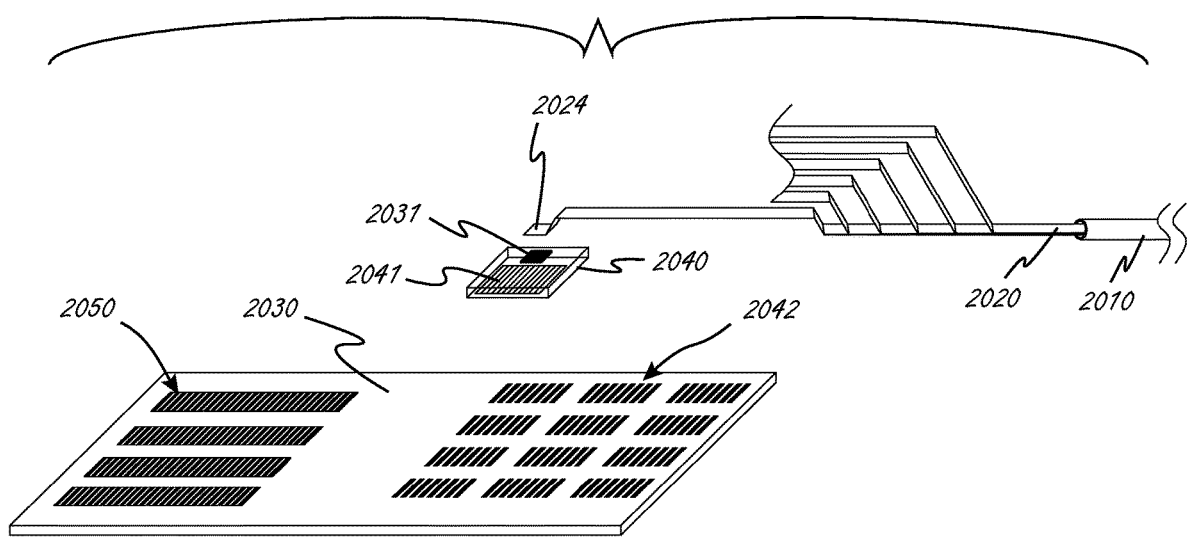
FIG. 23 illustrates a portion of an exemplary embodiment in which exposed flex circuit ends are attached to a disposable mini-PCB element which has a same size connection on one side, but a larger exposed connection on the opposite side.

FIG. 23 illustrates another embodiment in which exposed flex circuit ends (2024 or 2024') could be attached to a disposable mini-PCB element 2040, which has the same connection 2031 on one side, but larger exposed connections 2041 on the opposite side, linked through traces in the mini-PCB, suitable for a reusable mechanical connection to the PCB 2030. The mechanical connection from connections 2041 on the mini-PCB 2040 is made against matching exposed mechanical connections 2042 on the PCB 2030. Spring clips or other suitable holding mechanisms could be integrated into the PCB to hold the mini-PCB contacts against those on the PCB. Each individual trace from each contact 2042 is linked to individual exposed contacts 2050 on another portion, preferably more proximal, of the PCB. The individual PCB traces may also pass through other useful circuitry on the PCB. The exposed contacts 2050 are configured for a mechanical mating for electrical conduction to similar contacts 2060 on a mating connector cable (e.g., cable 2070) which links the medical tool to the console. During the reposing process, the mini-PCB may be unclipped from the PCB and the flex circuit detached or clipped away from (as previously described) the mini-PCB. After removal, cleaning, and reassembly of the tool in the sheath, the flex circuits may then be reattached to new mini-PCBs that are re-connected to the original PCB.

The construction of the medical tool 1212 may be optimized to minimize the diameter and to provide optimal torque response of the distal working end (e.g., working end 1812). In some embodiments, the flex circuits are routed through an inner lumen of tool member 2010, similar to that illustrated in FIG. 17B.

Figure 24:
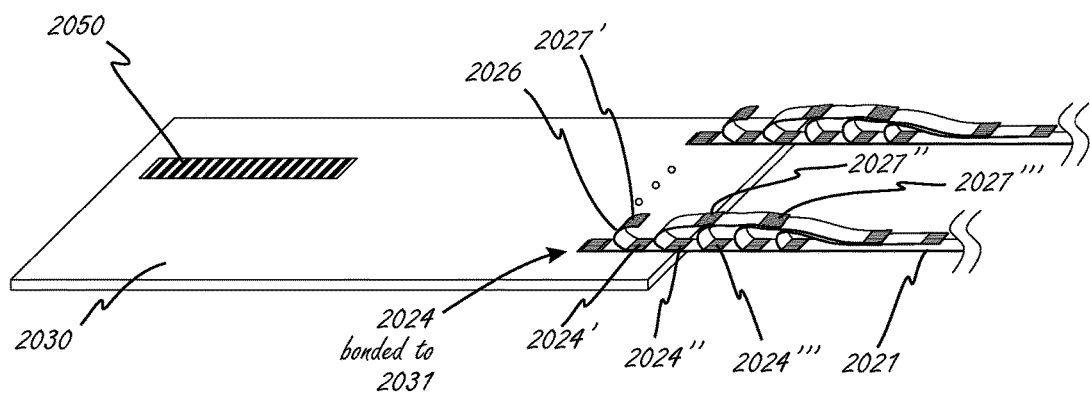
FIG. 24 illustrates an exemplary embodiment of multiple intermediate flex extension strips bonded to primary flex strips.
Figure 25:
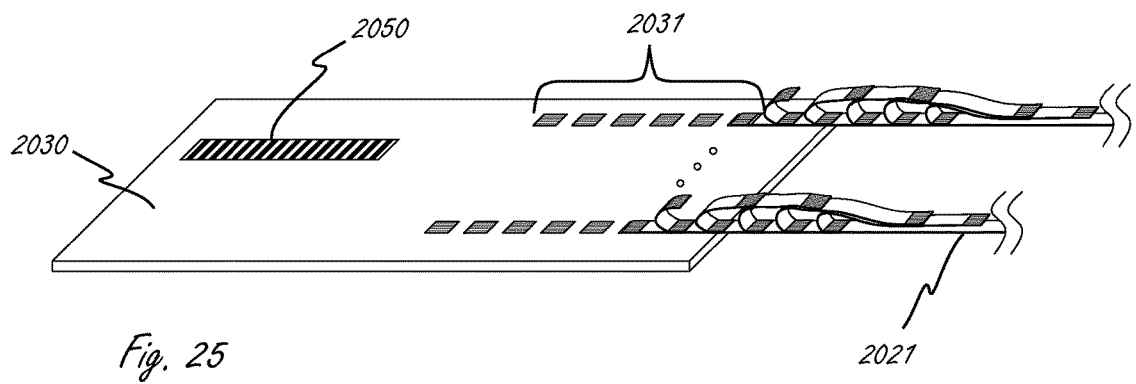
FIG. 25 illustrates an embodiment with a printed circuit board designed with redundant attachment locations.

In another embodiment shown in FIG. 24, it may be desirable to have multiple intermediate flex extension strips 2026 bonded to each primary flex strip 2021. Using the example of FIG. 20, these intermediate extension strips 2026 are bonded during manufacturing at locations 2024', 2024", 2024''', and so on, creating a new extended bond location 2027', 2027", 2027''', and so on. The multiple strips 2026 could be folded and releasably secured tightly against the original flex 2021 with tubing, coils, tape, etc., until ready for use. During the reposing process, the original attachment extension (location 2024) is cut away from the PCB, and the next extension (e.g., containing attachment location 2027') is bonded to the PCB. In FIG. 24, the PCB may be replaced each time the attachment is cut away. In FIG. 25, the PCB may be designed with redundant attachment locations 2031 to allow the next flex to be attached without disturbing the attachment of the trimmed-away original. This may be desirable if removal of the original were to cause open circuits or cross-circuit connections. The unattached ends of each extension strip could also be fitted with mini-PCBs 2040 as described for FIG. 23. FIGS. 26A-F illustrate how the flex changes as each portion is trimmed away at each reposing cycle, with FIG. 26A showing the original attachment, FIG. 26B showing the $2^{nd}$ use, etc., with FIG. 26F showing the $6^{th}$ use. Since the purpose of trimming the flex is to remove it with the tool 1212 through the outer sheath 1202, each stack of redundant extensions may need to be staggered lengthwise to facilitate removal, such as is illustrated in FIGS. 27A-G (flex strip 2021 only labeled in FIG. 27A). The staggered length between stacks may be compressed within the connector or the attachment between the connector and handle until allowed to stretch out for removal.

FIG. 28 illustrates the cross-section of the bundled stack 2020 inside member 2010. In this embodiment, the ~0.072" width of the flex circuit bundle is optimized for the width of the ASIC to which the piezoelectric components are mounted. Taking into account shrink tubing around the stack, the stack dimensions are approximately 0.028" thick× 0.085" wide. The inner lumen of the tool member 2010 would require an inner dimension, in at least one dimension, of approximately 0.089". This dimension then drives the outer dimension of the member 2010 which also impacts the inner and outer dimensions of the sheath portion 1208.

While the conductor bundle 2020 may simply be routed through a circular inner lumen of the tool member 2010 as shown in FIG. 28, it may alternatively be constrained within a non-circular lumen such as is illustrated in FIG. 29. In this configuration, additional "D" lumens are also provided such that additional stiffening members 2100 may be added to create a more uniform bending stiffness in a variety of directions such that the stiffness along the long axis of the conductor bundle 2020 does not dominate the shaft stiffness. This will serve to minimize "whipping", or sudden jerks in torque response, as the tool member 2010 is torqued.

FIG. 30 illustrates an embodiment, similar to that shown in FIG. 29, where different size lumens are provided to accept stiffening members 2101 and 2102. These may also serve to create a uniform bending stiffness. The tool member 2010 is preferably constructed with an outer braid of wire and/or fiber which is heat laminated with a jacket of thermoplastic polymer (e.g., Pebax in durometers ranging 25 D to 72 D or other suitable catheter material known in the art).

The embodiment of FIG. 31 illustrates a "D" shaped member 2103 applied to either side of the flex circuit bundle 2020. This creates a uniformly round member which can be held in place with a thin wall (~0.001" thick) heat shrink tube. In one embodiment, the assembly may then be inserted into a tool member shaft 2010. In another embodiment, the tool member shaft can be constructed directly around the conductor bundle. For example, to improve torque response and minimize the size of the tool 1212, multiple fibers and/or metal wire (round or ribbon shaped) may be braided directly over the conductor bundle 2020. A jacket of polymer (such as Pebax in a range of durometers from 25 D-72 D, or other common catheter materials) may be laminated with heat to reflow the polymer over the entire braid to form a uniform member. A polymer layer similar to the jacket may also be laminated over the conductor bundle before braiding to improve the reflow penetration of the polymer into the braid during heat lamination.

For the embodiments of FIGS. 28-31, the luminal space between the conductor bundle and inner diameter of shaft 2010 could be used to route pull wires used to steer the tool 1212 independent of the steerable sheath 1202. The stiffeners themselves could be used as pull wires, or replaced with more traditional pull wires (e.g., round and/or flattened stainless steel or nitinol, or a cable braid of these materials). The pull wires could be fixed at the distal end of the shaft 2010 and actuated in a manner similar to other embodiments described herein.

In an alternative embodiment, illustrated in FIG. 32 and showing exemplary bundle 2020, each flex circuit strip could be made with approximately half the number of traces, and thus have approximately half the width (~0.037" wide). For the specific embodiment described above, this requires doubling the number of multi-trace circuits to approximately 14. This, in combination with the ground and shielding flex circuits, creates as stack of about 17 flex circuits. The resulting width and height are more even, close to 0.042" each with the heat shrink. This allows a more efficient use of space within the lumen of member 2010 and improves the uniformity of the torque response. As described for FIG. 31, the stack could be inserted into a tubular shaft or the shaft constructed around it with a braid and jacket. Other configurations are also contemplated between those illustrated in FIG. 28 and FIG. 32 for optimization with the transducer assembly. For instance, the width of the flex bundle with heat shrink may be limited to approximately 0.068" with a stack of 13 flex circuits being approximately 0.031" thick.

In another embodiment, the ground and/or shield strips are replaced by separate braids or winds of conductor wire (individually insulated or not insulated) around the bundle of flex multi-trace flex circuits. If the ground and shield conductors are not insulated, an insulating polymer layer may be added between the braids of ground and shielding conductors. This conductor braid may be provided in addition to or instead of the braid of fibers and/or metal wire/ribbon. One or more tubes coated with a metal or a conductive polymer (e.g., polyurethane with silver particles) could be applied around the bundle. In some embodiments, this tube could be heat shrinkable. Insulated conductors may also be woven into the braid of fibers and/or metal wire/ribbon in the wall of the shaft of tool 1212, or the shaft 1208, to optimize torque response of tool 1212 or shaft 1208 and minimize the number of braided layers.

In another embodiment, the conductor bundle 2010 may be twisted to provide a more balanced cross-section along the majority of the length of the tool 1212. The twisted bundle may be twisted by securing the ends of a given portion of the bundle and twisting in opposite directions, or the bundle may be wrapped around a mandrel, the mandrel removed, and the bundle pulled down on itself. A complete turn over 2+/−1 cm is considered optimal, but other wrap pitches that are tighter or looser are contemplated depending on the thickness of the bundle and robustness of the conductors. The bundle is preferably twisted, in just the portion of tool shaft 1212 which will experience deflection from the outer shaft 1208 (such as shaft portion 1222 in any of FIGS. 7A-E). The conductor bundle may be run straight in the distal few centimeters to facilitate connection to the distal working end 1821.

In another embodiment, the individual flex circuit strips may be wrapped around the outer dimension of an elongated central core member. The core may be a solid or tubular construction of a polymer or metal, or a composite braid. The wraps may be a group of parallel strips in one layer, but may be wrapped in multiple layers. Preferably, layers are wrapped in alternating directions to optimize torque of the unit. The wrapped strips are preferably laminated against the central core with a polymer jacket. In other embodiments the inside of the jacket may have a loose clearance with the conductor strips to allow some flexural movement for strain relief of the strips. A braid over this jacket followed by lamination of a second jacket over the braid may also be provided. Similar to the embodiment described above, the ground and/or shield conductors may be replaced with braided or wound conductors. In another embodiment, the stack of flex strips may be jacketed as previously described and then twisted in a given direction to provide less bias to bending within the lumen of shaft 2010. The jacketed stack may also be formed into an accordion-like shape within the lumen to improve the ability of the stack to flex with bending of the distal portion of the device, thus minimizing the likelihood of conductor breakage. The twisted or accordion-like shape may only be necessary within the distal portion of the tool 1212 where flex is likely to occur.

As previously described, a medical tool (e.g., any of tools 1212 herein) may be advanced and rotated within the outer shaft, such as illustrated in the example of FIG. 7. Limiters in the handle may control the amount of axial and rotational travel. Preferably, the distal advancement of the tip (e.g., 1821 in FIG. 13A or 3000 in FIGS. 33-35) attached to the distal end of tool 1212 is limited to up to 3 cm, although greater distances could be certainly be employed. Similarly, the rotation of tool 1212 is preferably constrained to approximately 180 degrees in either a clockwise or counter-clockwise direction from a neutral start position. Limiting the rotation of the tip prevents continuous rotation of the tool and any resulting "wind-up" of conductors therein which could cause damage to the conductors. Where a tip contains an ultrasound transducer imaging perpendicular the central axis of the medical tool, the user would only need to rotate up to a total of approximately 360 degrees to find a desired imaging window. Rotation of the proximal end of the medical tool slightly beyond 360 degrees (180 degrees in either direction), such as 380 degrees, may be necessary to overcome torque losses along the length of the shaft such that the tip is able to achieve the desired rotation. Greater total rotation such as a total of 540 or 720 degrees is contemplated based of preferences of the user.

Figure 48:
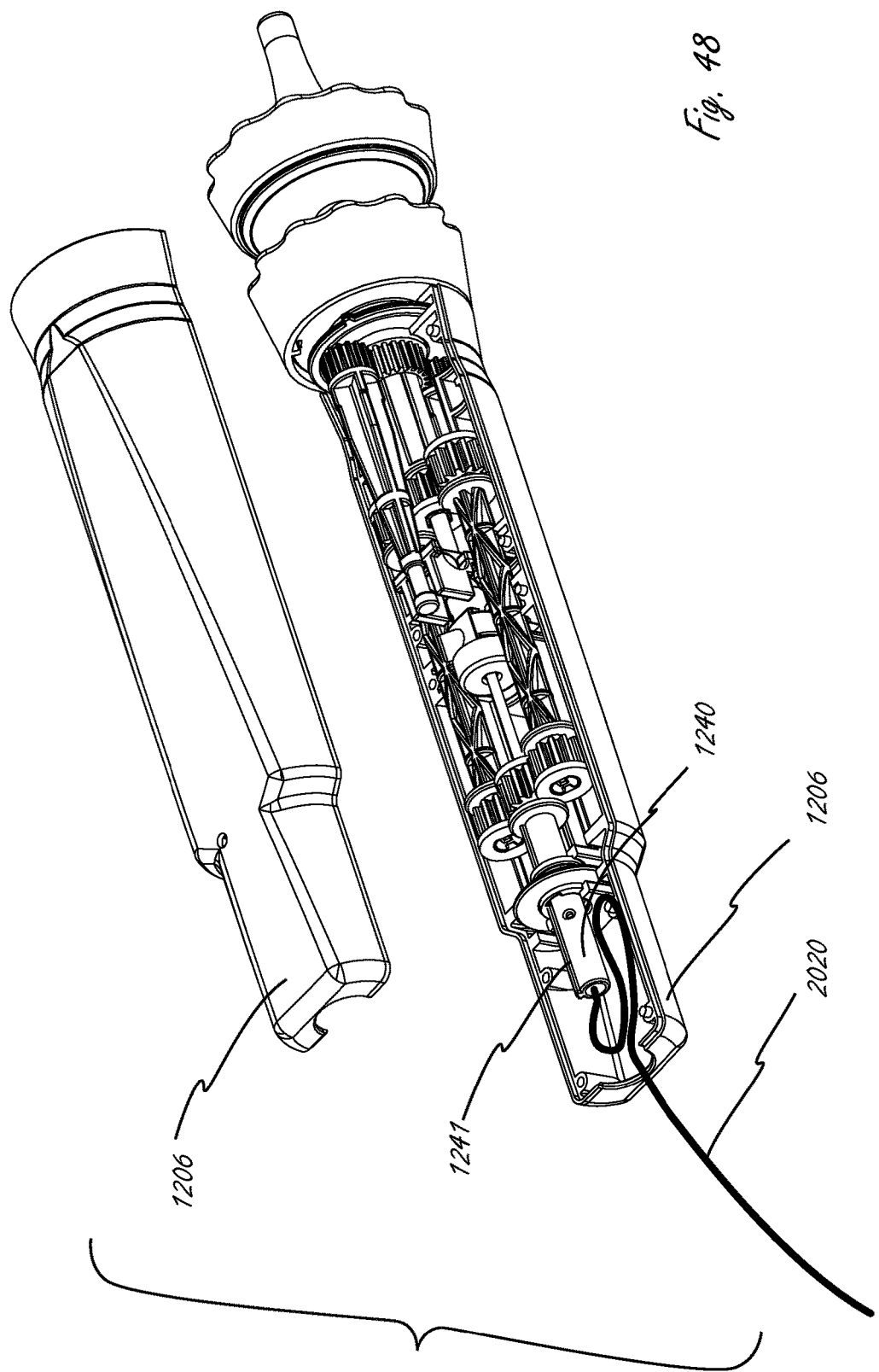
FIG. 48 illustrates an exemplary handle assembly with space for bundle slack.

As illustrated in FIG. 19, the tool 1212 may have a connector 2015 which during operation is typically connected to connector cable 2070. Proximal to the central shaft 1240, where it is bonded to the tool shaft 1210 (of tool 1212), the conductor bundle 2020, either alone as it exits the proximal end of tool shaft 1210, or while still housed within tool shaft 1210, is housed in a space where sufficient slack is allowed for bundle 2020 to translate or rotate relative to the space in which it is housed. As illustrated in FIG. 48, this housed space 1241, or slack region, may be defined by a volume within the handle 1206. The slack region could also be provided proximal to the handle in a volume of a connector housing, or within a volume within a strain relief tubing linking the handle 1206 and connector 2015. Since the connected connectors 2015 and 2070 are constrained from movement during device operation, the translation and rotation of the tool 1212 in the space between the handle 1206 and connector 2015 must be accommodated. The slack may be accommodated by creating a sweeping coil of the bundle 2020 with or without shaft 1210 such that it may rotationally wind or unwind and translate axially back and forth. In another embodiment, the shaft 2010 in the slack region may be made of a highly compliant material or composite construction that allows it to stretch relative to, or easily flex with the conductor bundle 2020. Additional compliance in the conductor bundle 2020 itself may be created by creating a sinusoidal or accordion like construction of the conductors within the slack region. To better accommodate axial translation, the conductors could fold back on themselves in an "S" shape for a few centimeters (for example) to accommodate the translation.

Figure 33:
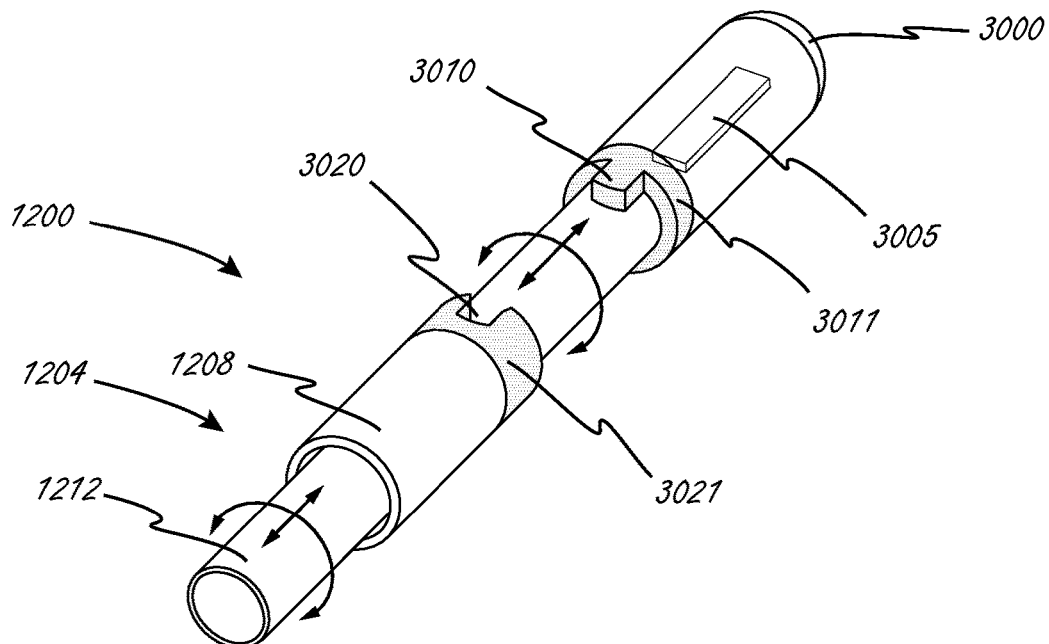
FIG. 33 illustrates an exemplary embodiment in which a medical tool and steerable sheath are configured to interface.

FIG. 33 illustrates a medical device tool 1204 with tool portion 1212 which is slidable within distal sheath 1208. The tool is preferably an ultrasound imaging device with imaging tip 3000 comprising imaging transducer 3005. The imaging tip 3000 is preferably larger than the shaft 1212 and also comprises a tip key 3010 on its proximal edge intended to insert into a mating sheath key 3020 on the distal end of sheath 1208. As illustrated in FIG. 33, tip key 3010 inserts into sheath key 3020, but the reverse is also contemplated. The mating keys allow the orientation of transducer 3005 to be matched to the keys, and any other features linked to sheath 1208 (e.g., steering direction, handle knob orientation, etc.). The key also helps link the transmission of torque to the tip 3000 between sheath 1208 and tool 1212. In one embodiment, sufficient clearance between the keys may be provided such that the tip key 3010 is easily retracted into and advanced out of sheath key 3020. In other embodiments, the keys may be linked with a light friction fit. In other embodiments, a feature on the keys may provide for an automatic lock upon engagement, with a mechanical or electromechanical actuator leading back to the proximal handle that allows unlocking of the keys. The key may be formed into an "L" or similar shape that allows a "twist-to-lock" engagement after being brought together in the axial direction. Mechanical unlocking of the keys may be further tied to a circuit containing an encryption key that is required to unlock and advance forward the tool 1212 relative to the shaft 1208. In another embodiment, the encryption is directly controlled via crypto-chip located with the tip 3000, preferably within the same circuitry that impacts the performance of transducer 3005. In one embodiment, the keys may be formed of an electrically conductive material (e.g., platinum or gold) which have separate conductors leading back through their respective shafts to a connector. This conductive link may be linked to an authentication circuit that ensures the correct match of a given inner tool to the outer sheath. It may also be used to provide user feedback on the position of the probes (e.g., visual indicator tip up on handle when keys mate and circuit is completed). The keys 3010 and 3020 may also comprise magnets of opposite polarity for positive axial engagement and rotational alignment. In certain magnet embodiments, alignment of the magnetic poles may be sufficient to obviate the need for a mechanical (e.g., male/female) fit of the keys. In certain embodiments, the keys may be fabricated from an annular tip key material 3011 and sheath key tip material 3021, which is readily bonded to the tip and shaft, respectively. The keys 3010/3011 or 3020/3021 are preferably formed from a rigid machined or molded plastic (e.g., polycarbonate, peek, epoxy, etc., known in the art), or metal (e.g., stainless steel, platinum, iridium, tungsten, etc.), rare earth magnets (e.g., neodymium, samarium-cobalt, etc.), or any combination thereof. To allow for fluoroscopic visualization, the material may be inherently radiopaque or contain radiopaque fillers such as barium sulfate, tantalum, tungsten, etc.

Figure 34:
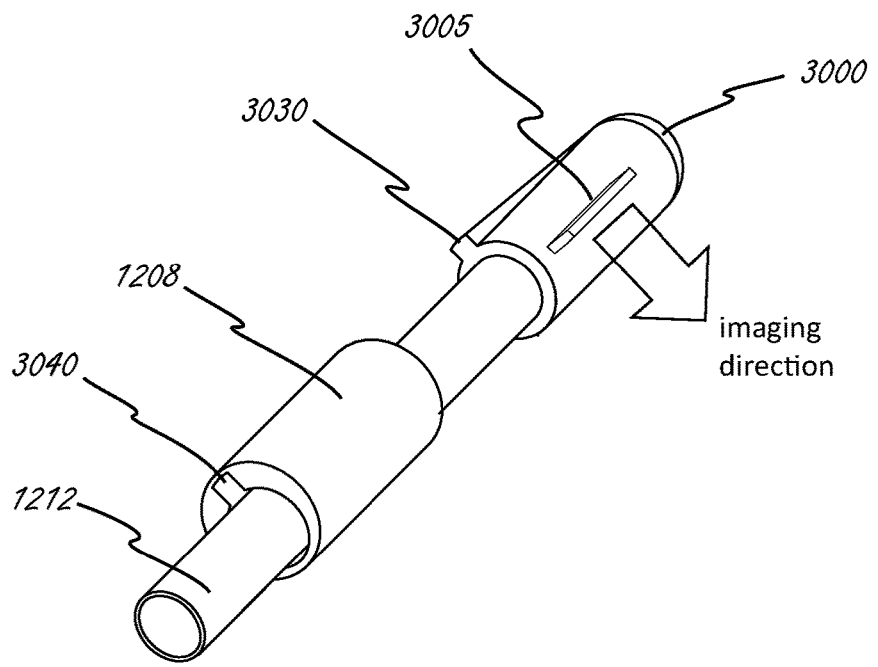
FIG. 34 illustrates an exemplary embodiment in which a medical tool and steerable sheath are configured to interface.
Figure 35A:
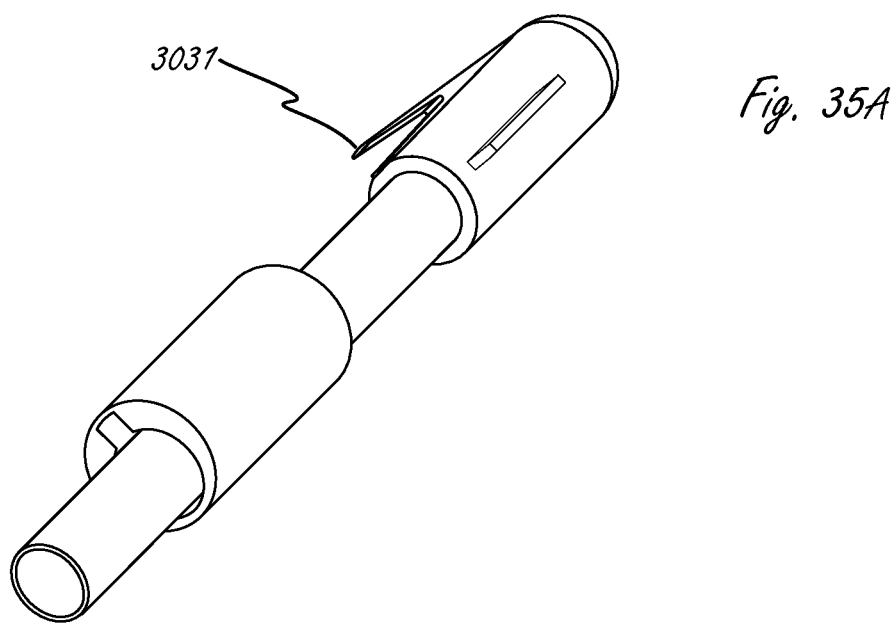
FIG. 35A illustrates an exemplary embodiment in which a medical tool and steerable sheath are configured to interface.
Figure 35B:
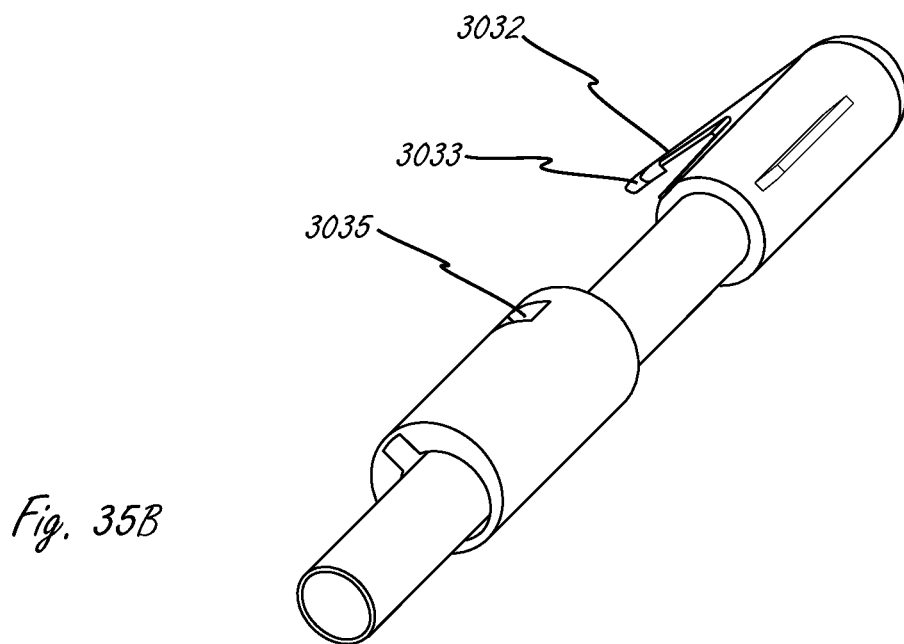
FIG. 35B illustrates an exemplary embodiment in which a medical tool and steerable sheath are configured to interface.

FIG. 34 illustrates an embodiment similar to FIG. 33 except that a key 3030 is provided on tip 3000 that is raised in relation to the surrounding tip surface. This raised portion may be along a complete length of tip 3000, or just proximal to transducer 3005, or tapering down in height from the proximal edge of tip 3000 to any location further distal. Where the raised portion continues over the transducer 3005, the transducer is preferably aligned to create an imaging plane or volume 3006 in a direction opposite to the raised direction of the key feature. The tip 3000 with key 3030 is designed to through the lumen of shaft 1208 only by providing an additional internal space 3040 that allows passage of the key 3030. When aligned in the internal space 3040, the key 3030 does not allow the tip 3030 to rotate freely within the lumen of shaft 1208. In FIG. 35A, the key 3030 is formed into a living hinge 3031 that can be compressed down during insertion through the shaft 1208, but then automatically springs up upon exiting the shaft. In FIG. 35B, the key 3030 is formed with proximal extension 3032 that has a feature 3033 directed radially inward to engage with sheath receptacle 3035. Engagement occurs after advancement of the tip 3000 out of sheath 1208 and then retraction back against the tip. Rotation of the tip 3000 may be required to engage 3033 into 3035.

Figures 36A, 36B:
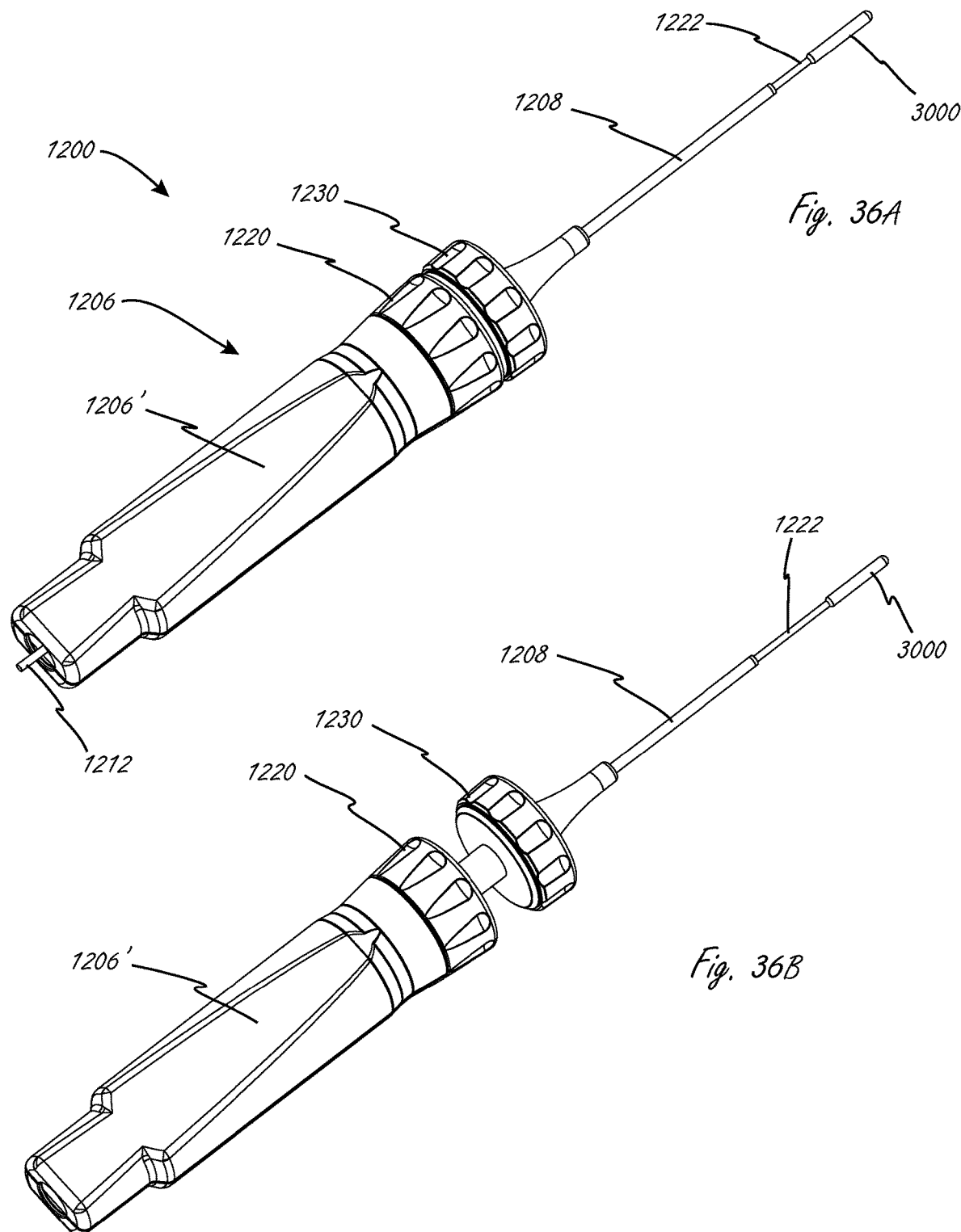
FIGS. 36A and 36B illustrate an exemplary system including a handle assembly adapted to cause axial and rotational movement of a medical tool separate from a steerable shaft.

FIG. 36A illustrates another embodiment of system 1200 comprising steerable sheath 1202 comprising sheath handle 1206 and medical tool 1204. The tool 1212 is slidable within sheath shaft 1208. Actuation of the sheath steering actuator causes the steerable shaft portion 1222 to deflect. The user may also rotate the sheath body 1208 by rotating the handle shell 1206'. Since the tool 1212 enters sheath portion 1208 at the proximal end of the sheath (preferably via a hemostasis valve 1950 fitted on the proximal end of the steerable sheath), the tool knob 1230 must be in operable communication with an attachment point on the tool 1212 proximal to the proximal end of sheath shaft 1208 and hemostasis valve 1950. Preferably, the tool 1212 is fitted with a tip 3000 such as would be suitable to contain an imaging transducer as has been previously described. As illustrated in FIG. 36B, axial advancement and rotation of the medical tool (illustrated in FIG. 36B) is accomplished by actuation of tool knob 1230 which is positioned just distal to the steering actuator 1220. The distal tool knob 1230 eliminates the need to manipulate the tool 1212 from a location proximal to the handle, such as is illustrated in FIG. 8 where the tool 1212 is manipulated by grasping tool handle/connector 1210 or the tool shaft 1212 itself.

Placement of tool knob 1230 just distal to steering actuator 1220 helps keep the two controls adjacent one another to minimize the need for the operator to adjust their hand position and allow for single handed use. In a preferred embodiment, the distal advancement of the tool knob 1230 (as shown by the distal-proximal straight movement arrow) may be limited to 3 cm for easy single movement of the fingers without changing the hand's grip. For some users, up to 5 cm may be preferred. Other longer distances are also contemplated and can be selected based on the desired application. Providing a sight gap between tool knob 1230 and steering actuator 1230, such as, for example, 1-5 mm, upon full proximal displacement of the tool knob may be desirable for the user to have a space for fingers to get behind the knob prior to advancing the knob in the distal direction. As illustrated in FIG. 3B6, the knobs 1220 and 1230 are similar in diameter. Differentiating the diameters, shape, lengths, and or texture of knobs 1220 and 1230 is contemplated for the user to intuitively distinguish between them without looking directly at them (such as when the user's focus remains on a screen displaying the fluoroscopic and/or ultrasonic position of the device in the body).

Figure 38A:
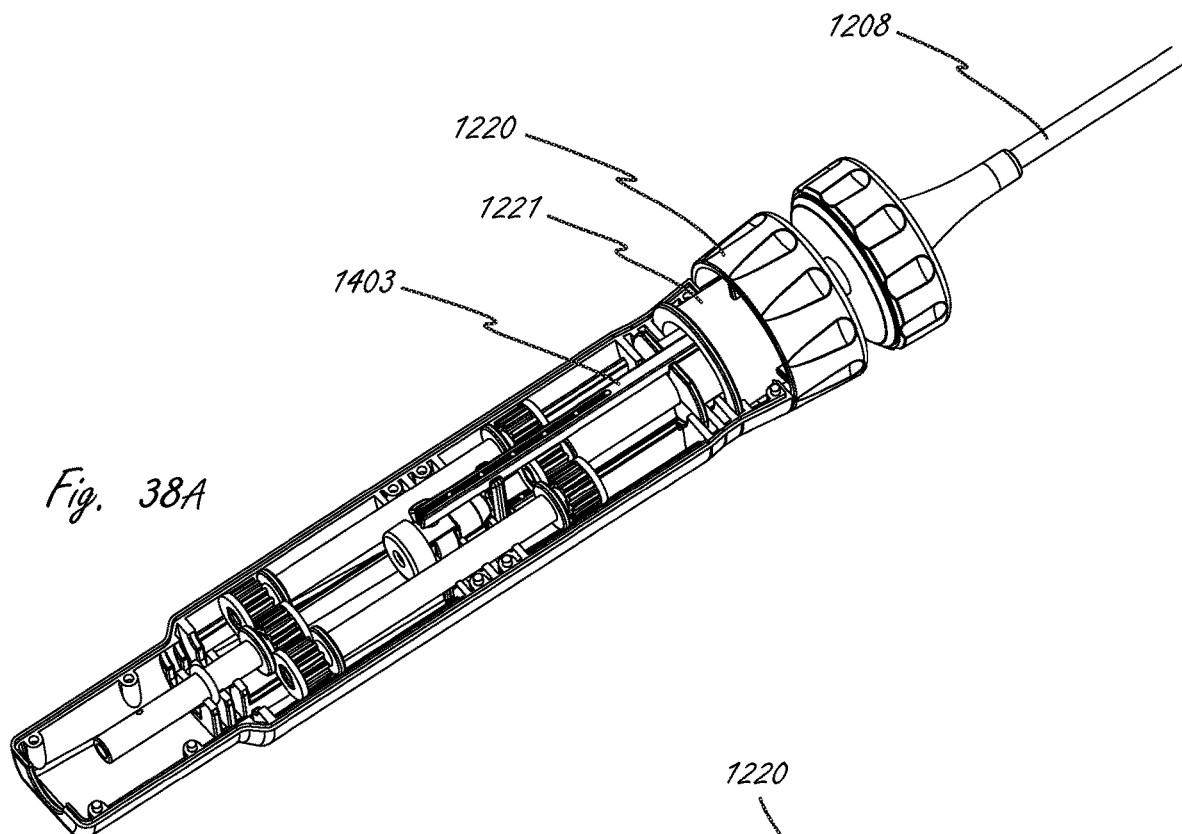
FIGS. 38A and 38B illustrate an exemplary embodiment of a handle assembly.
Figure 38B:
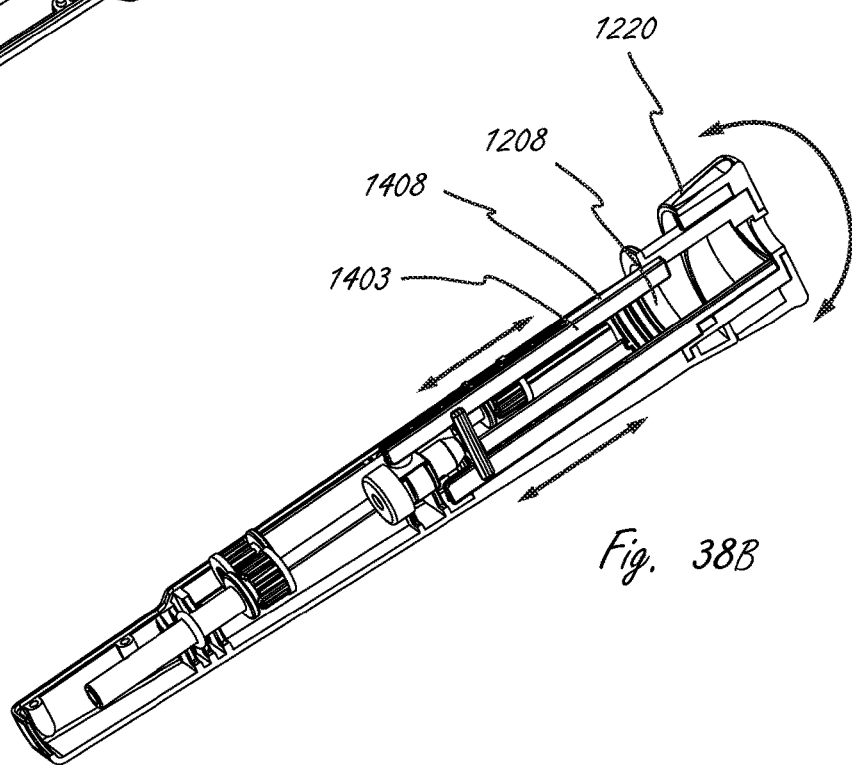

FIG. 37A illustrates an embodiment of the system 1200 with the top half of handle shell 1206' removed to visualize internal components. The steering actuator 1220 may be rotated, which drives pull wires (not shown) exiting from near the proximal end of shaft 1208 (just distal to the hemostasis valve assembly 1950). In some embodiments, the pull wires can exit the shaft and be routed distally and then wrapped around the barrel 1221 (see FIG. 38A) of the actuator 1220. In another embodiment, the actuator barrel may be comprised of cams, leadscrews, or ramps which drive longitudinal rods or shafts attached to the pull wires to actuate the pull wires in the axial direction. FIGS. 38A and 38B illustrate an example of a longitudinal movement mechanism as mentioned above. In FIG. 38A, handle shell 1206' has been removed to show the mechanisms of actuation. The steering actuator 1220 drives one or more rods 1403 that travel along an axis parallel to the longitudinal axis (i.e., aligned in the distal/proximal direction) of the outer shaft 1208. One or more pull wires can be attached to each rod 1403. As rod 1403 travels distally and proximally the pull wires 1104 are displaced such that the pull wires are tensioned or relaxed, increasing or decreasing the deflection of 1222. In FIG. 38B, portions of the handle have been removed or sectioned to reveal the concentric helical ramps 1408 on the internal surface of actuator 1220 on which rods 1403 ride. The concentric ramps can be either opposing or similar in direction. The ramps may also vary in pitch.

Figure 39A:
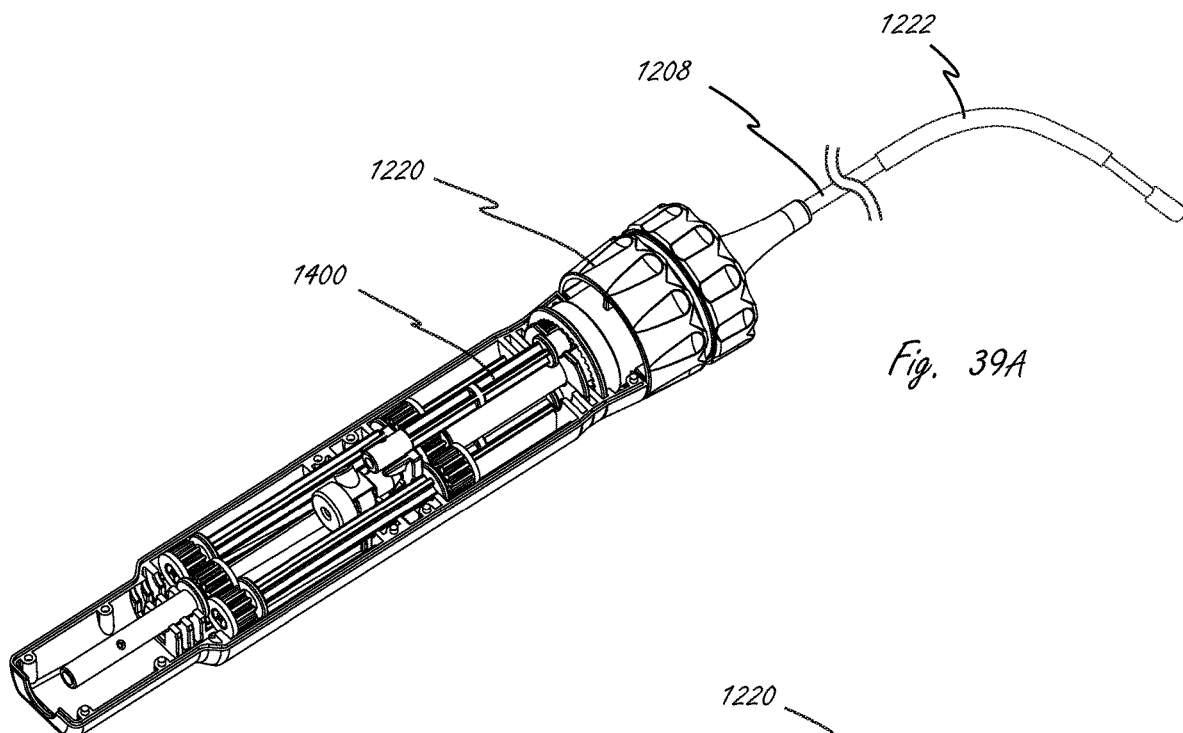
FIGS. 39A-E illustrate an exemplary embodiment of a handle assembly, including steerable sheath control.
Figure 39B:
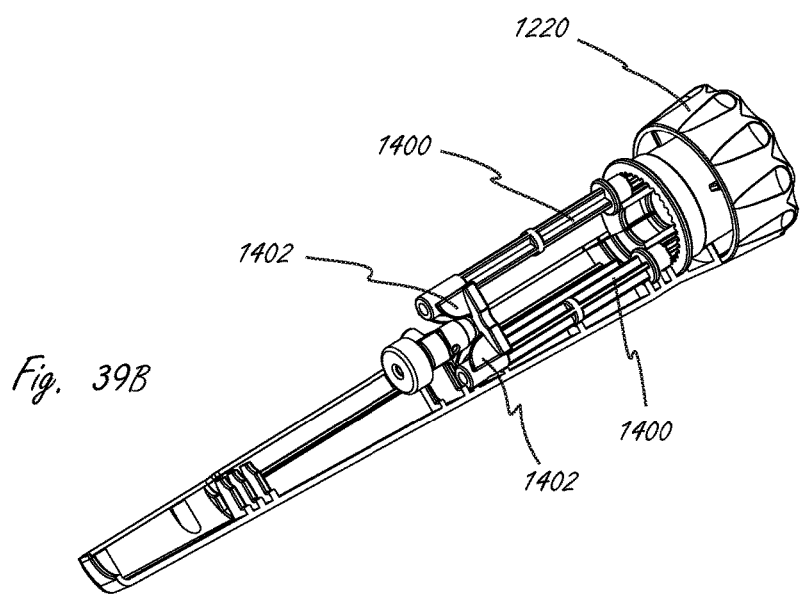
Figure 39C:
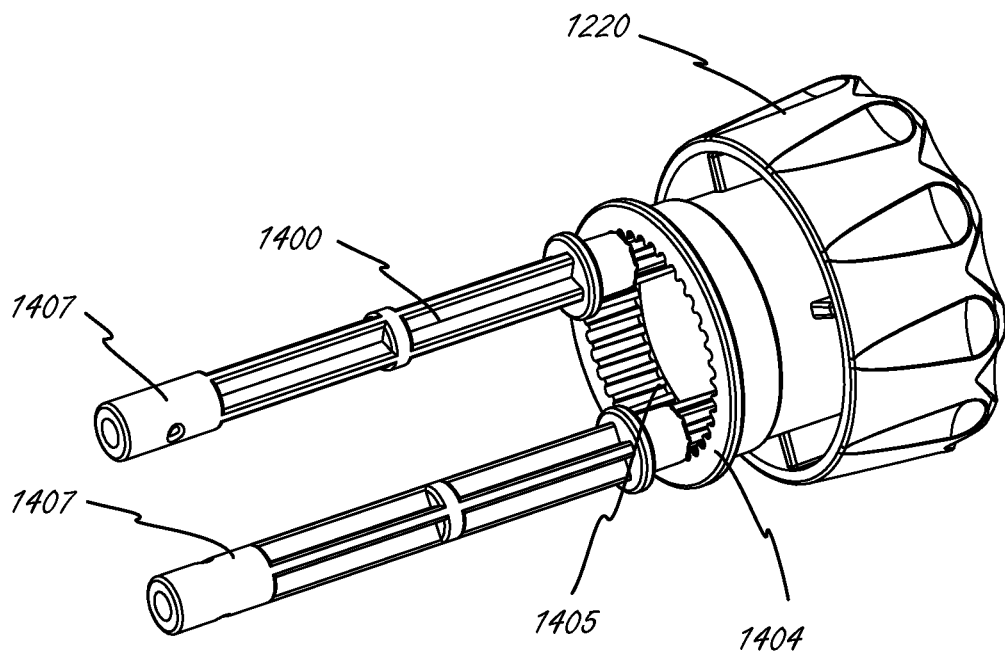
Figure 39D:
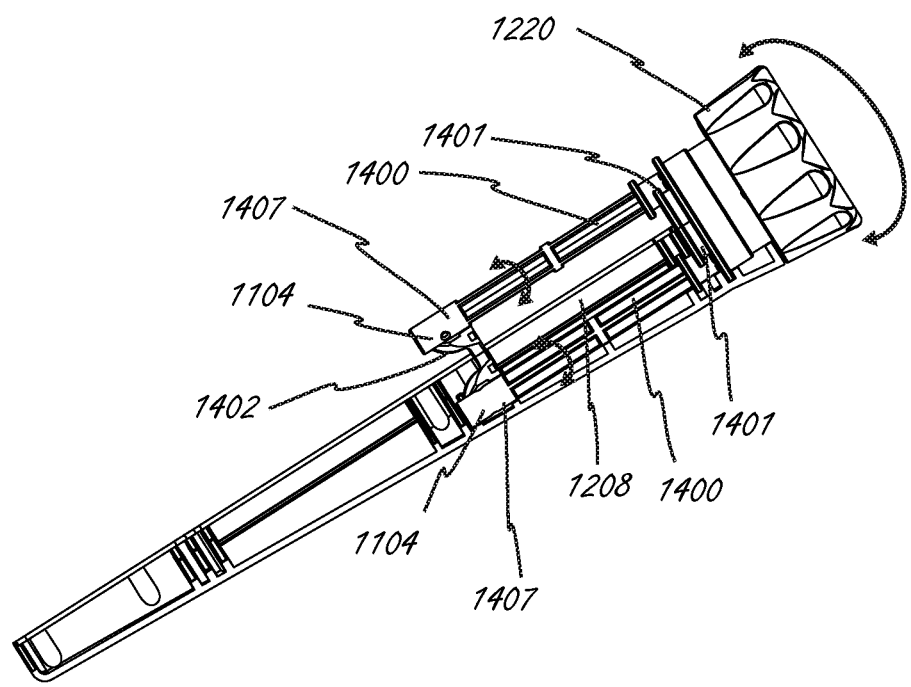

FIGS. 39A-39E illustrate an alternate steering mechanism embodiment, which may also be referred to herein as a control system. In FIG. 39A, handle shell 1206' has been removed to show the mechanisms of actuation. The steering actuator 1220 is rotated to drive the rotation of one or more spindles 1400 (there are two in this embodiment). As shown in FIG. 39C, internal gear teeth 1404 on 1220 mate with external gear teeth 1405 at the distal end of the spindles 1400 to drive the rotation of spindles 1400 as shown in FIGS. 39B and 39C. Note that FIG. 39B is shown rotated around the longitudinal axis by 90° relative to FIG. 39A and some components have been sectioned or removed for better visualization of the internal mechanisms. FIG. 39D illustrate pull wire 1104 exiting from the proximal end of the steerable shaft 1208 and then secured to spindles, such that actuation of actuator 1220 causes tensioning/relaxation of the pull wire(s).

Figure 40A:
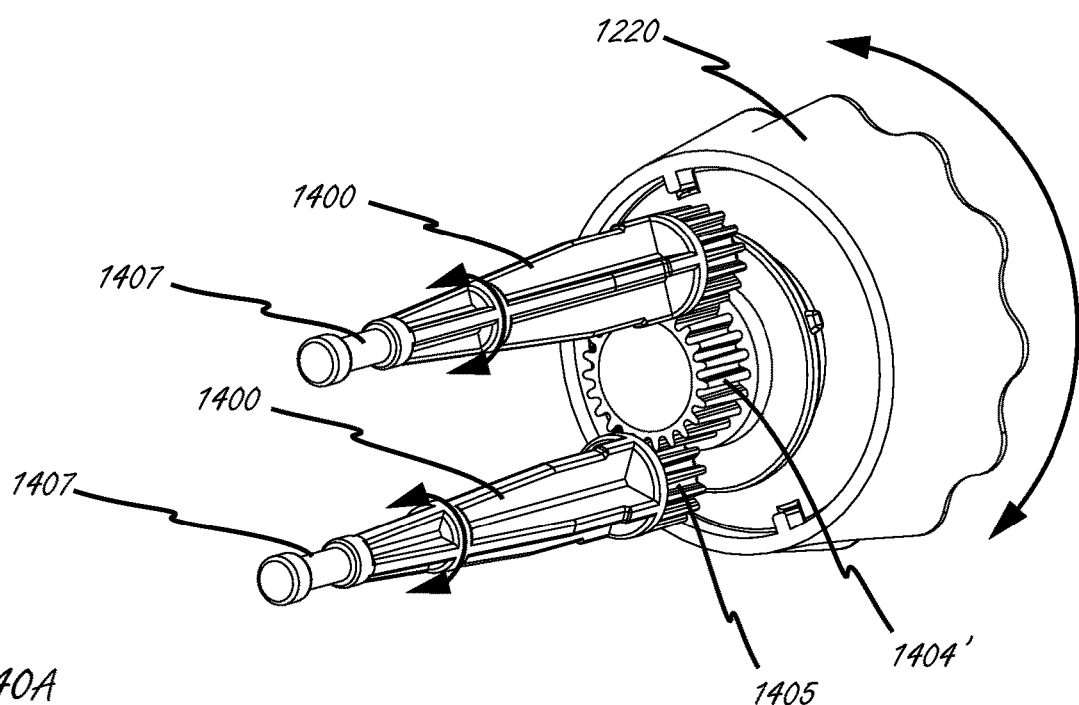
FIGS. 40A-B illustrate an exemplary aspect of a steerable sheath control mechanism.
Figure 40B:
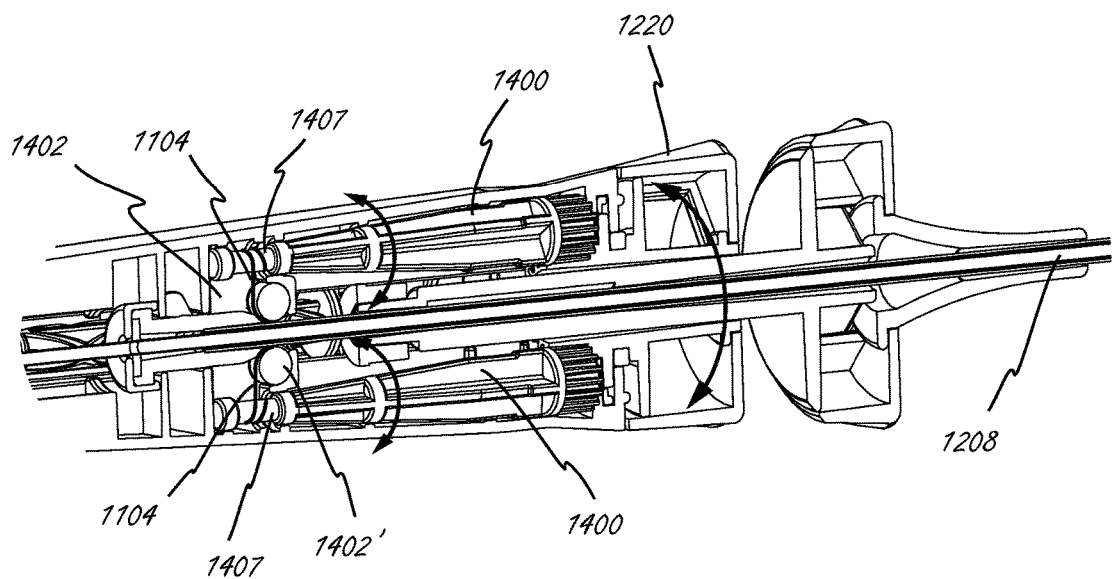

FIGS. 40A-40B illustrate a similar but alternate steering mechanism embodiment where external gear teeth 1404' coupled to steering actuator 1220 are provided instead of the internal gear teeth 1404 illustrated in FIG. 39C. The external gear teeth 1404' engage the external gear teeth 1405 located at the distal end of spindle 1400. Other features of the system can be any of the embodiments described herein.

Figure 39E:
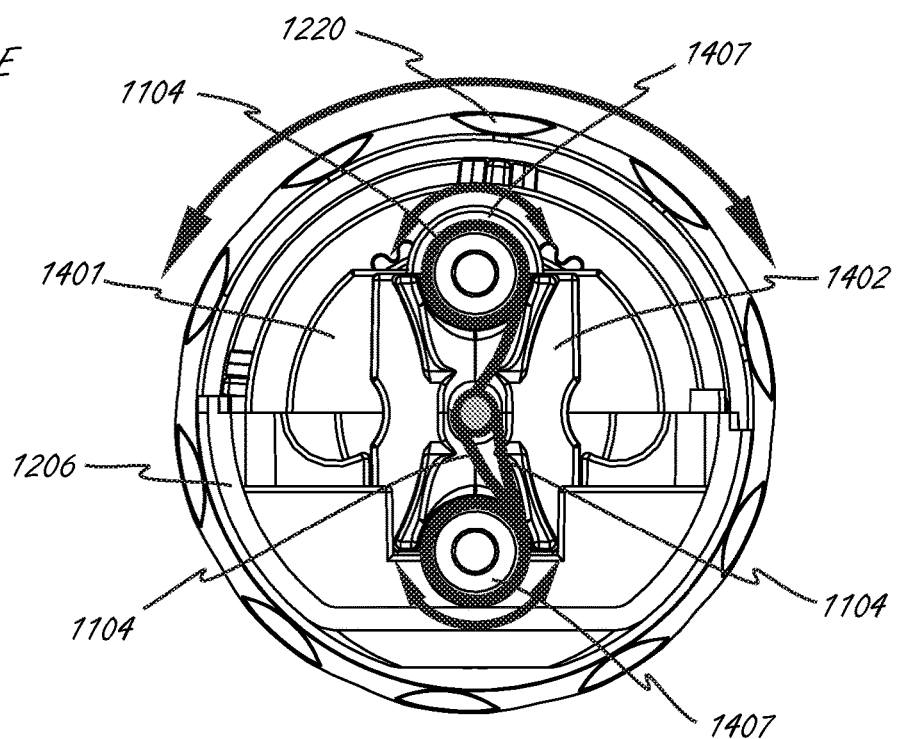

As shown in FIGS. 39D and 39E, when actuator 1220 is rotated, pull wires 1104 spool onto or off of reels 1407 provided at the proximal end of spindles 1400. Mechanical advantage and steering precision can be increased or decreased by increasing or decreasing the diameters of the external gear 1405 and/or the reel 1407 of spindle 1400. For example, the embodiment illustrated in FIG. 39D has a different mechanical advantage than the embodiment illustrated in FIG. 40B. In an exemplary example, one complete rotation of the 1220 knob as illustrated in FIG. 39D will displace the pull wires 1104 by, for example, 3.59 inches, while one complete rotation of knob 1220 as illustrated in FIG. 40B will displace the pull wires 1104 by only 0.60 inches.

As illustrated in FIGS. 39D and 39E, distal and proximal spindle supports 1401 and 1402 keep the mating gears of actuator 1220 and spindle 1400 engaged. Spindle supports 1401 and 1402 also keep the spindle(s) 1400 fixed in location while still allowing axial rotation of actuator 1220, knob shaft 1231, and spindle(s) 1400.

FIGS. 39D, 39E, and 40B illustrate the routing of pull wires 1104 starting at the point they exit the outer deflecting shaft 1208. The pull wires 1104 exit shaft 1208 and route through the proximal spindle support 1402. As illustrated in FIG. 39D, a large radius bearing surface is integrated into spindle support 1402 to limit the abrasion of the pull wires as they route around the 90 degree turn. The radius is oriented to begin as a near tangent to the exit point of the pull wire from the shaft to minimize any loading away from the central axis of the pull wire lumen as the pull wire exits the shaft. As illustrated in FIG. 40B, the large radius bearing surface is provided by a dowel pin 1402' incorporated into spindle support 1402. In another embodiment, not shown, the bearing surface could be a pulley wheel which rotates on its own spindle as the pull wire advances around the wheel surface. The bearing surfaces could be a comprised of polished metal or a low friction polymer known in the art including, but not limited to, Delrin, Polyethylene, or Teflon. In these embodiments, two pull wires are spooled on one reel and one pull wire is spooled on the other reel. Alternate embodiments may have more or fewer pull wires, reels, and spindles. Alternate embodiments may have more than two pull wires spooled on a reel.

The embodiments above describing steerable sheath control can be incorporated into any of the handles and systems herein, and can be integrated with any of the medical tool control mechanisms herein.

The handle assemblies herein are also adapted to be able to allow for actuation of the tool, such as rotation and axial movement. Some embodiments herein include a distal actuator that controls the medical tool, and the handle mechanism allowing for the control extends further proximally than the proximal end of the steerable sheath and the valve.

FIG. 37B illustrates an exemplary handle 1206 with the half of the handle shell 1206' and the actuator 1220 removed in order to illustrate how the tool actuator 1230 is in operable communication to the proximal tool portion 1212. In this embodiment, knob 1230 is attached to knob shaft 1231 which drives (is in operable communication with) distal central gear 1235. The distal central gear 1235 is coupled to (in operable communication with) distal lateral gears 1236 which drive the lateral shafts 1237, which in turns drives proximal lateral gears 1238. The proximal lateral gears are coupled to (in operable communication with) proximal central gear 1239, which drives proximal central shaft 1240. The tool portion 1212 is bonded within shaft 1240. The handle 1206 is designed such that the tool drive assembly (components 1230-1240) is axially slidable in the distal/proximal directions as a unit (double arrows in FIG. 37B) to advance and retract the tool 1212 in the axial direction. The knob shaft 1231 and distal central gear 1235 are adapted to spin freely around the outside of the outer shaft 1208 of the steerable shaft that extends proximally within the handle until where it is affixed to the hemostasis valve assembly 1950. The lengths of the lateral shafts 1237 allow the axial translation of the knob assembly around the fixed position of the hemostasis valve assembly 1950, which is disposed at the proximal end of the steerable shaft. FIG. 37B illustrates two lateral gears and shafts which provide symmetry and balance to the mechanism; however, the assembly could be configured with a single lateral gear mechanism, or a larger plurality of gears around the inner circumference of the handle. The gears are shown with a tooth-engagement mechanism, but a tensioned friction belt mechanism and other means known in the art are contemplated. The steering actuator 1220 and/or took knob 1230 may also be coupled to a friction mechanism to hold position of the pull wires or tool shaft until actuated further. Compression o-ring or gasket seals, low friction bearings, and the like which have a constant interference force or have a mechanism to increase and decrease the locking force by means known in the art are contemplated. Removal and replacement of such seals and bearing surfaces may also be necessary as part of the reposing process.

Any of the tool control mechanisms herein can be integrated with any steerable shaft control mechanisms herein.

Figure 42A:
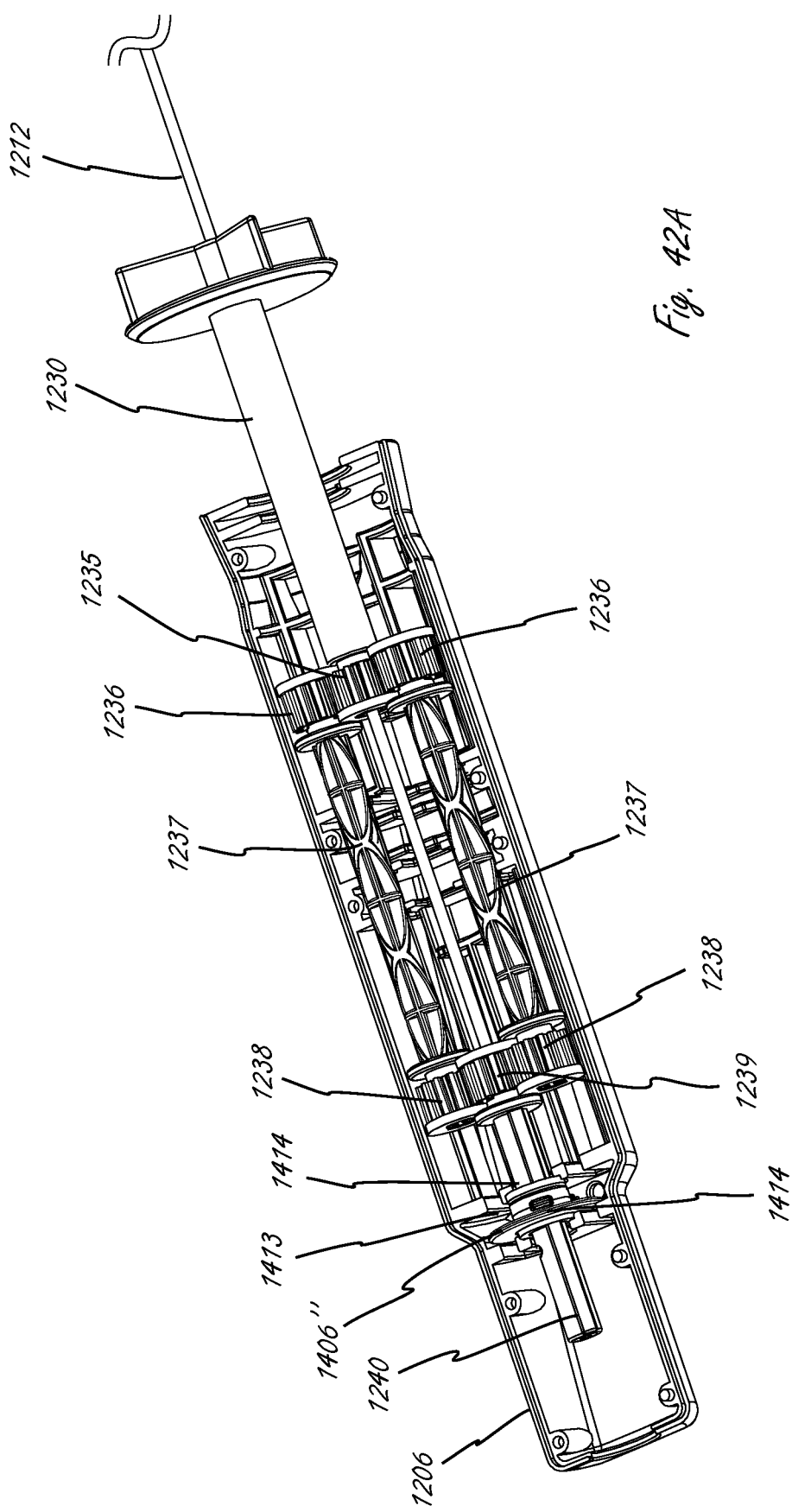
FIGS. 42A and 42B illustrate an exemplary probe control system within an exemplary handle assembly.
Figure 42B:
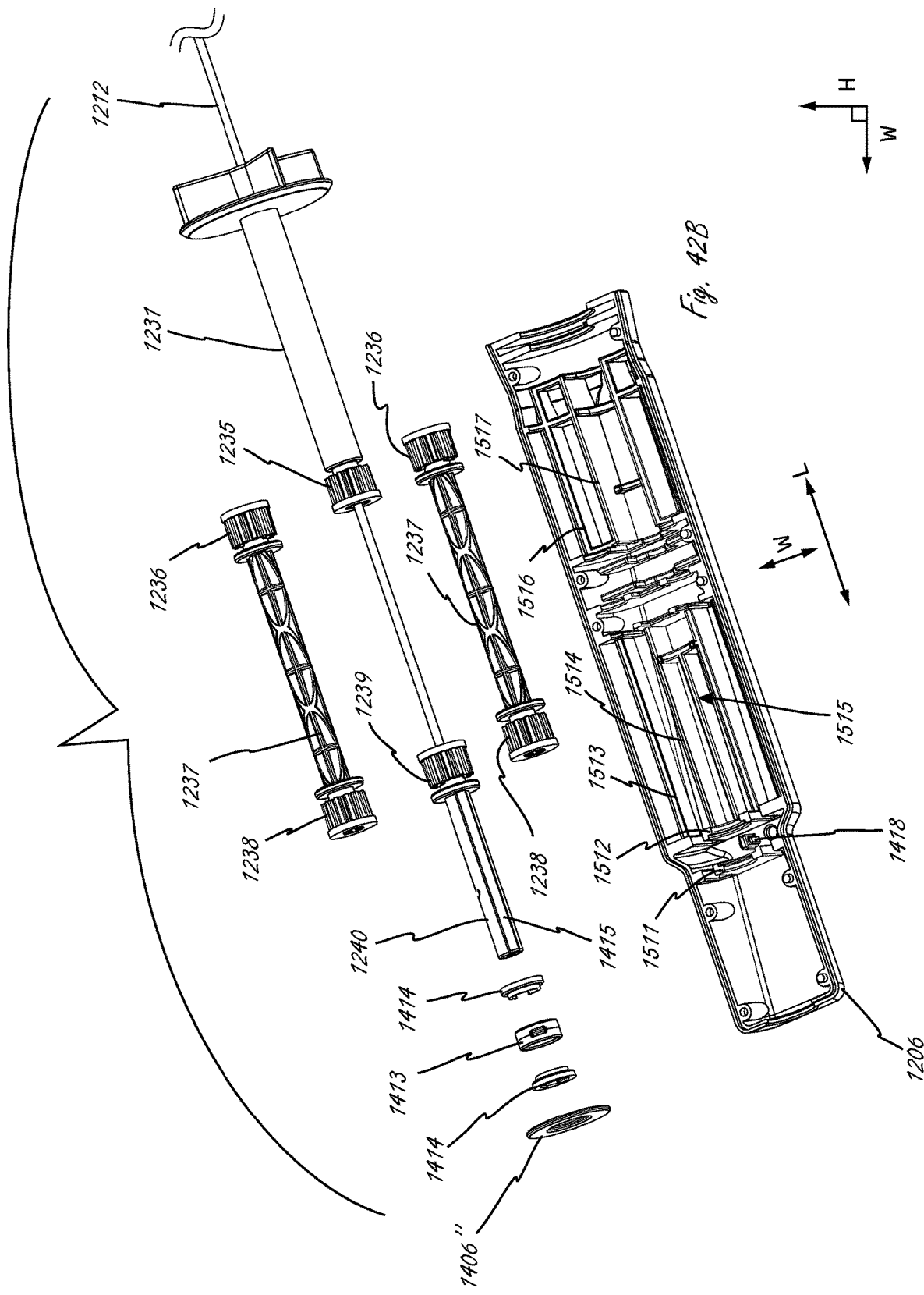

FIGS. 42A and 42B (42B is an exploded view) illustrate components constrained by handle shell 1206 that are critical for tool steering. The steerable shaft and controls are either not included or not labeled for clarity. Tool steering components that are constrained by 1206 include components identified by the following numerical references: 1240, 1414, 1413, 1239, 1238, 1237, 1236, and 1235. Tool control shaft 1231 is indirectly constrained by handle shell 1206 but is critical to the function of the tool rotation and will be referenced in this section. FIG. 42A shows just the tool steering components constrained by 1206 in their assembled state. FIG. 42B shows the same components in FIG. 42A in an exploded view, which helps illustrate how the parts fit within the handle shell 1206. Central shaft 1240 and attached gear 1239 are constrained by spacers 1414, tool rotation limiter 1413, and 1238 as well as guide 1515 of handle shell 1206. Central shaft 1240 and gear 1239 are constrained as to allow rotation and translation around and along the axis of central shaft 1240. Central shaft 1240 can rotate freely until its rotation is prevented, as described herein with respect to rotation limiters. Spacers 1414 and limiter 1413 interface with and are constrained by wall 1511 with recess therein and wall 1512 with recess therein formed integrally as part of handle shell 1206, such that they can only rotate around their central axis, and not axially. Walls 1511 and 1512 can be considered part of a handle body "guide" as that term is used herein. Lateral shafts 1237 and attached gears 1238 and 1236 are constrained by handle shell walls 1513, 1514, 1516, and 1517, which provide bearing surfaces that allow the lateral shafts 1237 and attached gears 1236 and 1238 to rotate around and translate axially along their central axes. Walls 1513 and 1514 are part of a proximal guide in a proximal portion of body 1206, and walls 1516 and 1517 are part of a distal guide in a distal portion of body 1206, both guides being radially aligned and extending along the length of the body 1206 with axes that are parallel to axis of the handle. The walls and guide are integrated into both sides of the handle body, even though the walls are labeled only on one side. Handle shell walls 1513, 1514, 1516, and 1517 are also configured to keep gears 1238 engaged with mating gear 1239 and gears 1236 engaged with gear 1235, while still being free to rotate around and translate axially along their respective axes. These walls and guides, optionally integral to the handle body as shown in this embodiment, are what allow the medical tool to be moved axially and rotated by actuating only the tool knob 1230.

The guides defined by walls 1513/1514 and 1516/1517 are orthogonal to the guide defined by walls 1511/1512.

Central shaft 1240 is an example of a tool lock, as that phrase is used herein, such as in reference to FIG. 8.

The length "L," width "W," and height "H" dimensions that may be used to describe one or more parts in any of the embodiments herein are also labeled. The length is generally measured in the proximal-to-distal direction, orthogonal to both the width W and height H. The length L dimensions can be considered to be measured in a direction that is parallel with a longitudinal axis of the handle assembly and/or shaft portion of the system. The width vs height graph is not intended to apply to the view in the figure, it merely shows the orthogonal nature of the width and height dimensions.

Figure 43A:
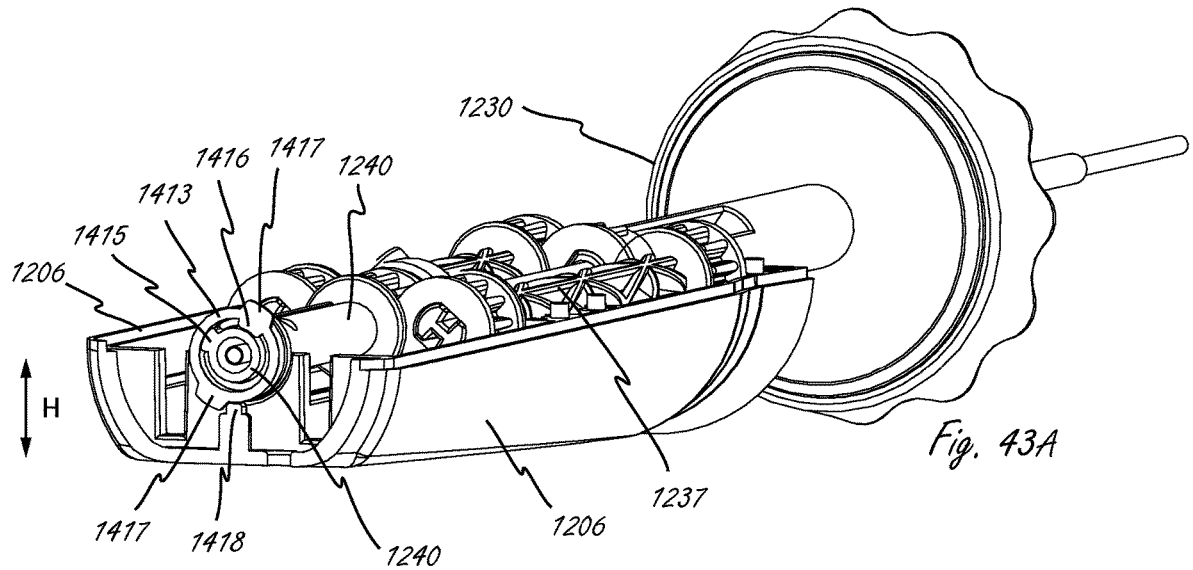
FIGS. 43A-C illustrate an exemplary portion of an exemplary probe control system.
Figure 43B:
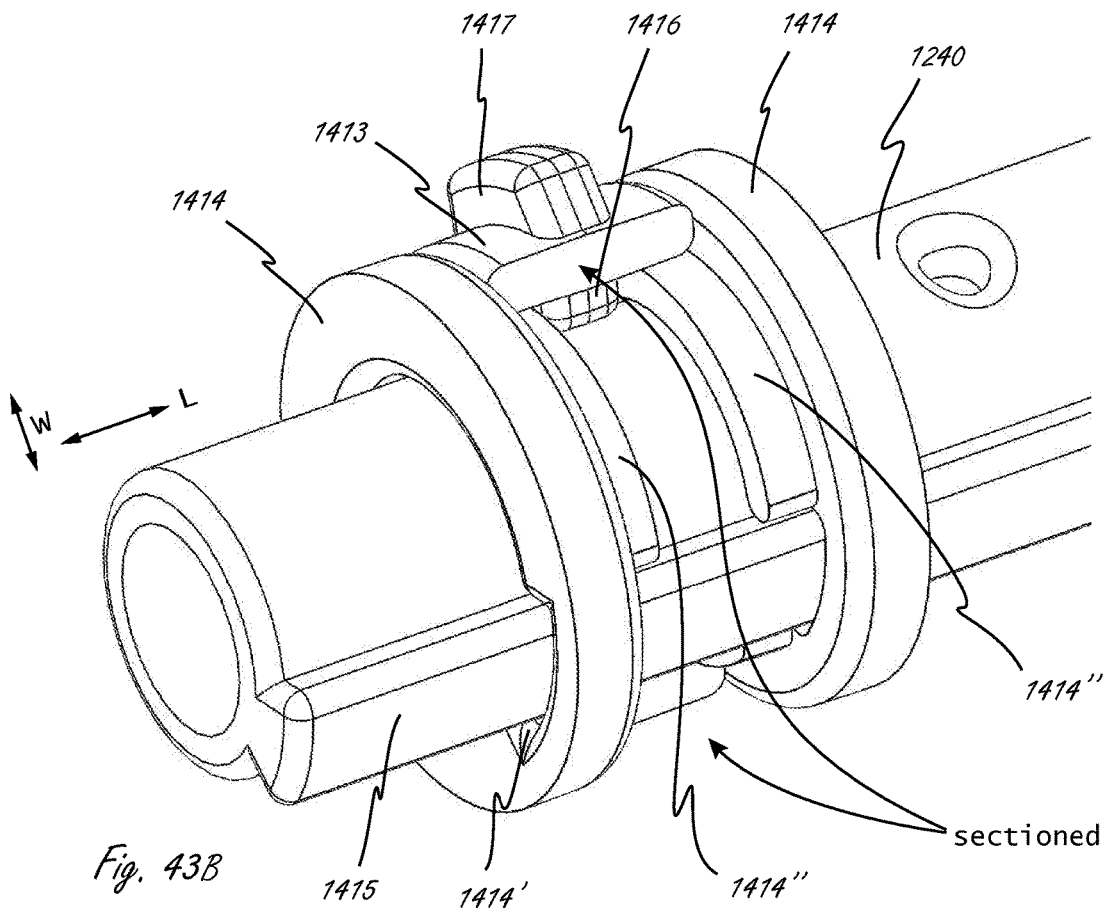
Figure 43C:
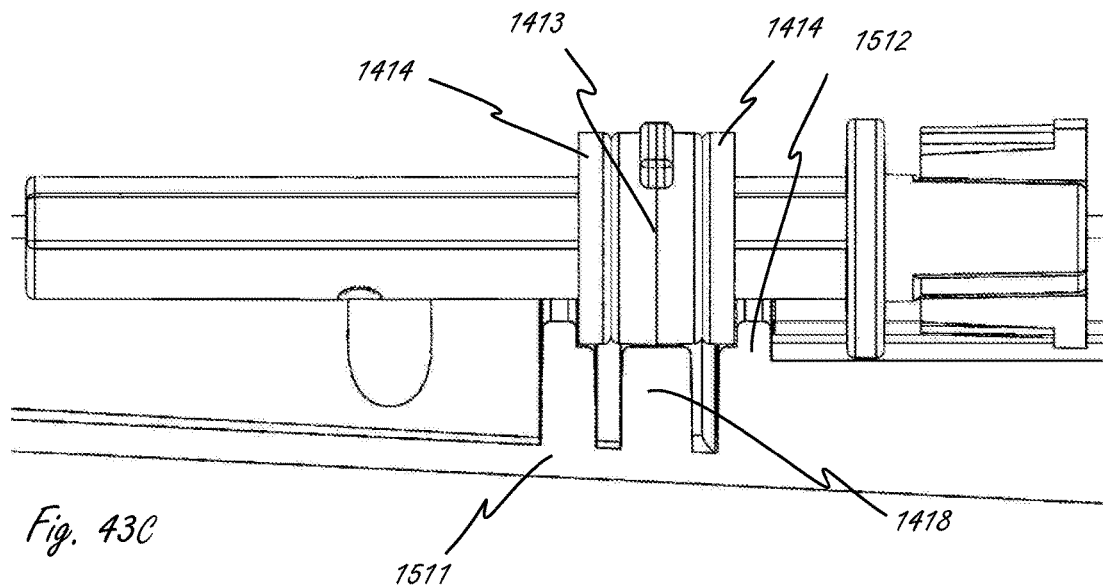

As previously described herein, such as in reference to FIG. 10B, the rotation of the tool can be limited. FIGS. 43A-43C illustrate an alternative embodiment of the medical tool actuator rotation limiter which allows a limited total rotation exceeding 360 degrees. FIGS. 43A-43C illustrate the rotation limiting components that are in the embodiment in FIGS. 42A and 42B. FIG. 43A is a section view, FIG. 43B is a perspective view that shows only a portion of the system and 43C is a side view showing interaction the handle shell. As illustrated in FIG. 43B (assembled, 1413 sectioned) and FIG. 42B (shown exploded), the embodiment includes limiter 1413 and first and second spacers 1414 positioned distal to and proximal to, respectively, limiter 1413. Each spacer 1414 is formed with an inner key slot 1414' (see FIG. 43B) that allows it to axially slide over and rotate with the embossed key feature 1415 (similar concept to keyed feature 1956 previously described) integrated into central shaft 1240 (similar concept to tool lock 1955 previously described). The spacers 1414 are also formed with an inner radial lip 1414" extending axially inside the inner diameter of the limiter 1413, providing uniform support for the limiter 1413, allowing it to spin freely over the central shaft 1240. FIG. 43A illustrates the assembly disposed in the handle shell 1206', with the end of the figure shown as a cross-section through limiter 1413. When the actuator knob 1230 is rotated, the rotation is translated through lateral shafts 1237 to central shaft 1240. Actuator knob 1230, shaft 1240, and key feature 1415 will rotate freely until the key 1415 contacts the internal nub feature 1416 (see FIGS. 43A and 43B) on the rotation limiter 1413. Actuator knob 1230, shaft 1240, and limiter 1413 will rotate freely until the two external nub features 1417 on limiter 1413 contact the internal limiter 1418 integrated into the handle shell 1206'. The two spacers 1414 keep limiter 1413 concentric with shaft 1240. Importantly, the proximal compound rotation limiter is also adapted to allow for axial translation of shaft 1240, which is important to allow the medical tool to be moved axially. The degrees of allowed rotation can be adjusted by increasing or decreasing the position and/or circumferential extent of one or more of the nub features 1415, 1416, 1417, and 1418. Additional radially nested rings with nubs could also be added to compound the number of allowed turns. In other embodiments the nubs could be formed additionally or instead in the axial direction to allow compounding of rotations by adding engagement rings in the axial direction. FIG. 43C shows a side view of some of the components of the system for clarity, including limiter 1413 and limiter 1418 integrated into the handle shell.

FIG. 43A also illustrates the direction H of height measurements for any of the components therein, such as the height of rotation stop 1418. FIG. 43B also illustrates the directions W of width measurements and length L of length measurements for any of the components therein.

Figure 44A:
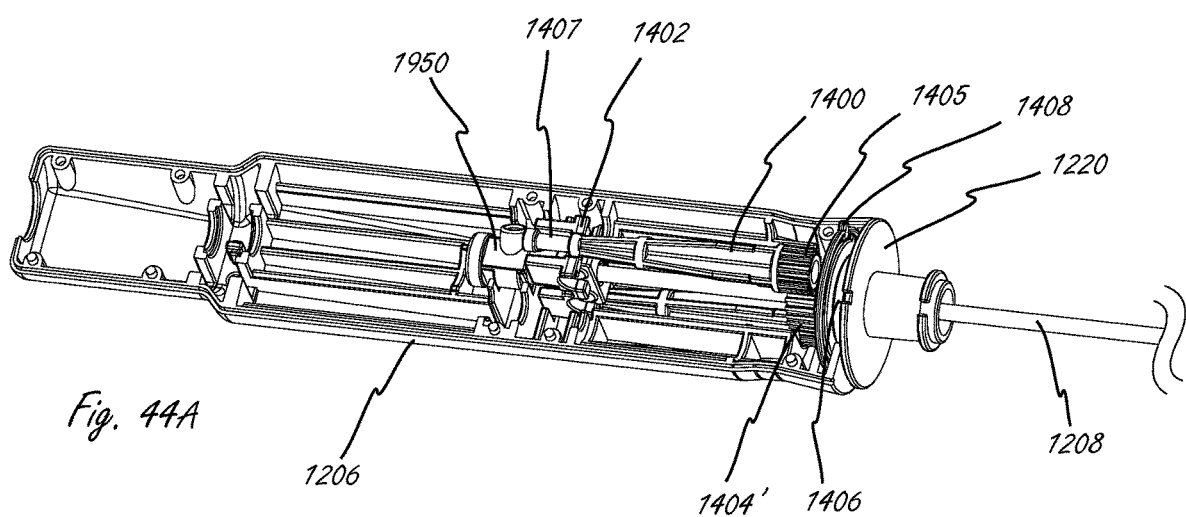
FIGS. 44A-E illustrate an exemplary portion of an exemplary steerable sheath control system.
Figure 44B:
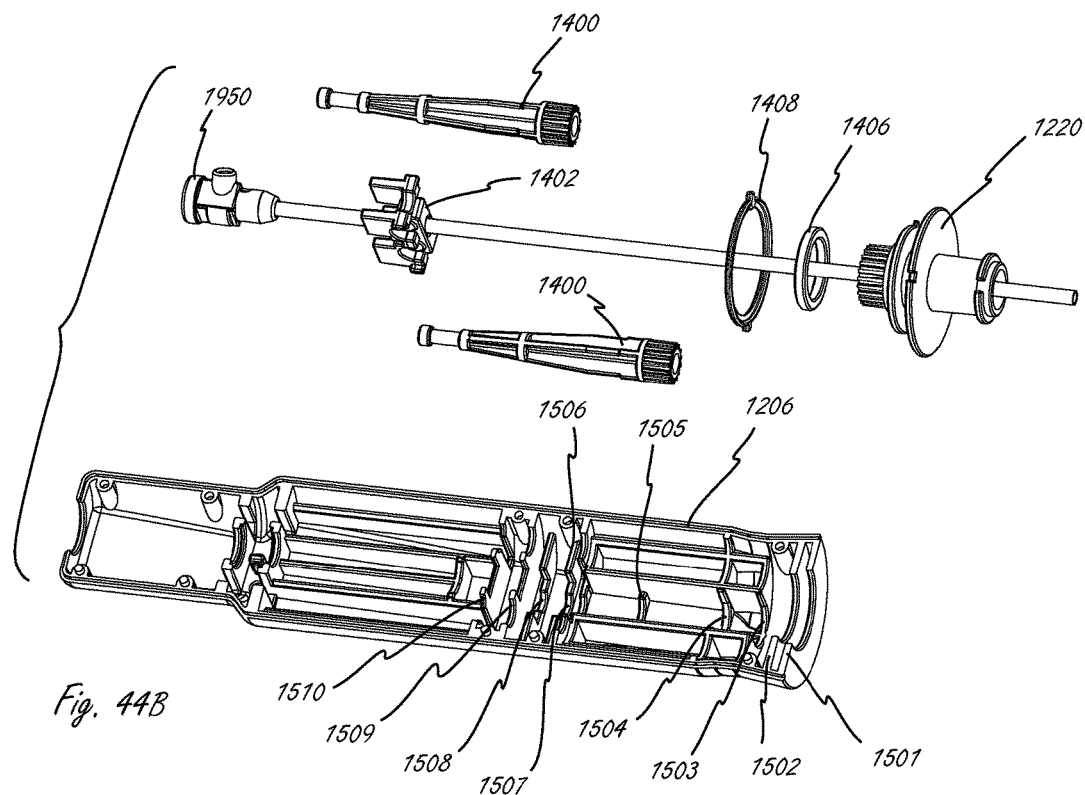
Figure 44C:
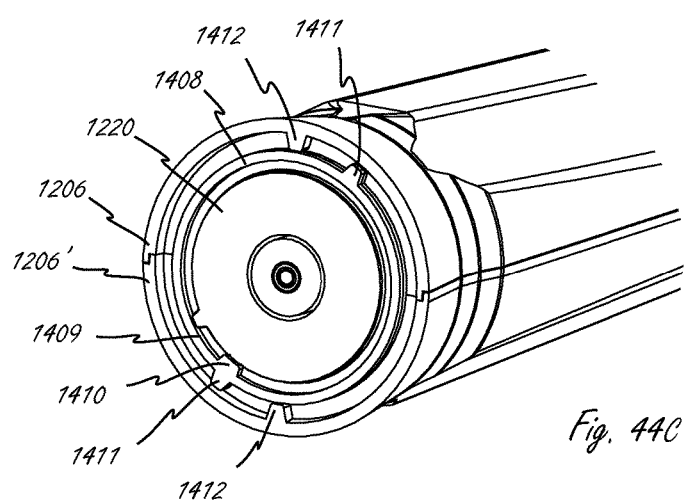

FIGS. 44A-44C illustrate deflection actuator knob rotation limiter 1408 for limiting rotation when actuation actuator 1220, which operates similarly to the rotation limiter for the medical tool. This compound rotation limiter allows for greater than 360 degrees of rotation of the deflection actuator knob 1220 before hitting the rotation limiter hard stop. When the actuator knob 1220 is turned, the nub feature 1409 rotates with the actuator knob. Actuator knob 1220 and nub feature 1409 will rotate freely until 1409 contacts the internal nub feature 1410 on the rotation limiter 1408. Actuator knob 1220 and nub 1408 will rotate freely until the two external nub features 1411 contact the internal nub features 1412 on the handle shells 1206'. The degrees of rotation can be adjusted by increasing or decreasing the position and/or circumferential width of one or more of the nub features 1409, 1410, 1411, and 1412. Additional radially nested rings with nubs could also be added to compound the number of allowed turns. In other embodiments, the nubs could be formed additionally or instead in the axial direction to allow compounding of rotations by adding engagement rings in the axial direction.

Figure 41:
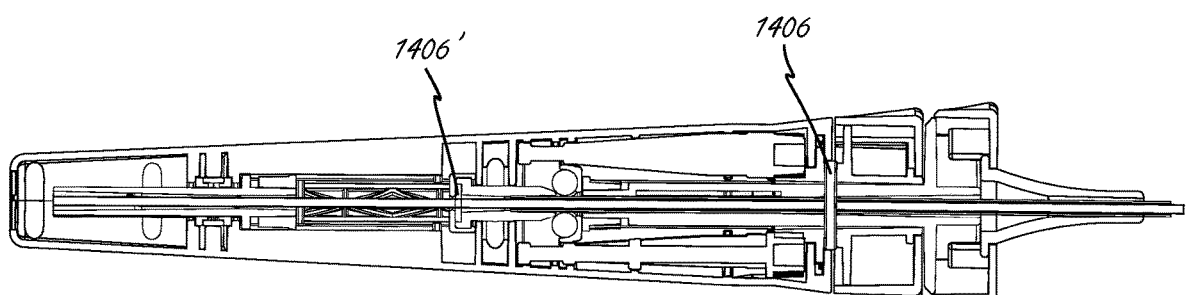
FIG. 41 illustrates exemplary gaskets.

FIGS. 44B and 41 illustrates gaskets 1406 and 1406' that adds friction to eliminate unwanted rotation or translation of the actuator knobs when the handle is jostled while not being held or not in use. A controlled compression of gasket 1406 between deflection actuator knob 1220 and shell 1206' provides friction to prevent relaxation of the knob 1220 after rotation. Gasket 1406' adds similar controlled compression friction tool 1212 which is coupled to the probe actuator knob 1230. Note that gasket 1406' may be identical to the seal used in the hemostasis valve 1950.

Other embodiments for controlling the friction of the probe actuator knob 1230 could include ways of controlling the friction of the central shaft 1240 coupled to the probe actuator knob 1230. The central shaft 1240 is an exemplar of a tool lock, such as tool lock 1955 previously described, and the frictional control of tool lock 1955 previously described is applicable to central shaft 1240 as well the interface between the deflection actuator 1220 and shell 1206'.

Figures 45A, 45B:
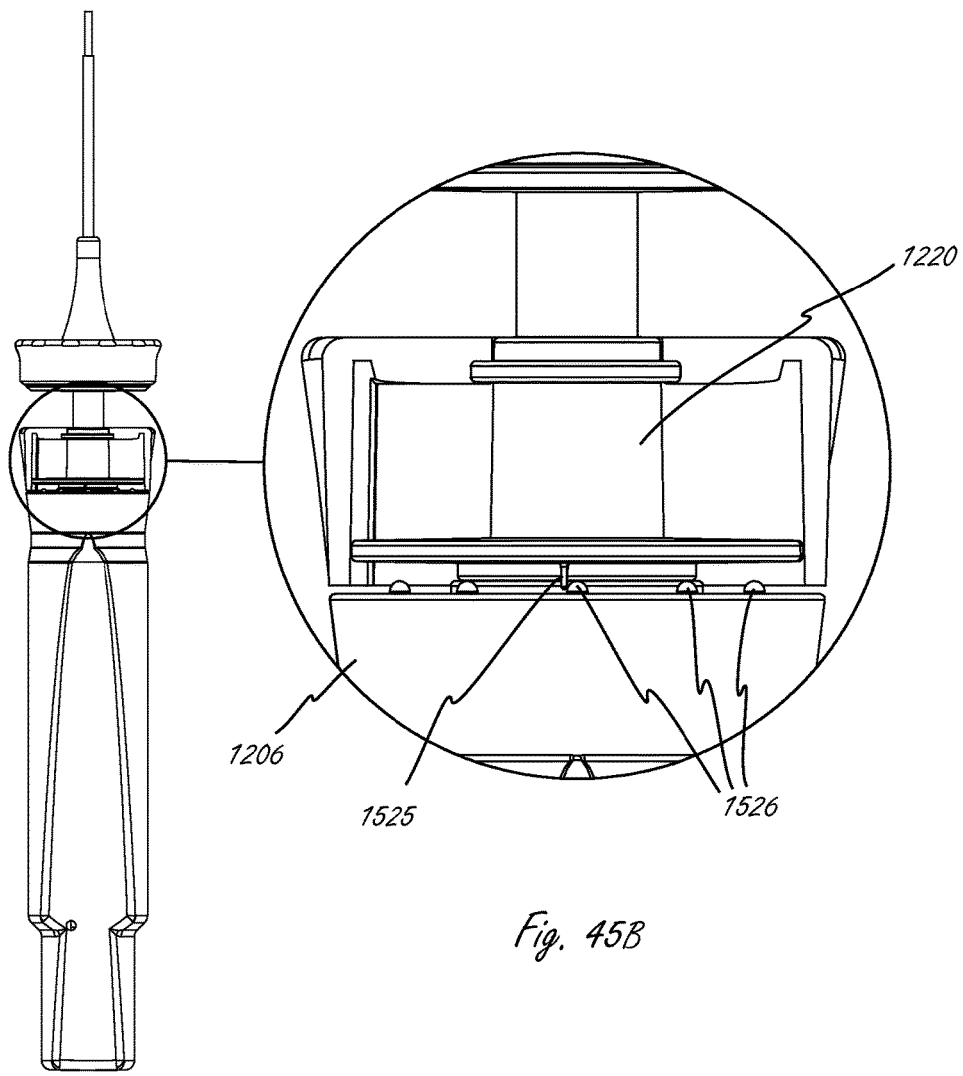
FIGS. 45A and 45B illustrate an exemplary combination of audible and/or tactile cue features incorporated into a knob to signal the position of the knob relative to a neutral start position or a stop position.

The actuators that control the steerable shaft and the medical tool (e.g., knob 1230 and deflection actuator knob 1220) may be provided with features that allow the user to intuitively understand the relationship between the two. When the system 1200 is provided to the user, the steerable sheath 1202 is straight, meaning the deflection actuator 1220 is in a preferably neutral, or home, position where tension is not applied to the one or more pull wires 1104. Similarly, the tool knob 1230 is in a neutral, or home, position, where the tip attached to the distal end of the medical tool is in a position set during manufacturing. For example, the home position of tool knob 1230 may be pulled back against (or slightly offset from) the distal end of deflection knob 1220 and rotated to a given position such that the proximal end of the tip (e.g., tip 3000) is against (or slightly offset from) the distal end of sheath portion 1208, and also such that the transducer is (if part of the device), by way of example only, in a rotational position such that the active surface is directed opposite the direction of deflection of the sheath portion 1208. A mechanical stop of the proximal central shaft 1240 (similar to tool lock 1955), to which the proximal end of the medical tool is attached, against features in the handle shell 1206', or other components in the handle, provides a desired proximal retraction offset (e.g., 0.5 mm to 3.0 mm) between the proximal end of the tip of medical tool and the distal end of sheath 1208, as well as a distal travel limit for the extension of tool 1212 and the tip. The communication of the home positions of the tool knob 1230 and deflection knob 1220 relative to the stationary handle body, more specifically the handle shell 1206', may be communicated with visual features such as markings and/or embossed or recessed features on each knob 1220 and 1230 and the exterior of the handle shells 1206'. In one exemplary embodiment, these visual features all align when in the home position. The raised or recessed markings also provide tactile cues to the user regarding the relative positions of the knobs. As illustrated in FIG. 45A and the highlighted view in FIG. 45B, where the knob 1220 is sectioned for clarity, a combination of audible and/or tactile cue features 1525 and 1526 can be incorporated into the knob 1220 to signal the position of the knob 1220 relative to a neutral start position or a stop position. For example, a cantilevered arm 1525, may be allowed to flex or hinge relative to its attachment point as its free end moves up over (or, in other embodiments, down into) another feature 1526 which it moves relative to. This motion creates audible and or vibratory "snaps" or "clicks" as the features 1525 and 1526 interact. The audible/tactile features could be built into either the tool knob 1230 or the deflection actuator knob 1220. In another embodiment, cantilevered arm 1525 could also be incorporated against features moving within the handle shell, such as the rotating gear teeth 1404' and/or 1405 in FIG. 40A, or the rotating gear teeth 1235, 1236, 1238 and/or 1239 in FIG. 37B. The rate of actuation of the audible/tactile may be continuous, or engage only after a certain range of motion, or accelerate or decelerate as a limit is approached. In the latter example, an embodiment could include an increasing density of features such as 1526 against which a cantilevered arm 1525 contacts.

As noted above in relevant embodiments, the medical tool is bonded within proximal central shaft 1240. This is an embodiment similar to the function of the tool lock described herein. In particular, there is benefit to providing a way to reversibly attach the proximal central shaft 1240 (similar to tool lock 1955) such that the tool portion 1212 may be released from the shaft 1240. This release allows the tool portion 1212 to be advanced forward beyond its normal operational advancement limit, or to be completely removed. Advancement beyond normal limits may facilitate cleaning or repair of the tool portion 1212, particularly for the distal end, without the need to fully remove the shaft (which requires disconnection of the flex bundle 2020 from the PCB 2030 as described herein). For example, the distal end of tool portion 1212 may have a lubricious coating applied to the shaft over a certain length (e.g. without limitation, 3-15 cm, preferably 10 cm) which wears off and/or becomes contaminated with bodily fluids during use. In order to clean the shaft properly during the reposing process, the coating may need to be removed and reapplied. Advancing the shaft distally approximately 12 cm (preferably, in this example) would allow physical access to the outside of the distal tool portion (previously inaccessible within the distal end of outer shaft 1208 for cleaning and repair. Sufficient slack in the proximal conductor bundle could be provided to allow advancement of the tool portion 1212. In other examples, the distal portion of tool 1212 could have other features attached to it, such as an o-ring seal, keyway, or swellable hydrogel, that occupy the luminal space between the tool 1212 and inner lumen of shaft 1208, which would not be accessible for cleaning and repair/replacement during the reposing process without advancement of the tool 1212 beyond its normal operational extension limits. Release of the tool 1212 from the central shaft 1240 also provides for complete removal of the inner shaft, provided the flex bundle 2020 is disconnected from one or more PCB 2030 as described in FIG. 20A-C.

In another embodiment, the proximal portion of steerable shaft 1208, proximal to where it would enter an introducer sheath inserted into a patient, could have an enlarged inner and outer diameter which would accept an enlarged outer diameter of the proximal end of tool 1212 (particularly a portion enlarged for the purposes of releasing it from the central shaft 1240 as described below). The enlarged proximal inner lumen of shaft 1208 would allow a sufficient advancement of the enlarged proximal shaft of tool 1212 forward beyond its normal advancement limits for the purpose of cleaning and repair noted above.

FIG. 46 illustrates an exploded view showing many of the exemplary components from the embodiments shown in FIGS. 40A-44C. Components may be labeled with the same reference number as in the embodiments above. The components can be assembled and/or function as described in other embodiments herein. FIG. 46 also shows stopcock 1536, flush line tube 1537 routed through flush line port 1539 formed in handle body 1206 and coupled to the valve 1950.

Figure 47:
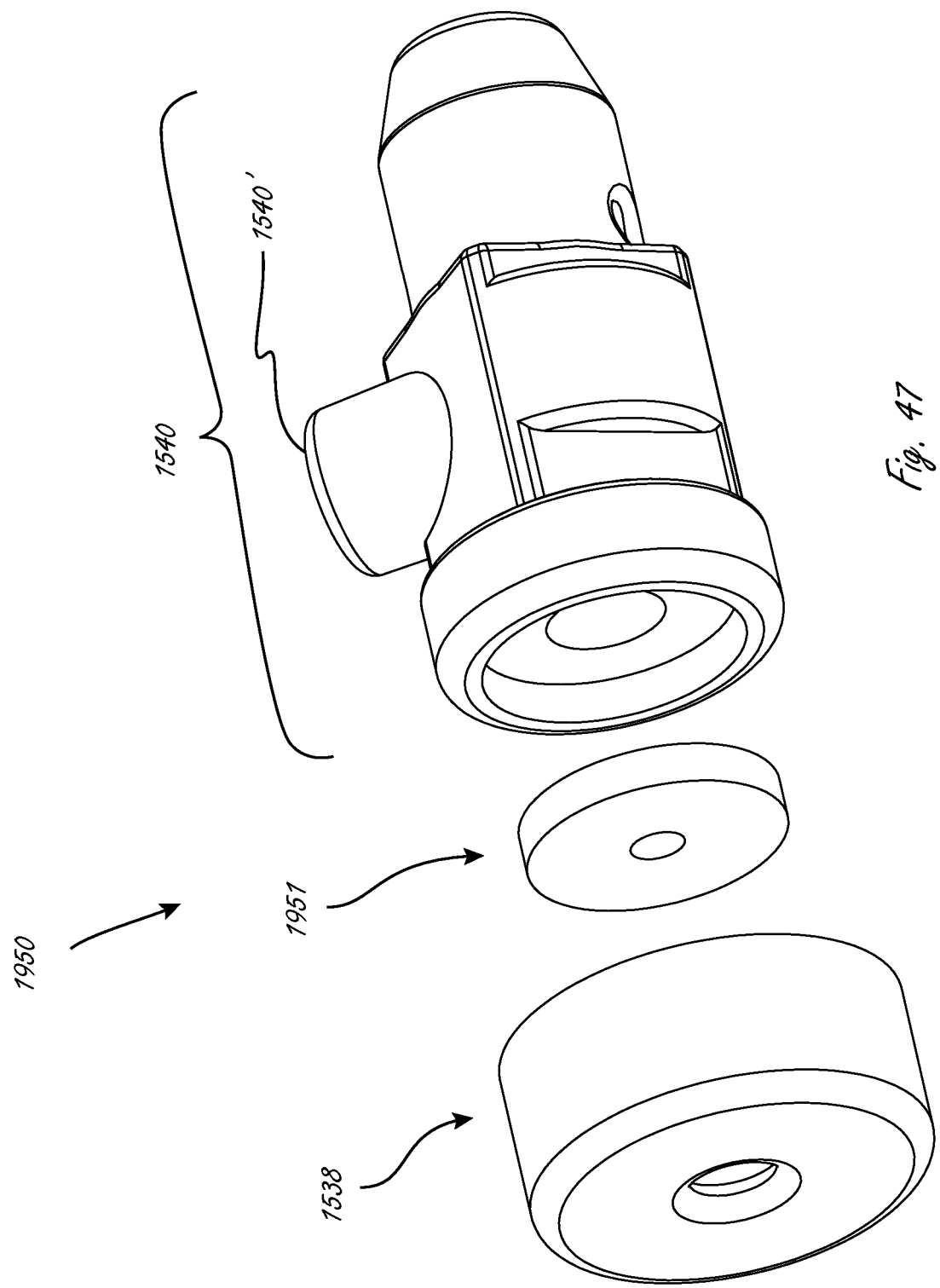
FIG. 47 illustrates an exemplary hemostasis valve.

FIG. 47 illustrates an exemplary hemostasis valve 1950, such as is shown in FIG. 46 including valve body 1540 with integrated flush port 1540' (where a flush line such as line 1537 may be attached), valve seal 1951, and valve cap 1538, where the cap 1538 is designed to constrain the seal 1951 within the valve body 1540. The purge line may be used to purge air from the annular space between the tool 1212 and the inner lumen of the steerable sheath 1208. The proximal end of shaft 1208 can be inserted into the distal end of the hemostasis valve body 1540 and the two can be irreversibly bonded with adhesive. The hemostasis body may be over-molded onto the shaft 1208. The proximal end of shaft 1208 may have a luer fitting (preferably female) irreversibly bonded to it. The distal end of hemostasis body 1540 may also be fitted with a mating luer fitting (preferably male in this case, such as fitting 1952 in FIG. 11A) which is reversibly attached via press fit (or irreversibly attached by press fitting with adhesive) to the female luer fitting on sheath 1208. In this embodiment, the reversible press fit luer would allow removal of the hemostasis valve assembly from the fitting on shaft 1208 during a reposing process.

Figure 49A:
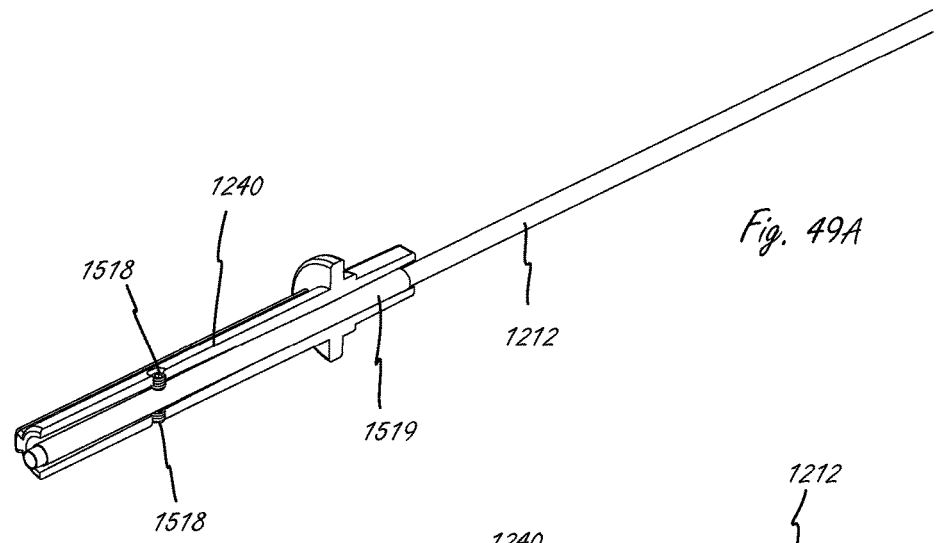
FIGS. 49A-C illustrate various adaptations for reversibly attaching the medical tool from the steerable shaft.
Figure 49B:
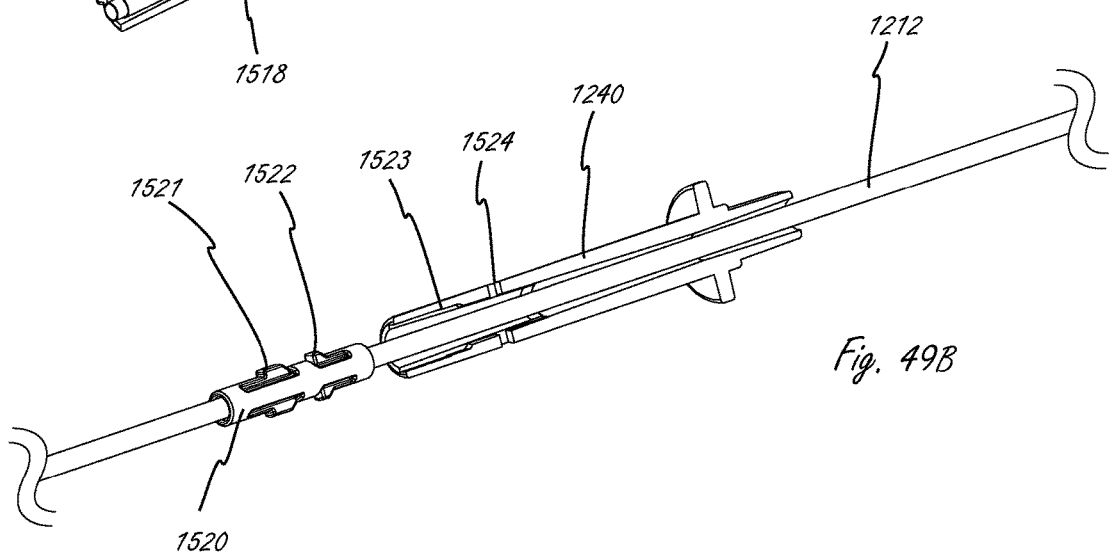
Figure 49C:
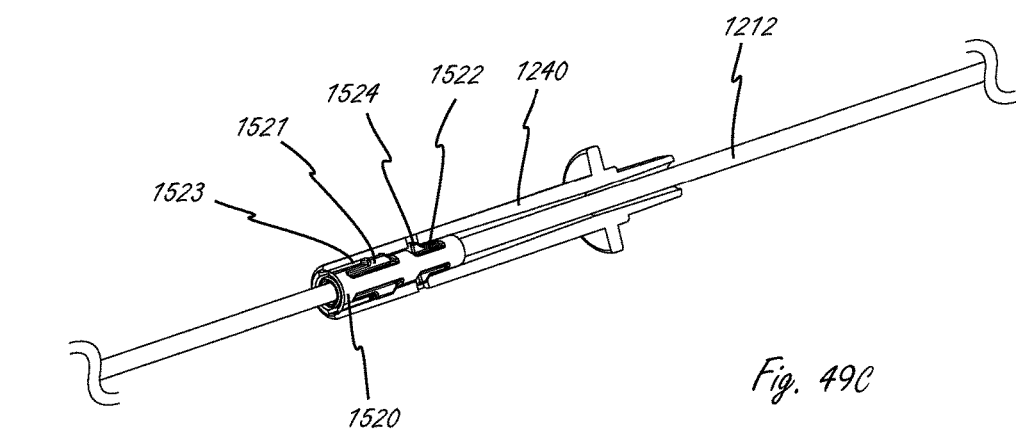

FIGS. 49A-C illustrate various adaptations for reversibly attaching the medical tool from the steerable shaft. In one embodiment, as illustrated in FIG. 49A, an affixing tubular element 1519 is permanently affixed to the proximal end of tool 1212 in a region where it may be coupled to shaft 1240. The affixing tube 1519 provides structural reinforcement to the proximal end of the shaft 2010 (of tool 1212) and is preferably a thin walled metal or stiff polymer tube (e.g., 0.005"-0.010" wall) affixed to the shaft 2010 (e.g., by bonding with adhesive and/or constraining it on either end with heat-laminated polymer tubing such as nylon or pebax). The OD of the affixing tube 1519 is designed such that it will pass through the inner lumen of outer shaft 1208. The shaft 1240 may be constructed of a machined or injection molded plastic or metal. One or more threaded set screw features 1518 may be used to reversibly secure shaft 1240 against affixing tube 1519. Grooves, notches, flats, embossed portions, or other similar features may be provided on the affixing tube 1519 to facilitate compression and interlocking of the set screw 1518 against it. In another embodiment, the set screw 1518 may be replaced with dowel pins. These pins would be held in place by a radial clamp that could be tightened to engage the pins against affixing tube 1518 or loosened to free affixing tube 1519 and tool 1212 from the shaft 1240. In another embodiment, the affixing tube 1519 could be comprised of two half tubes, such as a tube split along its longitudinal axis, each half preferably with slightly less than half the tube circumference, and compressed against the tool shaft 2010 by any of the above described means. This would allow the affixing tube to also be removed from the shaft 2010. In another embodiment, just a single half of the affixing tube 1519 could be used to compress and secure it against the tool shaft 2010 which in turn is compressed against the interior of central shaft 1240. FIGS. 49B and 49C illustrate another embodiment with a snap collar 1520 that when inserted into the inner lumen of central shaft 1240 compresses against tool 1212 (or, in a more specific embodiment, the tool shaft 2010) to reversibly lock the tool 1212 to shaft 1240. Snap collar 1520 has feature 1521 that engages with a tapered channel feature 1523 on shaft 1240 as shown in FIG. 49B. When these features are engaged as shown in FIG. 49C, feature 1521 is compressed by feature 1523, and this compression forces feature 1521 to intrude into the inner lumen of snap collar 1520 which in turn clamps onto 1212, locking tool 1212 to shaft 1240. In addition, when 1520 is fully engaged with 1240, as shown in FIG. 49C, snap feature 1522 engages with receptacle feature 1524. When these features are engaged, snap collar 1520 cannot be rotated within or removed from shaft 1240. To disengage snap collar 1520 from shaft 1240, feature 1522 must be depressed to disengage 1522 from 1524 allowing for 1520 to be removed from the inner lumen of 1240 freeing tool 1212 from snap collar 1520 and shaft 1240. In the above embodiments using snap collar 1520, the affixing tube 1519 could also be bonded over tool 1212 such that the collar 1520 engages the affixing tube 1519.

The inside surface of handle shell 1206' may be constructed with one or more access ports to allow securing or disengagement of the central shaft 1240 from the tool 1212 and/or affixing tube 1519. In one embodiment, this access port may be a hole or channel within a structure embossed radially inward from the inside surface of shell 1206', allowing it to terminate in close proximity to shaft 1240.

Handle shells 1206' have several features that are integral to the function of the handle assembly as a whole. Some of these features anchor components in place while other features allow for rotation of components around central axes and/or for the components to translate longitudinally. Additionally, some features on 1206' are critical to constrain other components such that they remain engaged with mating components and the movement of the tool and/or steerable shaft.

The following describes relates to the 1206' handle shell features that relate to the deflection of the catheter sheath. The handle shell features can be described generally as integral ribs (also referred to as "walls" herein) embossed and extending radially inward from the radial surface of the handle shell that serve as bearing surfaces, rails, or guides that also constrain the mating components. For example, with reference to FIGS. 44A and 44B, components constrained by the handle shell 1206' include the components identified by the following reference numerals: 1950, 1400, 1220, 1408, 1406, and 1402. FIG. 44A shows all of the deflection components constrained by 1206' in their assembled state. FIG. 44B shows all of the same components in FIG. 44A but in an exploded view. Steering actuator 1220 and deflection limiter 1408 are constrained by features 1501 and 1502 on handle shell 1206', in this embodiment walls that are extending in the width dimension, orthogonal to the length dimension, each having a recessed region formed therein. These features only allow actuator 1220 and limiter 1408 to rotate around their central axis. These components rotate freely until the deflection limiter prevents further rotation as described elsewhere herein. Gasket 1406 creates friction between 1220 and 1501. The friction is achieved by slightly compressing 1406 against 1501 as described elsewhere herein. Spindle 1400, which mates with the steering actuator 1220 as described herein is constrained between 1206' handle shell features 1503, 1504, 1505, 1506, wall 1507 having a recess formed therein, and wall 1508 having a recess formed therein and steering actuator 1220 and spindle support 1402. The spindle 1400 is constrained so it can only rotate around its central axis. Spindle support 1402 is fixed in place by wall features 1507 and 1508, having recessed formed herein, of handle shell 1206' and has no freedom of movement. Wall 1507 and 1507, which extend along the width dimension, can at least partially define a guide for spindle support 1402. The hemostasis valve assembly 1950 is fixed in place by handle shell wall features 1509 and 1510, which extend in the width dimension and at least partially define a guide for the hemostasis valve. Spindle support 1402 and hemostasis valve 1950 may additionally be permanently affixed to their respective features of handle shell 1206' with adhesive to help facilitate complete closure of the handle shells. In this embodiment the integrated handle body includes a central region that includes at least one guide (e.g., the guide for the hemostasis valve and/or guide for the spindle support 1402), the at least one central guide including walls that are orthogonal to guide walls in proximal and distal regions of the handle body 1206 that support shafts 1237 and corresponding gears that facilitate movement of the medical tool.

This and other embodiments herein are example of handle bodies that include integrated features that allow a medical tool control system to extend further proximally than a proximal end of a steerable shaft, and to be actuated by a distal actuator.

Figure 44D:
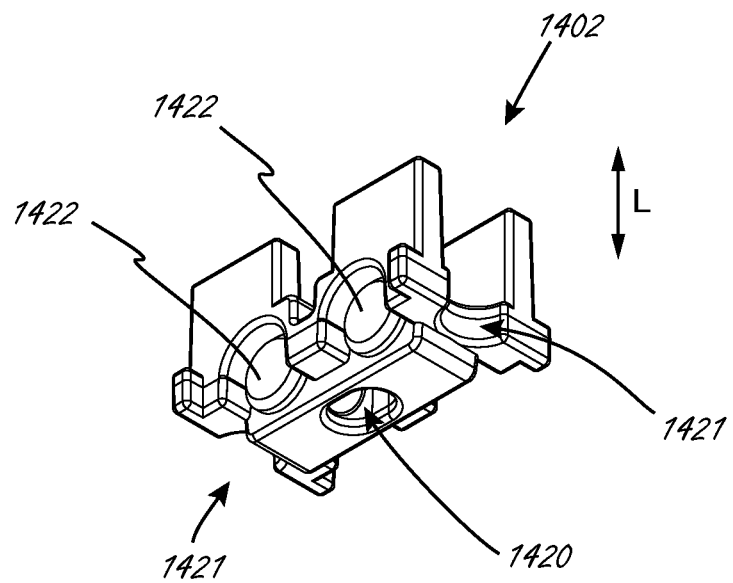
Figure 44E:
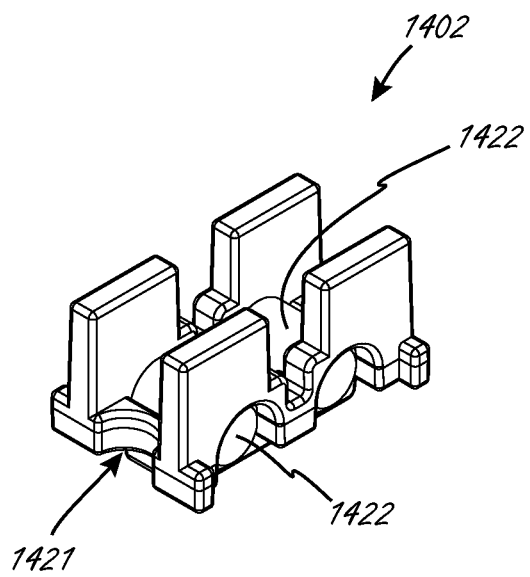

FIGS. 44D and 44E provide front and back perspective views of spindle support 1402, respectively. Spindle support 1402 supports spindles 1400 within the handle assembly. Spindle support 1402 includes central lumen 1420 sized and configured to allow the steerable shaft to pass therethrough (as well as tool passing through the steerable shaft). Spindle support 1402 includes two bearing surfaces 1422 (e.g., such as part of pins 1402' described herein), which can be separate components from the rest of support 1402 or can be integrally formed therein. In some embodiments surfaces 1422 can be part of generally cylindrically configured components disposed within guides in the support 1402. For example, each cylindrical element (e.g., pins 1402') can have an axis that is orthogonal to an axis of the parts of the spindles 1400 around which the pullwire is spooled. The description herein related to part 1402' applies equally to any of the supports 1402 herein. Support 1402 also includes two recessed regions 1421, each of which is configured to receive and provide stability to one of the spindles 1400.

In some embodiments the length L of support 1420 is 0.4 inches to 0.6 inches, such as 0.5 inches. In some embodiments the width W of support is 0.4 inches to 0.65 inches, such as 0.55 inches. In some embodiments the height H of support 1402 is 0.6 inches to 1.1 inches, such as 0.85 inches. In some embodiments the diameters of the components that comprise the bearing surfaces 1422 are from 0.15 inches to 0.35 inches, such as 0.22 inches.

Figure 50:
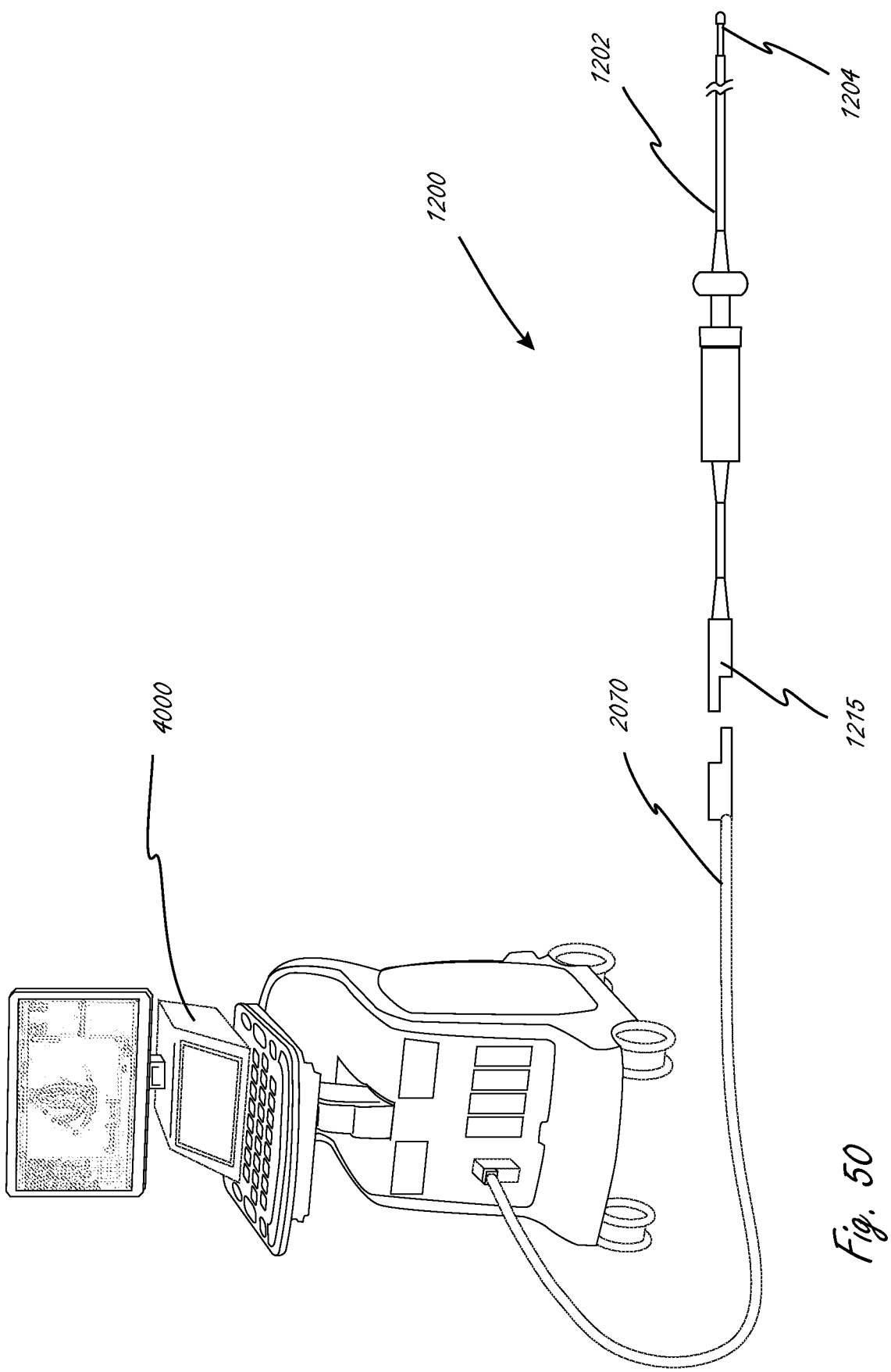
FIG. 50 illustrates an integrated system of the steerable sheath and medical tool wherein the system is connected to a console via a connector cable.
Figure 51:
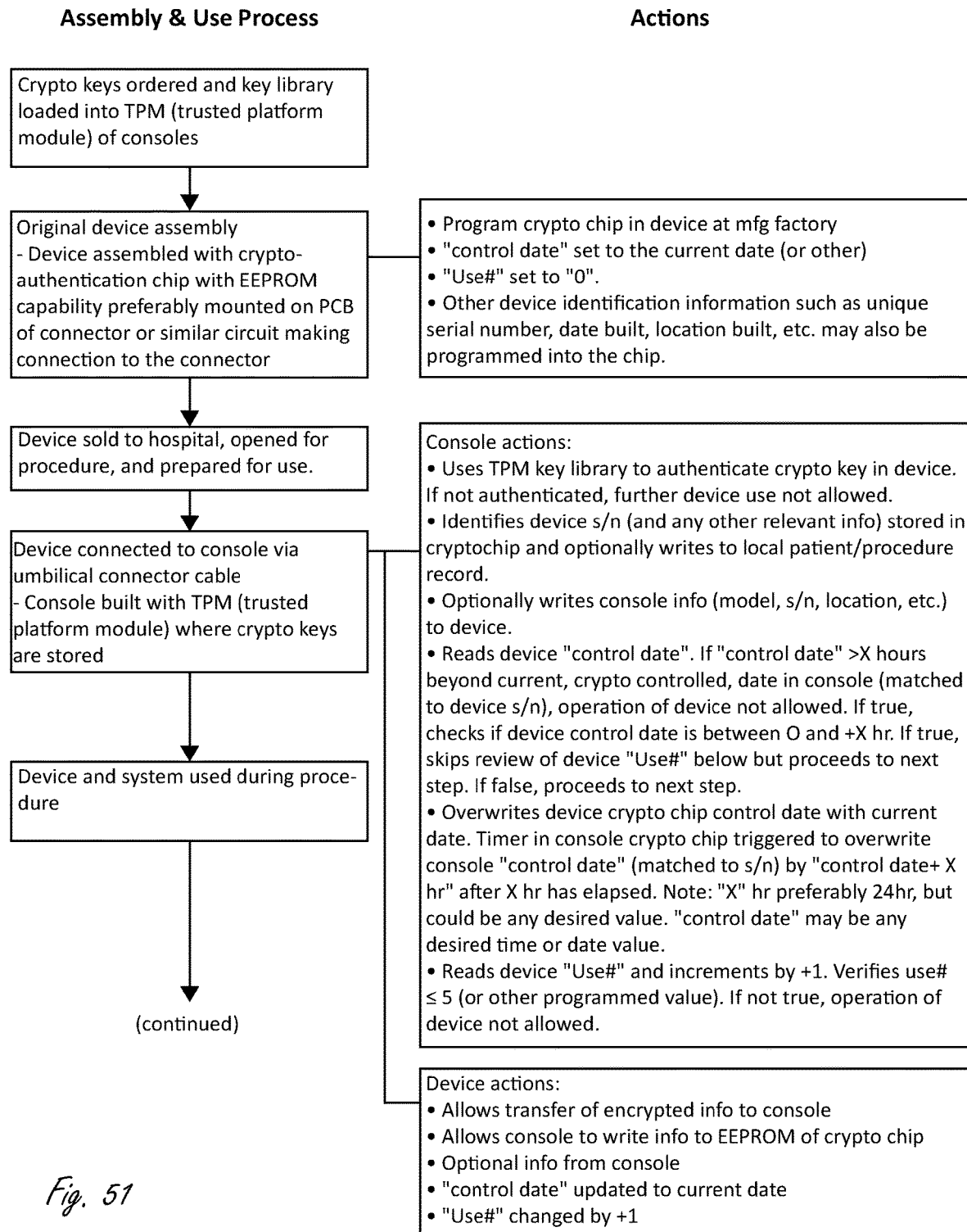
FIG. 51 illustrates an exemplary process of how systems herein and a console may communicate to control use and reuse of systems herein.
Figure 51:
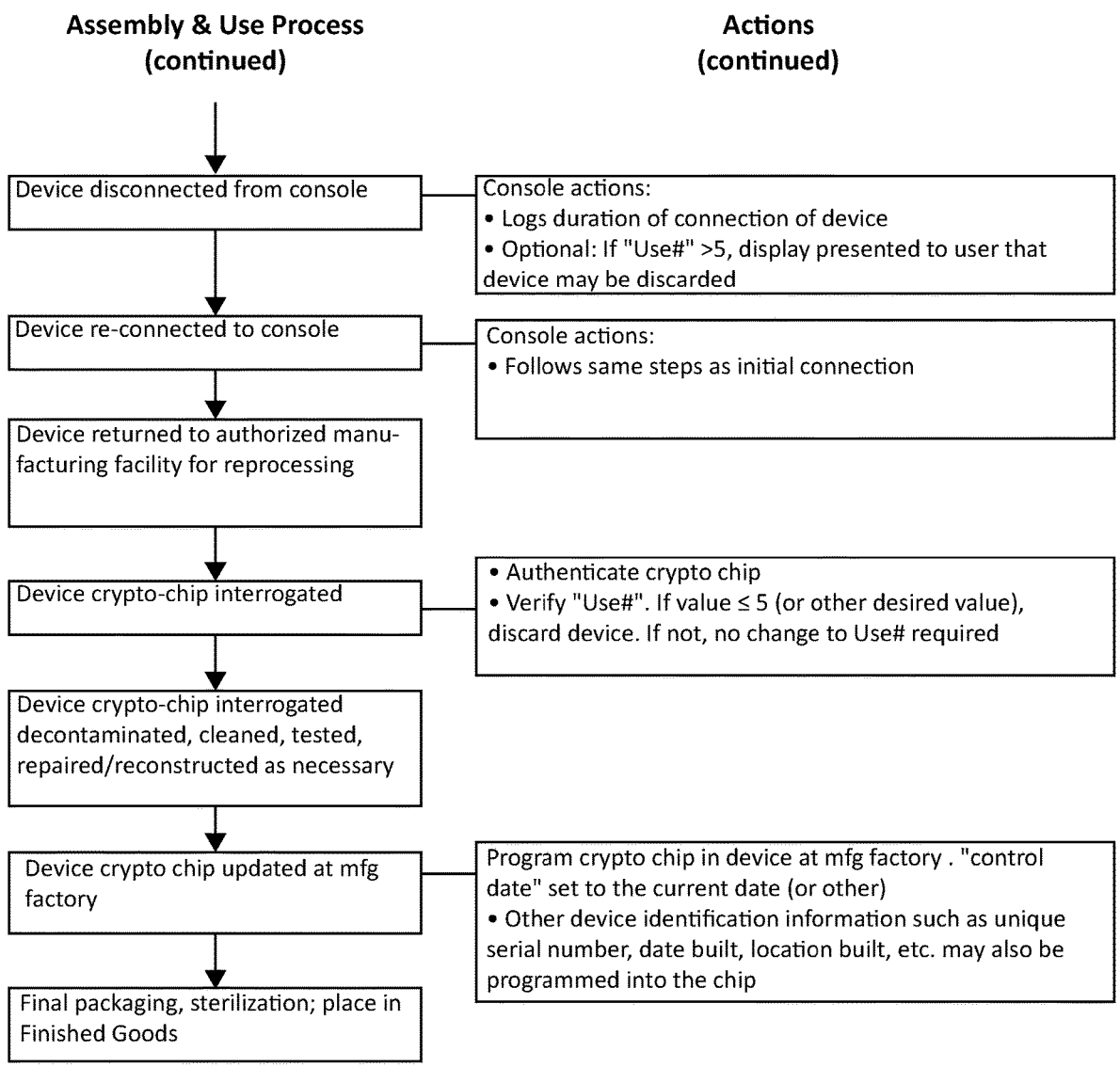

FIG. 50 illustrates the integrated system 1200 of the steerable sheath 1202 and medical tool 1204 wherein the system 1200 is connected to console 4000 via the connector cable 2070. As previously described, such as for FIG. 19, the tool 1204 comprises a proximal connector 2015 which forms a mating connection to cable 2070. As previously described, it is desirable to repose (e.g., reprocess and reuse) the system 1200. It is further desirable to ensure that the system is reposed only by the original manufacturer and not an unaffiliated third-party, and to ensure the device is only reused a specified number of times. To control the reposing process, a crypto-authentication chip (crypto-chip) is incorporated into the tool 1204, preferably on the PCB 2030, although other locations, such as within the steerable handle 1206, or within the tip 3000, are contemplated. The crypto-chip is programmable only by the original manufacturer who controls the authentication keys. The console 4000 to which the system 1200 is connected has a Trusted Platform Module (TPM) which also has the authentication keys. During use of the system 1200, the console 4000 is able to authenticate the system 1200 via the crypto-chip and as desired may read and write information to the chip (e.g., via an EEPROM feature). In any of the scenarios discussed, RFID chips, preferably encrypted, may be used to read and transmit data between the console, connector, and the device. A more detailed description of how the system 1200 and console 4000 may communicate to control use and reuse of the system 1200 is described in FIG. 51. In an embodiment related to the mechanical key of FIGS. 33 and 34, the console authentication may be required to unlock the tool tip from the steerable catheter tip.

Since the reposing process relies on the return of devices for reposing, reliable collection of devices is critical. To incentivize collection, stakeholders (e.g., physician, hospital lab staff, hospital purchasers, manufacturer sales personnel) should be motivated to return the devices. One means would be to provide a rebate based on documented device return. Other ways include providing reminders to lab personnel of the need to return the devices in good condition. A collection box provided by the manufacturer which automatically logs the return of devices is contemplated. The box may have one or more receptacles or containers for the placement of one or more devices (e.g., ICE catheters). The container may comprise or include a sealable liquid resistant bag to provide a biohazard barrier for the device. The container may alternatively or additionally comprise a hollow shape such as a rigid tube to protect the device. The hollow shape may be configured to accept cap making a seal with the hollow shape and may be further configured to plug into the device connector for communication with the container and/or collection box. The hollow shape may be configured with a means to provide a sterile seal with permeability for ethylene oxide sterilant. The receptacle or container may have a one-way lock which prevents device removal once secured in the box, preferably such that once engaged to record and/or authorize return, removal is not possible. Alternatively, if removed, the box erases or modifies the record of the return to indicate removal. The box itself may be shipped back to the manufacturer or other authorized third party for reprocessing, or may be placed in a secondary protective shipping box for shipping. The box may contain an RFID reader which reads information from the device (e.g., serial number, date sold, date of use, location of use, etc.). Some of this information may have been just written to the device from the console. A reusable connector in the collection box or container may also be provided which provides a direct connection to the device to read the information, and as necessary, write to the device to log a record of the return. This connector could be built into the container sealable cap described above. As with the console, the box itself may be configured with encryption technology, including a TPM unit in the box itself. The box may be battery powered and/or plugged into a wall outlet. The battery is serviceable by being preferably removable, rechargeable, and/or replaceable to maintain the power source. A manufacturer representative or local lab staff may provide this service. The collection box may be configured to provide wireless (e.g., WIFI, Bluetooth) or wired (e.g., Ethernet) connection between the console and/or a direct hospital and/or cloud server (accessible by the manufacturer or authorized third party) to transmit and/or receive information about the device return. This communication may include information relating to the presence and number of devices that are ready to return to signal the manufacturer or other third party to collection and return the box. To allow storage of the collection box in any desired area of the hospital, and to prevent access during shipping, the exterior of the collection box may be designed with an air and/or liquid tight seal such that when closed, biohazard contamination is not possible. A lockable door, lid, or other suitable access point may be provided. The collection box may be configured with attachment points that makes it easy to physically attach to and/or electronically communicate with the console with which the device is used. The collection box may be the same box in which the sterile product is originally shipped to the hospital.

The device connector may be fitted with a battery and circuit which provides an audible and or flashing visual alert when the device connector is initially unplugged from the umbilical connector to the console. This alert may continue until the device is plugged back into the connector or is recognized by the collection box by being placed within proximity of a collection box RFID sensor or plugged directly into the collection box receptacle or container.

In another embodiment, the device may be fitted with a detachable or breakaway component which must be removed in order to fit the device into the collection box receptacle or container. This component may be placed in a separate location of the collection box or it may be discarded. The removal of the component may render the device unusable until reposed by the manufacturer.

During manipulation of the catheter system 1200, the imaging tip may contact cardiac structures. To minimize potential damage to delicate structures (e.g., thin cardiac walls, valve leaflets), it may be advantageous to provide a more atraumatic feature on the distal tip of the tool (or, in specific embodiments, the ultrasound probe tip). In particular, this feature preferably distributes the contact force over a larger area surface area of the tip and/or is allowed to buckle or deflect to cushion the force of the tip against the tissue. The atraumatic feature is preferable placed distal to the tip where it can expand to a larger dimension and surface area and not interfere with the ultrasound imaging. FIG. 52 illustrates a variety of expandable atraumatic tip features. Expansion could be accomplished with an inflatable balloon or using a spring-like structure. The inflatable balloon may be comprised of a compliant material such as silicone or polyurethane, or a relatively non-compliant material such as nylon or polyester, or a material with compliance between the two. The spring-like structure is preferably constructed from nickel titanium or a cold worked stainless steel, but could also be fabricated from a polymer such as nylon, polyester, polypropylene, or ePTFE. The spring-like structure may be configured as a J-shaped or "pig-tail" curl of a given element, basket-shaped group of splines (straight or helical), a braid of wire elements, a coil, a loop or group of loops, or a laser cut sheet or hypotube. Elements of these structures may be formed of round wire or ribbon or sheet having a rectangular cross-section. In other embodiments a given element of the structure may itself be a coil or braid of smaller elements. In other embodiments, the feature may be a annular shaped composite of elements described above surrounded by or coated with an elastic polymer matrix such as silicone or polyurethane. In another embodiment, an annular array of curved flower petal shaped surfaces could be provided such that the surfaces slid against one another to expand and collapse. Some embodiments may be configured to be self-expanding, expanded through actuation of an element, or by inflation with a fluid or gas.

For initial entry into the body, the self-expanding element may be constrained in a collapsed shape by a tubular sheath element fitted over the outside of the catheter tip. This tubular sheath element may be retracted as soon as the device enters the blood vessel (or more generally, body lumen) from an introducer, or after it reaches the target location (e.g., chambers of the heart). The introducer sheath itself may suffice to constrain the expandable element long enough to allow entry into the vessel or body lumen. For example, the leading edge of a J-shape, pig-tail, or braid, could be manually straightened long enough for advancement through the hemostasis valve of an introducer sheath and constrained within the sheath until it exits the sheath tip. In most examples, such as where the feature is attached to the device tip at the proximal end of the feature, but the distal end is unconstrained, the feature self-straightens and/or collapses as it is tensioned and/or radially compressed during withdrawal through a vessel, body lumen, or introducer sheath. Attachment of the atraumatic feature to the tip could be accomplished by incorporating a metal ring or disk into the distal tip of the catheter, to which the structure is welded or soldered. The ring or disk could also be a feature continuous with splines extending away from it, such as splines laser cut from a nitinol hypotube and then heat set into an expanded shape. As necessary, removal of material from the ring portion could also facilitate encapsulation within the polymer of the catheter tip. As noted above, the surface of such a structure could be overmolded with silicone or polyurethane, including a rounded tip of then polymer to create a self-expanding and collapsible volume. The support structure for the atraumatic tip could be insert molded within the mold for the polymer tip within which the transducer is assembled. The atraumatic tip feature could also incorporate elements which extend proximally behind the transducer (non-imaging side) where they are secured within the tip via adhesive bonding, welding, soldering, heat fusing a polymer, or any combination thereof.

FIG. 52 illustrates a selection of such tips.

As used herein, "cleaning" can refer to any type of cleaning, such as without limitation: cleaning an interior of an outer shaft using a flushing system of cleaner and/or disinfectant and optionally mechanical scrubbing with small brushes; mechanical cleaning (e.g., wipes, brushes) an outer portion of an outer shaft and/or outer portion of a medical device shaft (e.g., ultrasound probe) with a cleaner/disinfectant, and optionally submerging the shaft in an ultrasound bath of cleaner/disinfectant for a specified period of time. "Cleaning" as used here does not refer to a specific cleaning process, but rather refers to the general idea of cleaning an object.

The disclosure herein also includes methods of assembling or reassembling any of the subassemblies or assemblies herein, including any of the subassemblies within any of the handle assemblies herein. For example without limitation, the disclosure here includes methods of spooling one or more pull wires over a bearing surface in a spindle support and then around the spindle.

The methods herein also include manufacturing or constructing any of the individual components of any of the subassemblies or assemblies herein. For example, the disclosure includes methods of manufacturing handle shell components that have particular configurations (e.g., guides, walls, etc.) that can accommodate the internal parts that allow the assemblies or subassemblies herein to function as intended.

Regardless of the reference number with which they are labeled, any of the handle assemblies, medical tools, steerable sheaths, and electrical connections herein can be used together in a system in any combination with each other.

Any of the technology, including ultrasound and steering technology, in any of the following U.S. patent references may be incorporated into any of the medical tools, devices, systems, or methods of use thereof herein, the disclosures of which are incorporated by reference herein: U.S. Pat. Nos. 6,100,626, 6,537,217, 6,559,389, 7,257,051, 7,297,118, 7,331,927, 7,338,450, 7,451,650, 7,451,650, 7,527,591, 7,527,592, 7,569,015, 7,621,028, 7,731,516, 7,740,584, 7,766,833, 7,783,339, 7,791,252, 7,791,252, 7,819,802, 7,824,335, 7,966,058, 8,057,397, 8,096,951, 8,207,652, 8,207,652, 8,213,693, 8,364,242, 8,428,690, 8,451,155, 8,527,032, 8,659,212, 8,721,553, 8,727,993, 8,742,646, 8,742,646, 8,776,335, 8,790,262, 8,933,613, 8,978,216, 8,989,842, 9,055,883, 9,439,625, 9,575,165, 9,639,056, and 20080287783.

What is claimed is:

1. An ultrasound probe positioning system, comprising: a handle assembly; a steerable sheath; and an ultrasound probe,
the handle assembly in operable communication with the steerable sheath and the ultrasound probe,
the handle assembly including a handle body with an outer surface positioned to be gripped by a user, a distal ultrasound probe actuator adapted to be moved relative to the handle body, and a proximal steerable sheath actuator proximal to the distal actuator adapted to be moved relative to the handle body,
the steerable sheath having a distal deflectable region that is in operable communication with at least one axially actuatable member, wherein the proximal steerable sheath actuator is in operable communication with the axially actuatable member such that actuation of the proximal steerable sheath actuator relative to the handle body causes deflection of the distal deflectable region, and
wherein the distal actuator is adapted to be rotated relative to the handle body and also adapted to be moved axially relative to the handle body, and wherein the distal actuator is in operable communication with the ultrasound probe such that axial movement of the distal actuator relative to the handle body causes axial movement of the ultrasound probe relative to a distal end of the steerable sheath, and such that rotation of the distal actuator relative to the handle body causes rotation of the ultrasound probe relative to the distal end of the steerable sheath,
wherein the handle assembly comprises an ultrasound probe displacement system that is attached to the distal ultrasound probe actuator and to an ultrasound probe shaft such that it creates rotational and axial communication between the distal ultrasound probe actuator and the ultrasound probe shaft,
wherein the ultrasound probe displacement system comprises a central gear with a lumen through which the steerable sheath and the ultrasound probe shaft extend, the central gear in rotational communication with a second gear, the second gear in rotational communication with the ultrasound probe shaft, and
wherein at least part of the ultrasound probe displacement system is disposed within the handle body and extends further proximally in the handle body than a proximal end of the steerable sheath and is attached to the ultrasound probe shaft at a location proximal to the proximal end of the steerable sheath, and
wherein the ultrasound probe displacement system bypasses the steerable sheath within the handle body such that it is not in operable communication with the steerable sheath within the handle body so that the ultrasound probe shaft can be rotated and axially moved without causing movement of the steerable sheath within the handle body.

2. The system of claim 1, wherein the part of the ultrasound probe displacement system that is attached to the ultrasound probe shaft is attached to the ultrasound probe shaft proximal to a hemostatic valve disposed within the handle body.

3. The system of claim 1, wherein the central gear is adapted to be moved axially relative to the steerable sheath when the distal actuator is moved axially.

4. The system of claim 1, wherein the ultrasound probe displacement system further comprises a third gear with a proximal end that is proximal to the proximal end of the steerable sheath, the third gear positioned radially inward relative to the second gear, the third gear having a lumen through which the ultrasound probe shaft extends and which is secured directly or indirectly to the ultrasound probe shaft.

5. The system of claim 1, wherein the system further comprises a compound ultrasound probe rotation limiter assembly disposed within the handle body and in rotational communication with the ultrasound probe shaft and adapted such that it prevents the ultrasound probe within the handle body from being rotated beyond a certain amount.

6. The system of claim 5, wherein the compound ultrasound probe rotation limiter assembly allows for the proximal portion of the ultrasound probe within the handle body to be rotated greater than 360 degrees, and prevents rotation of more than 720 degrees.

7. The system of claim 1, wherein the ultrasound probe has a distal portion that includes an ultrasound transducer, the distal portion extending further distally than a distal end of the steerable sheath and having a radially outer dimension greater than a radial dimension of a lumen of the steerable sheath in which the probe is disposed, the ultrasound probe further including a flexible circuit strip, the flexible circuit strip comprising an insulating substrate, a plurality of conductive traces disposed on and extending along the insulating substrate, a portion of each of the plurality of conductive traces covered by an insulation member, and a portion of the plurality of conductive traces not covered by the insulation member, the portion of the plurality of conductive traces that are not covered by the second insulation layer defining a probe contact.

8. The system of claim 5, wherein at least a portion of the ultrasound probe rotation limiter assembly is disposed proximal to the proximal end of the steerable shaft and proximal to a hemostatic valve disposed in the handle body.

9. The system of claim 6, wherein the compound ultrasound probe rotation limiter assembly prevents rotation of more than 450 degrees.

* * * * *